(12) United States Patent
Flohr et al.

(10) Patent No.: US 7,211,573 B2
(45) Date of Patent: May 1, 2007

(54) MALONAMIDE DERIVATIVES

(75) Inventors: Alexander Flohr, Reinach (CH); Roland Jakob-Roetne, Inzlingen (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/289,176

(22) Filed: Nov. 30, 2005

(65) Prior Publication Data
US 2006/0122168 A1 Jun. 8, 2006

(30) Foreign Application Priority Data
Dec. 8, 2004 (EP) .................. 04106395
Feb. 7, 2005 (EP) .................. 05100816

(51) Int. Cl.
C07D 267/14 (2006.01)
A61K 31/553 (2006.01)

(52) U.S. Cl. .................. 514/211.06; 540/491
(58) Field of Classification Search ......... 540/491; 514/211.06
See application file for complete search history.

(56) References Cited

FOREIGN PATENT DOCUMENTS

| WO | WO 01/90084 | 11/2001 |
|---|---|---|
| WO | WO 2004/069826 A1 | 8/2004 |
| WO | WO 2004/100958 A1 | 11/2004 |
| WO | WO 2005/023772 A1 | 3/2005 |
| WO | WO 2005/040126 A1 | 5/2005 |

OTHER PUBLICATIONS

Haass, C., The EMBO Journal (2004), 23, pp. 483-488.
Fraering, et al., Biochemistry (2004), 43 (30), pp. 9774-9789.
Sisodia, et al. Nature Reviews/Neuroscience, vol. 3, (Apr. 2002) pp. 281-290.
Beher et al., Biochemical Society Transactions (2002), vol. 30. part 4, pp. 534-537.
Wolfe, M., Current Topics in Medicinal Chemistry, 2002, 2, 371-383.
Tsai, et al., Current Medicinal Chemistry, 2002, vol. 9, No. 11, 1087-1106.
Sambamurti et al., Drug Development Research, 56, 211-227, 2002.
May, P., Drug Discovery Today, vol. 6, No. 9, May 2001, 459-462.
Nunan, et al., FEBS Letters, 483, (2000), 6-10.
Hardy, et al., Science, vol. 297, 353-356, Jul. 2002.
Wolfe, M., Journ. of Medicinal Chemistry, vol. 44, No. 13, 2001, 2039-2060.
Brockhaus et al., Neuroreport 9(7) 1481-1486 (1998).
Itoh, et al., Chem. Pharm. Bull. 1986, 34(3) p. 1128-1147.
Herreman et al., Nature Cell Biology 2, 461-462, 2000.
De Stropper et al., Nature 398, 518-522, 1999.
Chung et al., Nature Cell Biology 3, 1129-1132, 2001.
Hadland et al., PNAS 98, 7487-7491, 2001.
Ferrando et al., Cancer Cell 1, 75-87, 2002.
Weng et al., Science 306, 269-271, 2004.
Weng et al., Mol Cell Biol 23, 655-664, 2003.
Weijzen et al., Nature Medicine 8, 979-986, 2002.
Nickoloff et al., Oncogene 22, 6598-6608, 2003.
Li et al., PNAS 97(11) 6138-6143, 2000.

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to compounds of the formula I

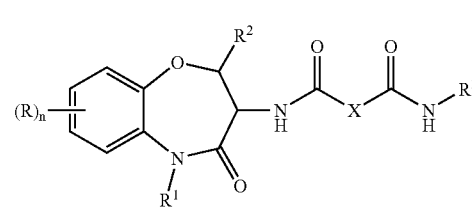

wherein
R, $R^1$, $R^2$, $R^3$, X, and
n are defined in the specification. The invention also provides pharmaceutically suitable acid addition salts thereof and all forms of optically pure enantiomers, recemates or diastereomers and diastereomeric mixtures thereof. Compounds of the invention are useful for the treatment of Alzheimer's disease.

21 Claims, No Drawings

US 7,211,573 B2

MALONAMIDE DERIVATIVES

PRIORITY TO RELATED APPLICATIONS

This application claims the benefit of European Application Nos. 04106395.9, filed Dec. 8, 2004, and 05100816.7, filed Feb. 7, 2005 which are hereby incorporated by reference in their entirety.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein-(APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substates and which are themselves polytopic membrane proteins. Other essential components of γ-secretase may be presenilin, nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch. It was demonstrated by genetic means, i.e., ablation of either the presenilin 1 and 2 genes or the nicastrin gene, that γ-secretase is absolutely required for Notch signaling. This was subsequently confirmed by treatment with specific γ-secretase inhibitors.

Notch receptors are not only essential in embryonal development but also play a critical role in several tissues of the adult organism which continue to undergo proliferation and differentiation, e.g., hematopoietic cells and epithelia of the gut and skin. The signaling of Notch receptors occurs through an ordered sequence of events: binding to a ligand of the Delta or Jagged group, cleavage of the extracellular domain by an ADAM protease (TACE) and subsequent cleavage by the γ-secretase within the Notch transmembrane domain. The latter cleavage results in the liberation of the cytoplasmic domain which then translocates to the nucleus where it acts with other proteins as a regulator of a specific group of genes.

A role for Notch in human oncogenesis was most dearly established for T-cell Acute Lymphoblastic Leukemia (T-ALL). Some rare cases of T-ALL show a (7:9) chromosomal translocation which leads to a constitutive activation of Notch1. Recently it was reported that ca. 50% of all T-ALL cases have point mutation in the Notch1 receptor which also cause over-activation. It was shown that growth of some cell lines derived from such leukemias were sensitive to treatment with γ-secretase inhibitors which confirmed an essential role for Notch1 signaling.

A broader role for Notch in oncogenesis is discussed in several recent papers which descibe that its signaling is required for maintaining the neoplastic phenotype in ras-transformed cells. Deregulation of the ras-signaling pathway is found in a number of common cancers including cervical carcinomas and breast carcinomas.

The γ-secretase activity is absolutely required for the production of Abeta peptides. This has been shown both by genetic means, i.e., ablation of the presenilin genes and by low-molecular-weight inhibitory compounds. Since according to the amyloid hypothesis of AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:

The EMBO Journal (2204), 23, 483–488,
Biochemistry (2004), 43 (30), 9774–9789,
Nature Reviews/Neuroscience, Vol. 3, April 2002/281,
Biochemical Society Transactions (2002), Vol. 30. part 4,
Current Topics in Medicinal Chemistry, 2002, 2, 371–383,
Current Medicinal Chemistry, 2002, Vol. 9, No. 11, 1087–1106,
Drug Development Research, 56, 211–227, 2002,
Drug Discovery Today, Vol. 6, No. 9, May 2001, 459–462,
FEBS Letters, 483, (2000), 6–10,
Science, Vol. 297, 353–356, July 2002,
Journ. of Medicinal Chemistry, Vol. 44, No. 13, 2001, 2039–2060, Nature Cell Biology 2, 461–462, 2000,
Nature 398, 518–522, 1999,
Nature Cell Biology 3, 1129–1132, 2001,
PNAS 98, 7487–7491, 2001,
Cancer Cell 1, 75–87, 2002,
Science 306, 269–271, 2004,
Mol Cell Biol 23, 655–664, 2003,
Nature Medicine 8, 979–986, 2002 and
Oncogene 22, 6598–6608, 2003.

SUMMARY OF THE INVENTION

The invention provides compounds of formula I

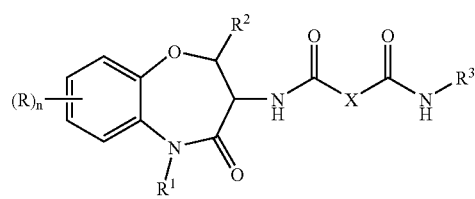

I wherein

R is halogen, lower alkyl or lower alkyl substituted by halogen;

$R^1$ is hydrogen, lower alkyl, lower alkyl substituted by halogen or hydroxy, lower alkenyl, —$(CH_2)_n$-cycloalkyl, —$(CH_2)_n$—COR', benzyl optionally substituted by halogen, or —$(CH_2)_n$-morpholinyl;

R' is lower alkoxy, hydroxy or amino;

$R^2$ is hydrogen, lower alkyl, di-lower alkyl, lower alkyl substituted by halogen or hydroxy, benzyl, or cycloalkyl;

$R^3$ is lower alkyl, lower alkyl substituted by halogen, benzyl optionally substituted by two halogen atoms, —$(CH_2)_n$-cycloalkyl, or —$(CH_2)_n$-pyridinyl;

X is —$CR^4R^{4'}$— or —$CR^4R^{4'}$—O—;

$R^4$ and $R^{4'}$ are each independently hydrogen, halogen, lower alkyl, lower alkoxy, hydroxy, or —$CH_2$-2-[1,3]dioxalan-; and n is 0, 1, or 2;

and pharmaceutically suitable acid addition salts thereof. The invention provides for are all forms of optically pure enantiomers, recemates or diastereomers and diastereomeric mixtures for compounds of formula I.

The invention also provides pharmaceutical compositions containing compounds of the invention. The invention further provides processes for the preparation of compounds of the invention and for the manufacture of pharmaceutical compositions containing them.

Compounds of formula I are γ-secretase inhibitors. Thus, compounds of the invention can be useful in the treatment of Alzheimer's disease or common cancers, including, but not limited to, cervical carcinomas and breast carcinomas and malignancies of the hematopoietic system. The compounds of this invention will be useful for treating AD by blocking the activity of γ-secretase and reducing or preventing the formation of the various amyloidogenic Abeta peptides. Furthermore, the compounds of this invention can be used to treat tumors and proliferative disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

As used herein, the term "lower alkenyl" denotes a saturated straight- or branched-chain carbon group containing from 2 to 6 carbon atoms, which contain at least one double bond.

The term "lower alkyl substituted by halogen" denotes an alkyl group as defined above, wherein at least one hydrogen atom is replaced by halogen, for example $CF_3$, $CHF_2$, $CH_2F$, $CH_2CF_3$, $CH_2CF_2CF_3$ and the like.

The term "lower alkyl substituted by hydroxy" denotes an alkyl group as defined above, wherein at least one hydrogen atom is replaced by hydroxy, for example —$(CH_2)_2OH$.

The term "cycloalkyl" denotes a saturated carbocyclic group, containing 3–7 carbon atoms.

The term "halogen" denotes chlorine, iodine, fluorine and bromine.

The term "lower alkoxy" denotes a group wherein the alkyl residues is as defined above, and which is attached via an oxygen atom.

"Pharmaceutically acceptable" such as pharmaceutically acceptable carrier, excipient, etc., means pharmacologically acceptable and substantially non-toxic to the subject to which the particular compound is administered.

The term "pharmaceutically suitable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The invention provides compounds of formula I

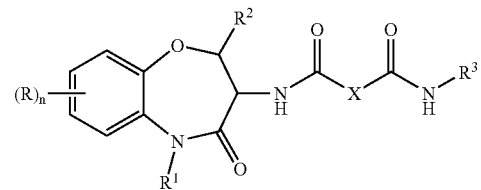

wherein

R is halogen, lower alkyl or lower alkyl substituted by halogen;

$R^1$ is hydrogen, lower alkyl, lower alkyl substituted by halogen or hydroxy, lower alkenyl, —$(CH_2)_n$-cycloalkyl, —$(CH_2)_r$—COR', benzyl optionally substituted by halogen, or —$(CH_2)_n$-morpholinyl;

R' is lower alkoxy, hydroxy or amino;

$R^2$ is hydrogen, lower alkyl, di-lower alkyl, lower alkyl substituted by halogen or hydroxy, benzyl, or cycloalkyl;

$R^3$ is lower alkyl, lower alkyl substituted by halogen, benzyl optionally substituted by two halogen atoms, —$(CH_2)_n$-cycloalkyl, or —$(CH_2)_n$-pyridinyl;

X is —$CR^4R^{4'}$— or —$CR^4R^{4'}$—O—;

$R^4$ and $R^{4'}$ are each independently hydrogen, halogen, lower alkyl, lower alkoxy, hydroxy, or —$CH_2$-2-[1,3]dioxalan-; and n is 0, 1, or 2;

and pharmaceutically suitable acid addition salts thereof. The invention provides for are all forms of optically pure enantiomers, recemates or diastereomers and diastereomeric mixtures for compounds of formula I.

Preferred compounds are those wherein X is —$CH_2$—, —$CHCH_3$—, —$CH(CH_2CH_3)$—, —$C(CH_3)_2$—, —$C(CH_3)(OH)$—, —$C(CH_3)_2$—O—, —$CH(OCH_3)$— or —$C(F)(CH_2CH_2CH_3)$—. In detail, preferred compounds are those wherein X is —$CHCH_3$— or —$CH(CH_2CH_3)$—.

Compounds of this group, wherein $R^3$ is lower alkyl substituted by halogen are the following compounds:

2-methyl-N-((S)-9-methyl-8-oxo-6,7,8,9-tetrahydro-5-oxa-9-aza-benzocyclohepten-7-yl)-N'-(2,2,3,3,3-pentafluoro-propyl)-malonamide, 2-methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide, 2-methyl-N-((6R,7S)-6-methyl-8-oxo-6,7,8,9-tetrahydro-5-oxa-9-aza-benzocyclohepten-7-yl)-N'-(2,2,3,3,3-pentafluoro-propyl)-malonamide, N-((6R,7S)-1-fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide, N-((6R,7S)-2-fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide, N-((6R,7S)-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide, N-((6R,7S)-6,9-dimethyl-8-oxo-6,7,8,9-tetrahydro-5-oxa-9-aza-benzocyclohepten-7-yl)-2-ethyl-N'-(2,2,3,3,3-pentafluoro-propyl)-malonamide, N-[(6R,7S)-9-(4-chloro-benzyl)-6-methyl-8-oxo-6,7,8,9-tetrahydro-5-oxa-9-aza-benzocyclohepten-7-yl]-2-methyl-N'-(2,2,3,3,3-pentafluoro-propyl)-malonamide, N-((6R,7S)-1-fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide and N-((6R,7S)-2-fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide.

Other preferred compounds are those where X is —CH₂—.

Still other preferred compounds are those where X is —C(CH₃)₂—O—.

Further preferred are compounds where X is —CHCH₃— or —CH(CH₂CH₃)— are those wherein $R^3$ is benzyl substituted by two halogen atoms, for example the following compound N-(3,5-difluoro-benzyl)-2-methyl-N'-((6R,7S)-6-methyl-8-oxo-6,7,8,9-tetrahydro-5-oxa-9-aza-benzocyclohepten-7-yl)-malonamide.

Further preferred are compounds wherein X is —C(lower alkyl)(hydroxy).

Compounds of this group wherein $R^3$ is lower alkylsubstituted by halogen are, for example the following compounds N-((6R,7S)-6-cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide, (S or R)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, N-[(6R,7S)-2-fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, and (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide.

Further preferred compounds are those wherein X is —C(CH₃)₂.

Compounds of this group, wherein $R^3$ is lower alkyl substituted by halogen are the following compounds:

N-((6R,7S)-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-[(6R,7S)-9-(4-chloro-benzyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide, N-((6R,7S)-1-fluoro-6,9-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2,2-dimethyl-N'-(2,2,3,3,3-pentafluoro-propyl)-malonamide, N-((6R,7S)-9-cyclopropylmethyl-2-fluoro-6-methyl-8-oxo-6,7,8,9-tetrahydro-5-oxa-9-aza-benzocyclohepten-7-yl)-2,2-dimethyl-N-(2,2,3,3,3-pentafluoro-propyl)-malonamide, N-((6R,7S)-9-allyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-[(6R,7S)-2-fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide, {(6R,7S)-2-fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid methyl ester, N-((6R,7S)-6-benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-((6R,7S)-6-cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide, N-((6R,7S)-6-ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide and N-[(6R,7S)-2-fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide.

Further preferred compounds are those wherein X is —C(F)(CH$_2$CH$_2$CH$_3$)—.

Compounds of this group, wherein $R^3$ is benzyl substituted by two halogen atoms are the following compounds:

N-(3,5-difluoro-benzyl)-2-fluoro-N'-((6R,7S)-6-methyl-8-oxo-6,7,8,9-tetrahydro-5-oxa-9-aza-benzocyclohepten-7-yl)-2-propyl-malonamide and N-(3,5-difluoro-benzyl)-N'-((6R,7S)-6,9-dimethyl-8-oxo-6,7,8,9-tetrahydro-5-oxa-9-aza-benzocyclohepten-7-yl)-2-fluoro-2-propyl-malonamide.

The present compounds of formulas I and their pharmaceutically acceptable salts can be prepared by methods known in the art, for example, by processes described below, a) reacting a compound of formula

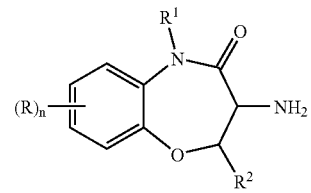

II with a compound of formula

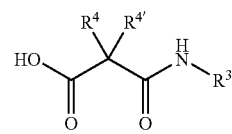

III to produce a compound of formula

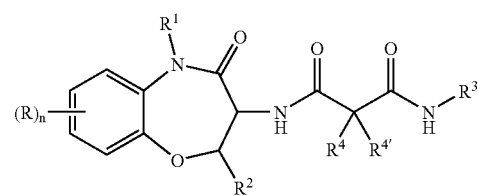

IA wherein R, $R^1$, $R^2$, $R^3$ and $R^4/R^{4'}$ and n are as described above; or b) reacting a compound of formula

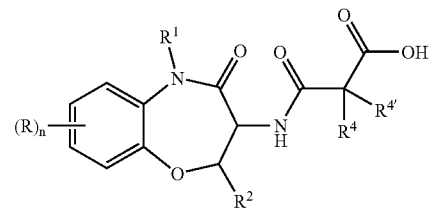

IV with a compound of formula

NH$_2$R$^3$     V to produce a compound of formula

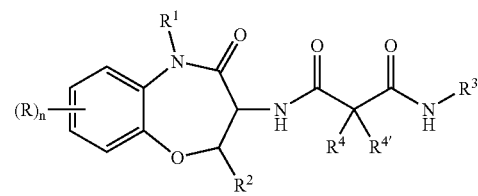

IA wherein R, $R^1$, $R^2$, $R^3$ and $R^4/R^{4'}$ and n are as described above; or c) reacting a compound of formula

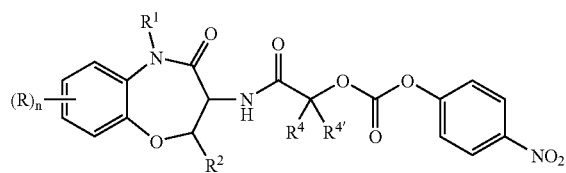

VI with a compound of formula $NH_2R^3$  V to produce a compound of formula

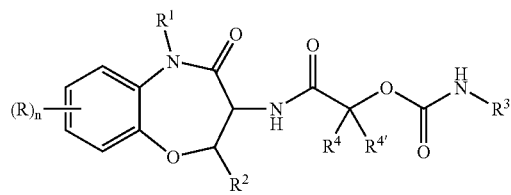

IB wherein R, $R^1$, $R^2 R^3$ and $R^4/R^{4'}$ and n are as described above; and if desired, converting the compounds obtained into pharmaceutically acceptable acid addition salts.

The compounds of formula I can be prepared in accordance with the following schemes 1–6:

Starting materials of formulas III, V, VII, VIII, XII, XIII, XIV, XVI and XVII are known compounds or can be prepared according to methods known to a skilled person.

The following abbreviations have been used:

| | |
|---|---|
| DMF | dimethylformamide |
| EDC | N-(3-dimethylaminopropyl)-N'-ethyl-carbodiimid-hydrochloride |
| HOBT | 1-hydroxybenzotriazole hydrate, |
| DIPEA | diisopropylethylamine |
| THF | tetrahydrofurane |
| LDA | Lithium diisopropylamide |

Scheme 1

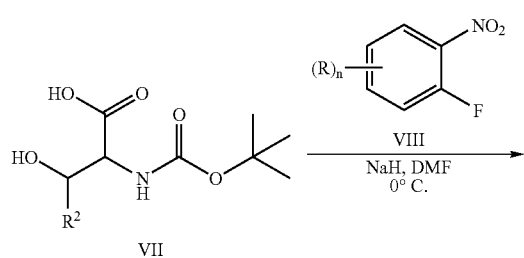

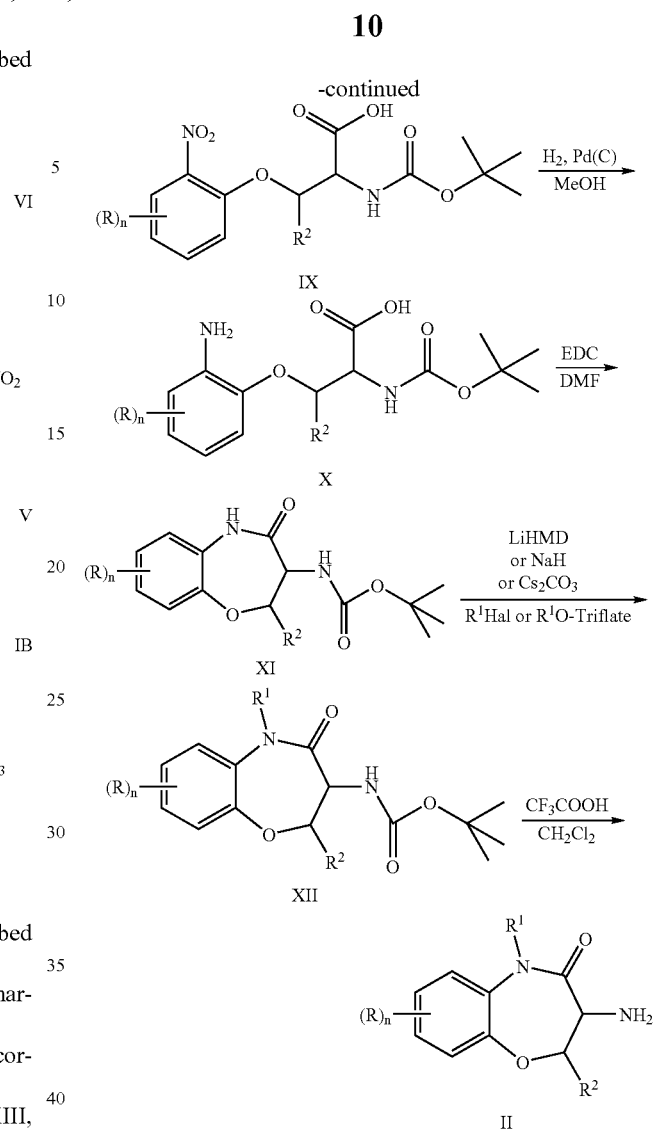

wherein R, $R^1$ and $R^2$ and n are as described above.

In accordance with scheme 1, compounds of formula II can be prepared as follows: A compound of formula VII, for example 2-tert-butoxycarbonylamino-3-hydroxy-propionic acid, in dimethylformamide is added to a suspension of sodium hydride in dimethylformamide at 0° C. The suspension is stirred for about 1 hour, and then a compound of formula VIII, for example 2,5-difluoro-nitrobenzene, is added. After additional 3 hours of stirring at 0° C., the mixture is poured on ice/water and purified. A compound of formula IX is obtained, which is then hydrogenated with Pd(10%)/C. The obtained compound of formula X is treated with N-(3-dimethylaminopropyl)-N'-ethyl-carbodiimid-hydrochloride in dimethylformamide and is stirred overnight at room temperature. A compound of formula XI is obtained, which is treated with a compound of formula $R^1$Hal or $R^1$O-triflate to produce a compound of formula XII. A corresponding compound of formula II can be obtained by treating with trifluoroacetic acid in dichloromethane for about 3 hours.

An alternative process for preparation of compounds of formula II can be prepared in accordance with scheme 2.

11

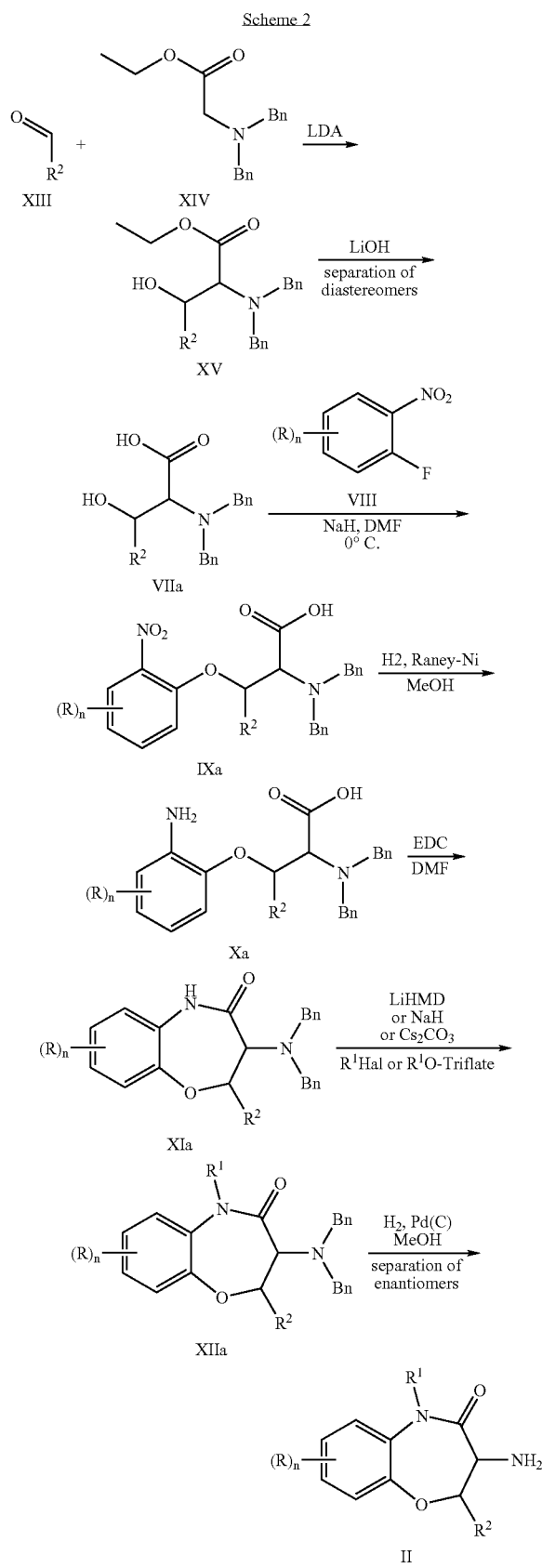

12 wherein R, $R^1$ and $R^2$ and n are as described above.

A compound of formula IA can be obtained as follows:

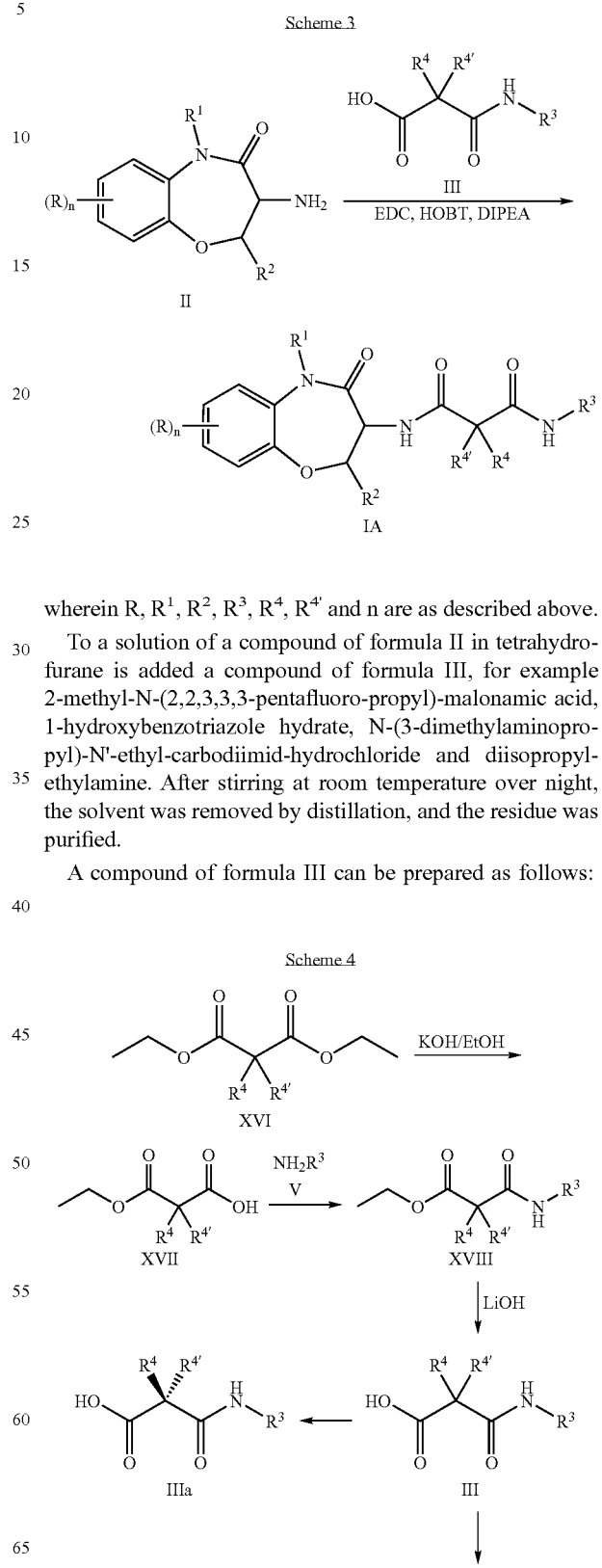

wherein R, $R^1$, $R^2$, $R^3$, $R^4$, $R^{4'}$ and n are as described above.

To a solution of a compound of formula II in tetrahydrofurane is added a compound of formula III, for example 2-methyl-N-(2,2,3,3,3-pentafluoro-propyl)-malonamic acid, 1-hydroxybenzotriazole hydrate, N-(3-dimethylaminopropyl)-N'-ethyl-carbodiimid-hydrochloride and diisopropylethylamine. After stirring at room temperature over night, the solvent was removed by distillation, and the residue was purified.

A compound of formula III can be prepared as follows:

-continued

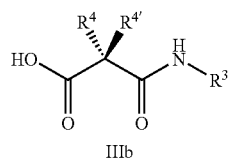

IIIb wherein the substituents are as described above.

To a solution of potassium hydroxide in ethanol, a compound of formula XVI, for example diethyl methyl-malonate, is added, and the mixture is refluxed for about 4 hours. After cooling, the reaction mixture is concentrated and purified. Then to a solution of methyl-malonic acid monoethyl ester in tetrahydrofuran, a compound of formula V; for example 2,2,3,3,3-pentafluoropropylamine; N-(3-dimethylaminopropyl)-N'-ethylcarbodiimide hydrochloride, 1-hydroxybenzotrizole hydrate and N,N-diisopropyl-ethylamine are added. The mixture is stirred at room temperature for about 18 h and purified. To this solution of a compound of formula XVIII in tetrahydrofurane, water and lithium hydroxide are added, and the mixture is stirred overnight at room temperature.

All forms of optically pure enantiomers, recemates or diastereomeric mixtures can be prepared in conventional manner or as described in Examples 1–85.

Scheme 5

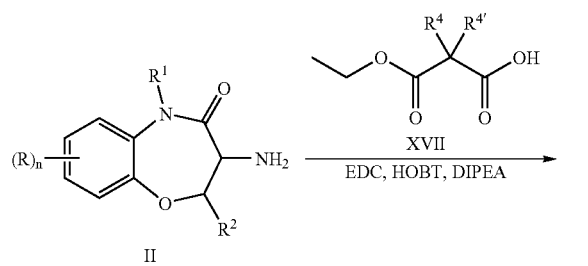

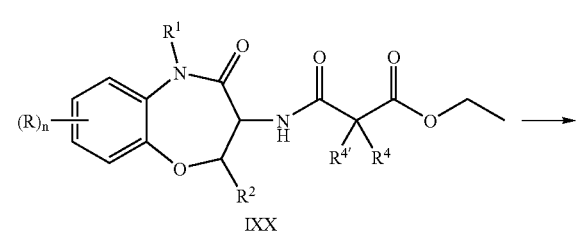

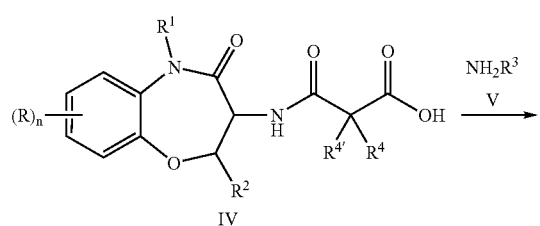

-continued

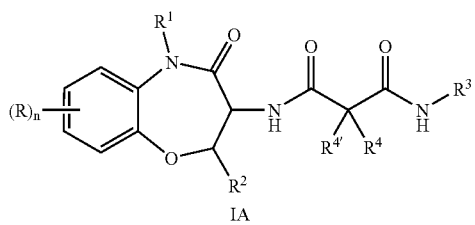

IA wherein the substituents are described above.

Scheme 6

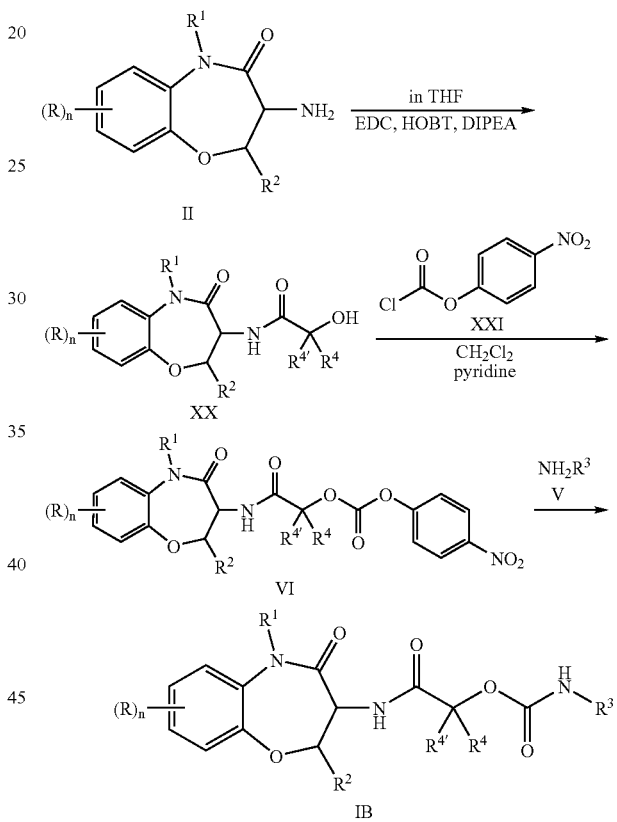

The meaning of substituents is described above.

A compound of formula IB is prepared as follows:

To a solution of a compound of formula II, for example 7-amino-9-methyl-6,7-dihydro-9H-5-oxa-9-aza-benzocycloheptan-8-one, in tetrahydrofurane is added L-(+)-lactic acid, 1-hydroxybenzotriazole hydrate, N-(3-dimethylaminopropyl)-N'-ethyl-carbodiimid-hydrochloride and diisopropylethylamine. After stirring at room temperature over night, the mixture is added to aqueous hydrochloric acid, extracted and purified.

The obtained compound of formula XX is then treated with 4-nitrophenyl chloroformate (XXI) and then with a compound of formula V, for example 2,2,3,3,3-pentafluoropropylamine, to obtain a compound of formula IB.

The detailed description of the production of compounds of the invention can be found in Examples 1–85.

Some compounds of formula I can be converted to a corresponding acid addition salt, for example compounds, containing an amine group.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of compounds of formula I can be converted to the corresponding free bases by treatment with at least a stoichiometric equivalent of a suitable base, such as sodium or potassium hydroxide, potassium carbonate, sodium bicarbonate, ammonia, and the like.

The separation of two isomers is performed in a usual manner, for example by flash-chromatography on silica gel using a gradient of a 100%:0%- to 50%:50%-mixture of heptane and ethyl acetate as the eluent.

The compounds of formulas I and their pharmaceutically usable addition salts possess valuable pharmacological properties. Specifically, compounds of the present invention inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6× Histidin tail for purification which is expressed in *E. coli* in a regulatable expression vector, e.g. pEt15. This recombinant protein corresponds to the truncated APP fragment which results after γ-secretase cleavage of the extracellular domain and which constitutes the γ-secretase substrate. The assay principle is described in Li YM et al, PNAS 97(11), 6138–6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481–1486 (1998).

Representative compounds show a $IC_{50} < 200$ nM. In the list below are described some data to the γ-secretase inhibition:

| Example No. | $IC_{50}$ in vitro |
|---|---|
| 3 | 172 |
| 12a | 177 |
| 15 | 70 |
| 17 | 190 |
| 18 | 150 |
| 21 | 160 |
| 22 | 23 |
| 23 | 30 |
| 28 | 100 |
| 31 | 110 |
| 33 | 90 |
| 34 | 80 |
| 36 | 40 |
| 37 | 70 |
| 38 | 35 |
| 39 | 170 |
| 42 | 110 |
| 51 | 29 |
| 52 | 110 |
| 53 | 90 |
| 56 | 140 |
| 63b | 15 |
| 65b | 160 |
| 66b | 30 |
| 69a | 10 |
| 70a | 7 |
| 71a | 28 |
| 73a | 130 |
| 74 | 25 |
| 78a | 19 |
| 78b | 130 |
| 79a | 14 |
| 79b | 90 |

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

Compounds of the present invention are γ-secretase inhibitors. In accordance with the invention compounds of formula I as well as their pharmaceutically acceptable salts are useful in the treatment of illnesses based on the inhibition of the γ-secretase, such as of Alzheimer's disease or common cancers, including, but not limited to, cervical carcinomas and breast carcinomas. In one embodiment, the invention provides a method for treating Alzheimer's disease, which comprises administering to an individual a therapeutically effective amount of a compound of formula I or a pharmaceutically acceptable salt thereof. The invention provides a method of the treatment of cervical carcinomas, which comprises administering to an individual a therapeutically effective amount of a compound of formula I or a pharmaceutically acceptable salt thereof. The invention further provides a method of treating breast carcinomas, which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula IA or IB | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the present invention without limiting it. The examples are compounds which can exist in the form of diastereomeric mixtures, as racemates, or as optically pure compounds.

EXAMPLE 1

2-Methyl-N-((S)-8-oxo-6,7,8,9-tetrahydro-5-oxa-9-aza-benzocyclohepten-7-yl)-N'-(2,2,3,3,3-pentafluoro-propyl)-malonamide

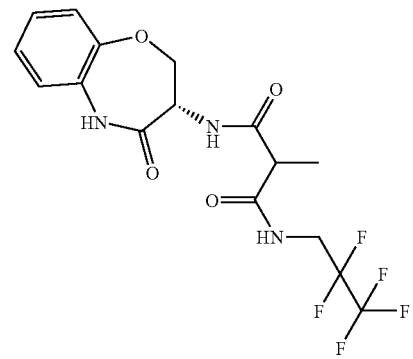

a) 2-Methyl-malonic acid monoethyl ester

To a solution of 6.44 g (115 mmol) potassium hydroxide in 200 ml of ethanol 20.0 g diethyl methyl-malonate (115 mmol) was added and the mixture was refluxed for 4 hours. After cooling the reaction mixture was concentrated by distillation, 50 ml of water were added and the mixture was extracted with ether (two times 50 ml). The aqueous solution was acidified with 4M hydrochloric acid and extracted with ethyl acetate (three times 50 ml). The combined organic layers were dried (MgSO$_4$), concentrated under reduced pressure and used without further purification, MS m/e (%): 101.1 (100), 147.1 (M+H$^+$, 8).

b) 2-Methyl-N-(2,2,3,3,3-pentafluoro-propyl)-malonamic acid ethyl ester

To a solution of 1.56 g (10.6 mmol) methyl-malonic acid monoethyl ester in 20 ml of tetrahydrofuran 1.58 g (10.6 mmol) of 2,2,3,3,3-pentafluoropropylamine, 2.05 g (10.6 mmol) of N-(3-dimethylaminopropyl)-N'-ethylcarbodiimide hydrochloride, 1.44 g (10.6 mmol) of 1-hydroxybenzotrizole hydrate and 2.75 g (21.2 mmol) of N,N-diisopropyl-ethylamine were added.

The mixture was stirred at room temperature for 18 h. The mixture was poured onto 0.5 N HCl (50 ml) and afterwards extracted with dichloromethane (three times 50 ml). The combined organic layers were extracted with 0.5 N aqueous NaHCO$_3$ solution, dried (MgSO$_4$) and the solvent was removed by distillation. The residue was purified by column filtration (hexane/ethyl acetate=2:1) to yield 2.38 g (81%) of the title compound as white crystalline solid, MS m/e (%): 276.1 (M–H$^+$, 100).

c) 2-Methyl-N-(2,2,3,3,3-pentafluoro-propyl)-malonamic acid

To a solution of 1.8 g (6.5 mmol) 2-Methyl-N-(2,2,3,3,3-pentafluoro-propyl)-malonamic acid ethyl ester in 40 ml of tetrahydrofurane, 20 ml of water and 1.09 g (26 mmol) of lithium hydroxide were added and the mixture was stirred overnight at room temperature. After concentration in vacuo water (50 ml) was added and the mixture was extracted with dichloromethane (three times 30 ml). The aqueous phase was acidified with 8 N hydrochloric acid and extracted with dichloromethane (three times 30 ml).

The combined organic layers from the second extraction were dried (MgSO4) and evaporated in vacuo to give 1.62 g (94%) of the title compound as a white solid, MS m/e (%): 247.9 (M–H$^+$, 100).

d) 2-Methyl-N-((S)-8-oxo-6,7,8,9-tetrahydro-5-oxa-9-aza-benzocyclohepten-7-yl)-N'-(2,2,3,3,3-pentafluoro-propyl)-malonamide To a solution of 0.07 g (0.37 mmol) (S)-7-amino-6,7-dihydro-9H-5-oxa-9-aza-benzocyclohepten-8-one in 7 ml tetrahydrofurane were added 0.15 g (0.59 mmol) 2-methyl-N-(2,2,3,3,3-pentafluoro-propyl)-malonamic acid, 0.09 g (0.59 mmol) 1-hydroxybenzotriazole hydrate, 0.12 g (0.59 mmol) N-(3-dimethylaminopropyl)-N'-ethyl-carbodiimidhydrochloride and 1.0 ml (5.9 mmol) diisopropylethylamine. After stirring at room temperature over night the solvent was removed by distillation and the residue was purified by chromatography on silicagel with ethylacetate/heptane (gradient 0–80/100–20) to yield 0.06 g (23%) 2-methyl-N-((S)-8-oxo-6,7,8,9-tetrahydro-5-oxa-9-aza-benzocyclohepten-7-yl)-N'-(2,2,3,3,3-pentafluoro-propyl)-malonamide as light yellow solid, MS m/e (%): 410.3 (M+H$^+$, 100).

EXAMPLE 2

N-((S)-9-Methyl-8-oxo-6,7,8,9-tetrahydro-5-oxa-9-aza-benzocyclohepten-7-yl)-N'-(2,2,3,3,3-pentafluoro-propyl)-malonamide

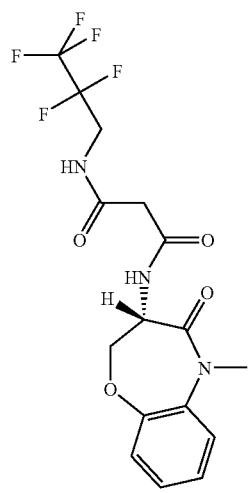

a) N-(2,2,3,3,3-Pentafluoro-propyl)-malonamic acid

N-(2,2,3,3,3-Pentafluoro-propyl)-malonamic acid was obtained in comparable yields according to the procedures described for 2-methyl-N-(2,2,3,3,3-pentafluoro-propyl)-malonamic acid (see example 1) using diethyl malonate instead of diethyl methyl-malonate in step a), MS m/e (%): 234.1 (M–H$^+$, 100).

b) N-((S)-9-Methyl-8-oxo-6,7,8,9-tetrahydro-5-oxa-9-aza-benzocyclohepten-7-yl)-N'-(2,2,3,3,3-pentafluoro-propyl)-malonamide To a solution of 0.06 g (0.31 mmol) (S)-7-amino-9-methyl-6,7-dihydro-9H-5-oxa-9-aza-benzocyclohepten-8-one in 5 ml tetrahydrofurane were added 0.07 g (0.31 mmol) N-(2,2,3,3,3-pentafluoro-propyl)-malonamic acid, 0.04 g (0.31 mmol) 1-hydroxybenzotriazole hydrate, 0.06 g (0.31 mmol) N-(3-dimethylaminopropyl)-N'-ethyl-carbodiimidhydrochloride and 0.1 ml (0.62 mmol) diisopropylethylamine. After stirring at room temperature over night the mixture was added to 1N aqueous hydrochloric acid. Extraction with dichloromethane, followed by washing with saturated aqueous sodium bicarbonate solution and drying with sodium sulfate, and chromatography on silicagel with ethylacetate/heptane yielded 0.05 g (39%) N-((S)-9-methyl-8-oxo-6,7,8,9-tetrahydro-5-oxa-9-aza-benzocyclohepten-7-yl)-N'-(2,2,3,3,3-pentafluoro-propyl)-malonamide as white solid, MS m/e (%): 410.3 (M+H$^+$, 100).

EXAMPLE 3

2-Methyl-N-((S)-9-methyl-8-oxo-6,7,8,9-tetrahydro-5-oxa-9-aza-benzocyclohepten-7-yl)-N'-(2,2,3,3,3-pentafluoro-propyl)-malonamide

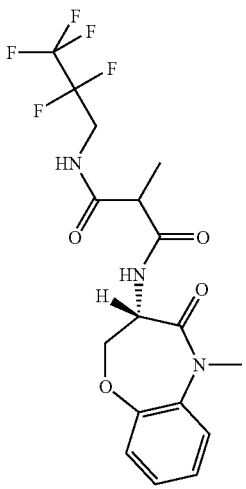

The title compound was obtained in comparable yields according to the procedures described for example 2b using 2-methyl-N-(2,2,3,3,3-pentafluoro-propyl)-malonamic acid instead of N-(2,2,3,3,3-pentafluoro-propyl)-malonamic acid, MS m/e (%): 424.4 (M+H$^+$, 100).

EXAMPLE 4

2,2-Dimethyl-N-((S)-9-methyl-8-oxo-6,7,8,9-tetrahydro-5-oxa-9-aza-benzocyclohepten-7-yl)-N'-(2,2,3,3,3-pentafluoro-propyl)-malonamide

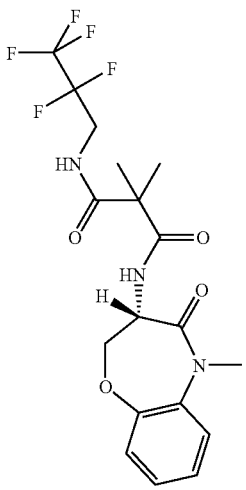

a) 2,2-Dimethyl-N-(2,2,3,3,3-pentafluoro-propyl)-malonamic acid 2,2-Dimethyl-N-(2,2,3,3,3-pentafluoro-propyl)-malonamic acid was obtained in comparable yields according to the procedures described for 2-methyl-N-(2,2,3,3,3-pentafluoro-propyl)-malonamic acid (see example 1) using diethyl dimethyl-malonate instead of diethyl methyl-malonate in step a), MS m/e (%): 262.1 (M–H$^+$, 100).

b) 2,2-Dimethyl-N-((S)-9-methyl-8-oxo-6,7,8,9-tetrahydro-5-oxa-9-aza-benzocyclohepten-7-yl)-N'-(2,2,3,3,3-pentafluoro-propyl)-malonamide The title compound was obtained in comparable yields according to the procedures described for example 2b using 2,2-dimethyl-N-(2,2,3,3,3-pentafluoro-propyl)-malonamic acid instead of N-(2,2,3,3,3-pentafluoro-propyl)-malonamic acid, MS m/e (%): 436.5 (M–H$^+$, 100).

EXAMPLE 5

N-((S)-2-Fluoro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide

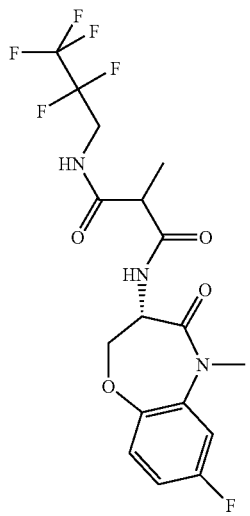

a) (S)-2-tert-Butoxycarbonylamino-3-(4-fluoro-2-nitro-phenoxy)-propionic acid 5.00 g (24.4 mmol) (S)-2-tert-Butoxycarbonylamino-3-hydroxy-propionic acid in 5 ml dimethylformamide were added to a suspension of 2.25 g (51.7 mmol) sodium hydride (55%) in 5 ml dimethylformamide at 0° C. The suspension was stirred for 1 hour and then 4.5 ml (26.8 mmol) 2,5-difluoro-nitrobenzene was added. After additional 3 hours of stirring at 0° C. the mixture was poured on ice/water. The ph was adjusted to 1 by adding 7 ml 25% aqueous hydrochloric acid. Extraction with ethylacetate and chromatography on silicagel with ethylacetate/heptane 1:1 yielded 4.35 g (52%) (S)-2-tert-butoxycarbonylamino-3-(4-fluoro-2-nitro-phenoxy)-propionic acid as yellow solid, MS m/e (%): 343.0 (M–H$^+$, 100).

b) (S)-3-(2-Amino-4-fluoro-phenoxy)-2-tert-butoxycarbonylamino-propionic acid 4.35 g (S)-2-tert-Butoxycarbonylamino-3-(4-fluoro-2-nitro-phenoxy)-propionic acid in 80 ml methanol were hydrogenated with 0.14 g Pd(10%)/C. Chromatography on silicagel with dichloromethane/methanol 9:1 yielded 2.08 g (52%) (S)-3-(2-amino-4-fluoro-phenoxy)-2-tert-butoxycarbonylamino-propionic acid as light brown solid, MS m/e (%): 313.0 (M–H$^+$, 100).

c) ((S)-2-Fluoro-8-oxo-6,7,8,9-tetrahydro-5-oxa-9-aza-benzocyclohepten-7-yl)-carbamic acid tert-butyl ester 1.96 g (6.24 mmol) (S)-3-(2-Amino-4-fluoro-phenoxy)-2-tert-butoxycarbonylamino-propionic acid and 1.20 g (6.24 mmol) N-(3-dimethylaminopropyl)-N'-ethyl-carbodiimid-hydrochloride in 25 ml dimethylformamide were stirred overnight at room temperature. Extraction with water/ethylacetate and removal of the solvent by distillation yielded 1.58 g (86%) ((S)-2-fluoro-8-oxo-6,7,8,9-tetrahydro-5-oxa-9-aza-benzocyclohepten-7-yl)-carbamic acid tert-butyl ester, MS m/e (%): 314 (M+NH$_4^+$, 13), 297 (M+H$^+$, 40), 241 (100), 197 (63).

d) ((S)-2-Fluoro-9-methyl-8-oxo-6,7,8,9-tetrahydro-5-oxa-9-aza-benzocyclohepten-7-yl)-carbamic acid tert-butyl ester To a solution of 1.62 g (5.46 mmol) ((S)-2-Fluoro-8-oxo-6,7,8,9-tetrahydro-5-oxa-9-aza-benzocyclohepten-7-yl)-carbamic acid tert-butyl ester in 20 ml tetrahydrofurane were added at –75° C. 4.57 g (5.46 mmol) lithium bis(trimethylsilyl)amide (20% in tetrahydrofurane) followed after 10 minutes by 0.34 ml (6.55 mmol) methyliodide. Stirring was continued overnight while the mixture was allowed to warm to room temperature. The solvent was removed by distillation and 300 ml saturated aqueous sodium hydrogensulfate solution was added. Extraction with ethylacetate and chromatography on silicagel with ethylacetate/heptane 2:8 yielded 0.87 g (51%) ((S)-2-fluoro-9-methyl-8-oxo-6,7,8,9-tetrahydro-5-oxa-9-aza-benzocyclohepten-7-yl)-carbamic acid tert-butyl ester as white solid, MS m/e (%): 333 (M+Na$^+$, 15), 311 (M+H$^+$, 70), 255 (100).

e) (S)-7-Amino-2-fluoro-9-methyl-6,7-dihydro-9H-5-oxa-9-aza-benzocyclohepten-8-one A solution of 0.85 g (2.74 mmol) ((S)-2-fluoro-9-methyl-8-oxo-6,7,8,9-tetrahydro-5-oxa-9-aza-benzocyclohepten-7-yl)-carbamic acid tert-butyl ester in 20 ml dichloromethane was treated with 21 ml trifluoroacetic acid for 3 hours. Extraction with aqueous sodium bicarbonate solution and dichloromethane and removal of the solvent gave 0.52 g (90%) (S)-7-amino-2-fluoro-9-methyl-6,7-dihydro-9H-5-oxa-9-aza-benzocyclohepten-8-one as white solid, MS m/e (%): 211.3 (M+H$^+$, 100).

f) N-((S)-2-Fluoro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 71% yield according to the procedures described for example 2b using 2-methyl-N-(2,2,3,3,3-pentafluoro-propyl)-malonamic acid and (S)-7-amino-2-fluoro-9-methyl-6,7-dihydro-9H-5-oxa-9-aza-benzocyclohepten-8-one, MS m/e (%): 442.3 (M–H$^+$, 100).

EXAMPLE 6

N-((S)-3-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide

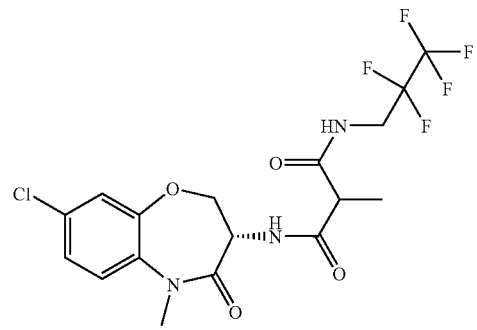

a) (S)-2-tert-Butoxycarbonylamino-3-(5-chloro-2-nitro-phenoxy)-propionic acid

The title compound was obtained in 57% yield according to the procedures described for example 5a using (S)-2-tert-butoxycarbonylamino-3-hydroxy-propionic acid and 4-chloro-2-fluoronitrobenzene, MS m/e (%): 359.0 (M–H$^+$, 100).

b) (S)-3-(2-Amino-5-chloro-phenoxy)-2-tert-butoxycarbonylamino-propionic acid

The title compound was obtained in 50% yield according to the procedures described for example 5b using (S)-2-tert-butoxycarbonylamino-3-(5-chloro-2-nitro-phenoxy)-propionic acid, MS m/e (%): 331.0 (M+H$^+$, 100).

c) ((S)-3-Chloro-8-oxo-6,7,8,9-tetrahydro-5-oxa-9-aza-benzocyclohepten-7-yl)-carbamic acid tert-butyl ester The title compound was obtained in 85% yield according to the procedures described for example 5c using (S)-3-(2-amino-5-chloro-phenoxy)-2-tert-butoxycarbonylamino-propionic acid, MS m/e (%): 311.0 (M–H$^+$, 100).

d) ((S)-3-Chloro-9-methyl-8-oxo-6,7,8,9-tetrahydro-5-oxa-9-aza-benzocyclohepten-7-yl)-carbamic acid tert-butyl ester The title compound was obtained in 65% yield according to the procedures described for example 5d using ((S)-3-chloro-8-oxo-6,7,8,9-tetrahydro-5-oxa-9-aza-benzocyclohepten-7-yl)-carbamic acid tert-butyl ester, MS m/e (%): 327.1 (M+H$^+$, 100).

e) (S)-7-Amino-3-chloro-9-methyl-6,7-dihydro-9H-5-oxa-9-aza-benzocyclohepten-8-one The title compound was obtained in similar yield according to the procedures described for example 5e using ((S)-3-chloro-9-methyl-8-oxo-6,7,8,9-tetrahydro-5-oxa-9-aza-benzocyclohepten-7-yl)-carbamic acid tert-butyl ester, MS m/e (%): 227.3 (M+H$^+$, 100).

f) N-((S)-3-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 66% yield according to the procedures described for example 2b using 2-methyl-N-(2,2,3,3,3-pentafluoro-propyl)-malonamic acid and (S)-7-amino-3-chloro-9-methyl-6,7-dihydro-9H-5-oxa-9-aza-benzocyclohepten-8-one, MS m/e (%): 458.1 (M+H+, 100).

EXAMPLE 7

N-((S)-3,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide

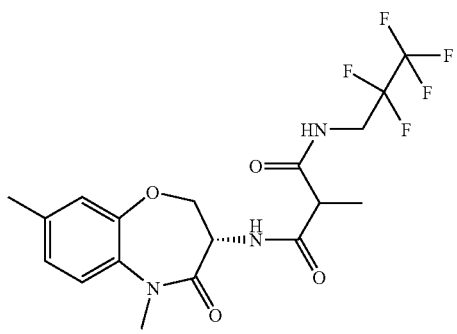

a) (S)-2-tert-Butoxycarbonylamino-3-(5-methyl-2-nitro-phenoxy)-propionic acid

The title compound was obtained in 61% yield according to the procedures described for example 5a using (S)-2-tert-butoxycarbonylamino-3-hydroxy-propionic acid and 3-fluoro-4-nitrotoluene, MS m/e (%): 339.0 (M–H+).

b) (S)-3-(2-Amino-5-methyl-phenoxy)-2-tert-butoxycarbonylamino-propionic acid

The title compound was obtained in 44% yield according to the procedures described for example 5b using (S)-2-tert-butoxycarbonylamino-3-(5-methyl-2-nitro-phenoxy)-propionic acid, MS m/e (%): 311.0 (M+H+, 100).

c) ((S)-3-Methyl-8-oxo-6,7,8,9-tetrahydro-5-oxa-9-aza-benzocyclohepten-7-yl)-carbamic acid tert-butyl ester The title compound was obtained in 38% yield according to the procedures described for example 5c using (S)-3-(2-amino-5-methyl-phenoxy)-2-tert-butoxycarbonylamino-propionic acid, MS m/e: 293.4 (M+H+), 237.1 (M-tBu), 193.1 (M-BOC).

d) ((S)-3,9-Dimethyl-8-oxo-6,7,8,9-tetrahydro-5-oxa-9-aza-benzocyclohepten-7-yl)-carbamic acid tert-butyl ester The title compound was obtained in 76% yield according to the procedures described for example 5d using ((S)-3-methyl-8-oxo-6,7,8,9-tetrahydro-5-oxa-9-aza-benzocyclohepten-7-yl)-carbamic acid tert-butyl ester, MS m/e (%): 307.3 (M+H+, 100).

e) (S)-7-Amino-3,9-dimethyl-6,7-dihydro-9H-5-oxa-9-aza-benzocyclohepten-8-one

The title compound was obtained in 84% yield according to the procedures described for example 5e using ((S)-3,9-dimethyl-8-oxo-6,7,8,9-tetrahydro-5-oxa-9-aza-benzocyclohepten-7-yl)-carbamic acid tert-butyl ester, $^1$H-NMR (ppm, CDCl$_3$): 1.59 (s, 2H), 2.32 (s, 3H), 3.38 (s, 3H), 3.70–3.78 (m, 1H), 4.04–4.14 (m, 1H), 4.35–4.44 (m, 1H), 6.95–7.60 (m, 3H).

f) N-((S)-3,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 90% yield according to the procedures described for example 2b using 2-methyl-N-(2,2,3,3,3-pentafluoro-propyl)-malonamic acid and (S)-7-amino-3,9-dimethyl-6,7-dihydro-9H-5-oxa-9-aza-benzocyclohepten-8-one,
MS m/e (%): 438.3 (M+H+, 100).

EXAMPLE 8a

N-((S)-4-Fluoro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 1 and

EXAMPLE 8b

N-((S)-4-Fluoro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 2

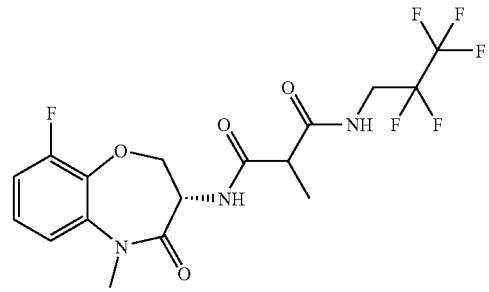

a) (S)-2-tert-Butoxycarbonylamino-3-(2-fluoro-6-nitro-phenoxy)-propionic acid benzyl ester A solution of 3.00 g (19 mmol) 2-fluoro-6-nitrophenole and 7.26 g (28 mmol) triphenylphosphine in 20 ml tetrahydrofurane was treated at −3° C. with 4.34 ml (28 mmol) diethyl azodicarboxylate for 10 minutes. Then 5.44 g (18 mmol) N-tert-butoxycarbonyl-L-serine benzyl ester was added and after stirring at room temperature for 16 hrs the solvent was removed by distillation and the residue was purified by chromatography on silicagel with heptane/ethylacetate (gradient 0–100 to 50:50) to yield 2.40 g (30%) (S)-2-tert-butoxycarbonylamino-3-(2-fluoro-6-nitro-phenoxy)-propionic acid benzyl ester as yellow oil, MS m/e (%): 452.1 (M+NH$_4^+$, 100).

b) (S)-3-(2-Amino-6-fluoro-phenoxy)-2-tert-butoxy-carbonylamino-propionic acid The title compound was obtained in quantitative yield according to the procedures described for example 5b using (S)-2-tert-butoxycarbonylamino-3-(2-fluoro-6-nitro-phenoxy)-propionic acid, MS m/e (%): 314.9 (M+H$^+$, 100).

c) ((S)-4-Fluoro-8-oxo-6,7,8,9-tetrahydro-5-oxa-9-aza-benzocyclohepten-7-yl)-carbamic acid tert-butyl ester The title compound was obtained in 53% yield according to the procedures described for example 5c using (S)-3-(2-amino-6-fluoro-phenoxy)-2-tert-butoxycarbonylamino-propionic acid, MS m/e (%): 297.0 (M+H$^+$, 100).

d) ((S)-4-Fluoro-9-methyl-8-oxo-6,7,8,9-tetrahydro-5-oxa-9-aza-benzocyclohepten-7-yl)-carbamic acid tert-butyl ester The title compound was obtained in 86% yield according to the procedures described for example 5d using ((S)-4-fluoro-8-oxo-6,7,8,9-tetrahydro-5-oxa-9-aza-benzocyclohepten-7-yl)-carbamic acid tert-butyl ester, MS m/e (%): 311.1 (M+H$^+$, 100).

e) (S)-7-Amino-4-fluoro-9-methyl-6,7-dihydro-9H-5-oxa-9-aza-benzocyclohepten-8-one The title compound was obtained in 68% yield according to the procedures described for example 5e using ((S)-4-fluoro-9-methyl-8-oxo-6,7,8,9-tetrahydro-5-oxa-9-aza-benzocyclohepten-7-yl)-carbamic acid tert-butyl ester, MS m/e (%): 210.9 (M+H$^+$, 100).

f) N-((S)-4-Fluoro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 66% yield according to the procedures described for example 2b using 2-methyl-N-(2,2,3,3,3-pentafluoro-propyl)-malonamic acid and (S)-7-amino-4-fluoro-9-methyl-6,7-dihydro-9H-5-oxa-9-aza-benzocyclohepten-8-one. Epimers were obtained by chromatography on silicagel with heptane/ethylacetate, Epimer-1:MS m/e (%): 440.1 (M–H$^+$, 100), [α]589=–131° (0.28% in MeOH), Epimer-2:MS m/e (%): 440.2 (M–H$^+$, 100), [α]589=–161° (0.23% in MeOH).

EXAMPLE 9a

N-((S)-4-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 1 and

EXAMPLE 9b

N-((S)-4-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 2

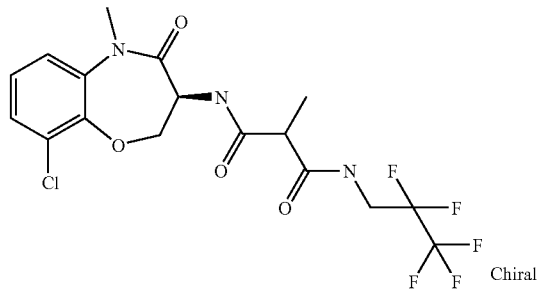

Chiral a) (S)-2-tert-Butoxycarbonylamino-3-(2-chloro-6-nitro-phenoxy)-propionic acid benzyl ester Under an inert atmosphere, a solution of 6.5 g (25 mmol) of triphenylphosphine in 20 ml of tetrahydrofurane was treated with at 0° C. with 3.9 ml (25 mmol) of diethyl azodicarboxylate. Thereupon, 3.0 g (17 mmol) of 2-chloro-6-nitrophenol were added and the reaction mixture was stirred at 0° C. for 15 minutes. Finally, 4.93 g (17 mmol) of (S)-2-tert-butoxycarbonylamino-3-hydroxy-propionic acid benzyl ester were added and the reaction mixture was left to warm to room temperature. After stirring for 18 hours, for the working-up the solvent was evaporated under reduced pressure and the residue triturated in ether at 0° C. The precipitated triphenylphosphinoxide was filtered and washed with ether. The combined filtrates were evaporated to yield 12.8 g of the crude product as a brown-yellow oil. The crude product was purified by chromatography on silica gel using heptane and ethyl acetate as the eluent. There were obtained 3.9 g (50%) of the title compound as a yellow oil, [α]589=–5.96° (c=1.0% in MeOH), MS m/e (%): 468.1 (M+NH$_4^+$, 100).

b) (S)-3-(2-Amino-6-chloro-phenoxy)-2-tert-butoxy-carbonylamino-propionic acid In an analogous manner to that described in example 5b), the hydrogenation of (S)-2-tert-butoxycarbonylamino-3-(2-chloro-6-nitro-phenoxy)-propionic acid benzyl ester using Raney-nickel instead of palladium as the catalyst yielded (91%) the title compound as a light brown foam, MS m/e (%): 329.3 (M–H$^+$, 100).

29 c) ((S)-4-Chloro-8-oxo-6,7,8,9-tetrahydro-5-oxa-9-aza-benzocyclohepten-7-yl)-carbamic acid tert-butyl ester The title compound was obtained in 63% yield according to the procedure described in example 5c) by intramolecular condensation of (S)-3-(2-amino-6-chloro-phenoxy)-2-tert-butoxycarbonylamino-propionic acid as a white solid, $[\alpha]_{589}$=−85.7° (c=1.0% in MeOH), MS m/e (%): 330.0 (M+NH$_4^+$, 100).

d) ((S)-4-Chloro-9-methyl-8-oxo-6,7,8,9-tetrahydro-5-oxa-9-aza-benzocyclohepten-7-yl)-carbamic acid tert-butyl ester The title compound was obtained in 97% yield according to the procedure described in example 5d) by alkylation with methyliodide of ((S)-4-chloro-8-oxo-6,7,8,9-tetrahydro-5-oxa-9-aza-benzocyclohepten-7-yl)-carbamic acid tert-butyl ester as a yellow oil, $[\alpha]_{589}$=−83.2° (c=0.9% in MeOH), MS m/e (%): 327.1 (M+H$^+$, 100).

e) (S)-7-Amino-4-chloro-9-methyl-6,7-dihydro-9H-5-oxa-9-aza-benzocyclohepten-8-one The title compound was obtained in 92% yield according to the procedure described in example 5e) by cleavage of the protecting group of ((S)-4-chloro-9-methyl-8-oxo-6,7,8,9-tetrahydro-5-oxa-9-aza-benzocyclohepten-7-yl)-carbamic acid tert-butyl ester as an off-white solid, $[\alpha]_{589}$=−178.0° (c=1.0% in MeOH), MS m/e (%): 227.1 (M+H$^+$, 100).

f) N-((S)-4-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 1 and N-((S)-4-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 2

The title compounds were obtained according to the procedure described in example 2b) by condensation of (S)-7-amino-4-chloro-9-methyl-6,7-dihydro-9H-5-oxa-9-aza-benzocyclohepten-8-one with 2-methyl-N-(2,2,3,3,3-pentafluoro-propyl)-malonamic acid (ex 1c).

The separation of the two isomers was performed by flash-chromatography on silica gel using a gradient of a 100%:0%- to 0%:100%-mixture of heptane and ethyl acetate as the eluent. There were obtained 19% of theory of the first eluting isomer as a colourless foam, $[\alpha]_{589}$=−29.5° (c=0.4% in MeOH), MS m/e (%): 456.3 (M−H$^+$, 100), and 7% of the later eluting isomer as a colourless foam, $[\alpha]_{589}$=−53.6° (c=0.2% in MeOH), MS m/e (%): 456.4 (M−H$^+$, 100).

30

EXAMPLE 10a

N-((S)-4,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 1 and

EXAMPLE 10b

N-((S)-4,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 2

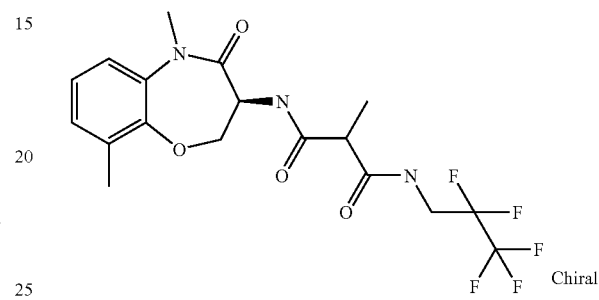

a) (S)-2,2-Dioxo-2λ$^6$-[1,2,3]oxathiazolidine-3,4-dicarboxylic acid 4-benzyl ester 3-tert-butyl In an inert atmosphere and under exclusion of moisture, at 0° C. a solution of 6.9 g (102 mmol) of imidazol in 80 ml of dichloromethane was treated dropwise within 15 minutes with a solution of 2.2 ml (30 mmol) of thionylchloride in 30 ml of dichloromethane. After complete addition, the reaction mixture was left to warm to room temperature and stirring was continued for 30 minutes. Thereafter, a solution of 5.0 g (17 mmol) of (S)-2-tert-butoxycarbonylamino-3-hydroxy-propionic acid benzyl ester in 20 ml of dichloromethane was added dropwise at −78° C. After 1 hour at −78° C., the reaction mixture was left to warm to room temperature and stirring was continued overnight. For the working-up, the reaction mixture was quenched with 150 ml of a solution (10%) of citric acid. The organic layer was separated, washed with water, dried over sodium sulfate, and evaporated. The crude product (5.5 g of a colourless oil) was dissolved in 50 ml of ethyl acetate and cooled to 0° C. Thereafter, an aqueous solution (10%) of 9.0 g (29 mmol) of sodium metaperiodate, cooled to 0° C., and 0.36 g (2 mmol) of ruthenium(IV)oxide hydrate were added. After stirring at 0° C. for 30 minutes, the organic layer was separated, filtered over Dicalit and silica gel, and, finally, evaporated under reduced pressure. There were obtained 4.0 g (66%) of the (S)-2,2-dioxo-2λ$^6$-[1,2,3]oxathiazolidine-3,4-dicarboxylic acid 4-benzyl ester 3-tert-butyl ester as a grey solid, $[\alpha]_{589}$=−21.51° (c=1.0% in MeOH), MS m/e (%): 356.0 (M−H$^+$, 100).

b) (S)-2-tert-Butoxycarbonylamino-3-(2-methyl-6-nitro-phenoxy)-propionic acid benzyl ester In an inert atmosphere and under exclusion of moisture, at 0° C. a solution of 1.5 g (10 mmol) of 2-methyl-6-nitro-phenol [Ger.Offen. 3536192] in 30 ml of N,N-dimethylformamide was treated portionwise with 0.42 g (18 mmol) of sodium hydride (55% dispersion in mineral oil). After complete addition, stirring was continued for 1 hour at 0° C.

Thereafter, 3.85 g (11 mmol) of (S)-2,2-dioxo-2λ⁶-[1,2,3]oxathiazolidine-3,4-dicarboxylic acid 4-benzyl ester 3-tert-butyl ester was added and stirring continued at 0° C. for 3 hours, then at room temperature overnight. For the working-up, the solvent was evaporated under reduced pressure, the residue treated with 100 ml of hydrochloric acid (1 N), then extracted 3 times with 150 ml of ethyl acetate. The crude product (4.0 g) was obtained as a dark brown oil which was purified by flash-chromatography on silica gel using a gradient of a 100%:0%- to 50%:50%-mixture of heptane and ethyl acetate as the eluent. There were obtained 1.4 g (33%) of the title compound as an yellow oil, $[\alpha]_{589}$=−1.45° (c=1.0% in MeOH), MS m/e (%): 431.4 (M+H⁺, 13).

c) (S)-3-(2-Amino-6-methyl-phenoxy)-2-tert-butoxycarbonylamino-propionic acid

The title compound was obtained in 93% yield according to the procedure described in example 5b) by hydrogenation of (S)-2-tert-butoxycarbonylamino-3-(2-methyl-6-nitro-phenoxy)-propionic acid benzyl ester as a light brown foam, $[\alpha]_{589}$=−7.63° (c=1.0% in MeOH), MS m/e (%): 309.3 (M−H⁺, 100).

d) ((S)-4-Methyl-8-oxo-6,7,8,9-tetrahydro-5-oxa-9-aza-benzocyclohepten-7-yl)-carbamic acid tert-butyl ester The title compound was obtained in 73% yield according to the procedure described in example 5c) by intramolecular condensation of (S)-3-(2-amino-6-methyl-phenoxy)-2-tert-butoxycarbonylamino-propionic acid as a white solid, $[\alpha]_{589}$=−137.82° (c=0.792% in MeOH), m.p.: 179° C., MS m/e (%): 293.3 (M+H⁺, 100).

e) ((S)-4,9-Dimethyl-8-oxo-6,7,8,9-tetrahydro-5-oxa-9-aza-benzocyclohepten-7-yl)-carbamic acid tert-butyl ester The title compound was obtained in 28% yield according to the procedure described in example 5d) by alkylation with methyliodide of ((S)-4-methyl-8-oxo-6,7,8,9-tetrahydro-5-oxa-9-aza-benzocyclohepten-7-yl)-carbamic acid tert-butyl ester as a viscous brown oil, $[\alpha]_{589}$=−83.36° (c=0.615% in MeOH), MS m/e (%): 307.3 (M+H⁺, 65).

f) (S)-7-Amino-4,9-dimethyl-6,7-dihydro-9H-5-oxa-9-aza-benzocyclohepten-8-one

The title compound was obtained in quantitative yield according to the procedure described in example 5e) by cleavage of the protecting group of ((S)-4,9-dimethyl-8-oxo-6,7,8,9-tetrahydro-5-oxa-9-aza-benzocyclohepten-7-yl)-carbamic acid tert-butyl ester as a viscous brown oil, $[\alpha]_{589}$=−148.44° (c=0.754% in MeOH), MS m/e (%): 207.2 (M+H⁺, 100).

g) N-((S)-4,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 1 and N-((S)-4,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide-epimer 2

The title compounds were obtained according to the procedure described in example 2b) by condensation of (S)-7-amino-4-chloro-9-methyl-6,7-dihydro-9H-5-oxa-9-aza-benzocyclohepten-8-one with 2-methyl-N-(2,2,3,3,3-pentafluoro-propyl)-malonamic acid [ex 1c)].

The separation of the two isomers was performed by flash-chromatography on silica gel using a gradient of a 100%:0%- to 50%:50%-mixture of heptane and ethyl acetate as the eluent. There were obtained 21% yield of the first eluting isomer as a white solid, $[\alpha]_{589}$=−58.1° (c=0.269% in MeOH), m.p.: 107° C., MS m/e (%): 496.1 (M+OAc⁻, 100), and 9% yield of the later eluting isomer as a white solid, MS m/e (%): 438.3 (M+H⁺, 100).

EXAMPLE 11a

N-((S)-2-Chloro-9-methyl-8-oxo-4-trifluoromethyl-6,7,8,9-tetrahydro-5-oxa-9-aza-benzocyclohepten-7-yl)-2-methyl-N'-(2,2,3,3,3-pentafluoro-propyl)-malonamide-epimer 1 and EXAMPLE 11b N-((S)-2-Chloro-9-methyl-8-oxo-4-trifluoromethyl-6,7,8,9-tetrahydro-5-oxa-9-aza-benzocyclohepten-7-yl)-2-methyl-N'-(2,2,3,3,3-pentafluoro-propyl)-malonamide-epimer 2

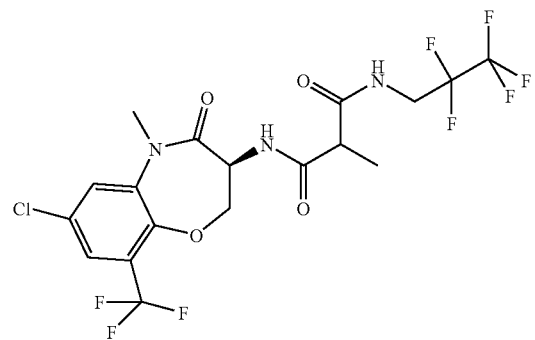

a) (S)-2-tert-Butoxycarbonylamino-3-(4-chloro-2-nitro-6-trifluoromethyl-phenoxy)-propionic acid The title compound was obtained in 54% yield according to the procedures described for example 5a using (S)-2-tert-butoxycarbonylamino-3-hydroxy-propionic acid and 5-chloro-2-fluoro-1-nitro-3-(trifluoromethyl)-benzene, MS m/e (%): 446.0 (M+NH₄⁺, 100).

b) (S)-3-(2-Amino-4-chloro-6-trifluoromethyl-phenoxy)-2-tert-butoxycarbonylamino-propionic acid The title compound was obtained in 96% yield according to the procedures described for example 5b using (S)-2-tert-butoxycarbonylamino-3-(4-chloro-2-nitro-6-trifluoromethyl-phenoxy)-propionic acid, MS m/e (%): 397.3 (M−H⁺, 100).

c) ((S)-2-Chloro-8-oxo-4-trifluoromethyl-6,7,8,9-tetrahydro-5-oxa-9-aza-benzocyclohepten-7-yl)-carbamic acid tert-butyl ester The title compound was obtained in 62% yield according to the procedures described for example 5c using (S)-3-(2-amino-4-chloro-6-trifluoromethyl-phenoxy)-2-tert-butoxycarbonyl-amino-propionic acid, MS m/e (%): 379.1 (M−H⁺, 100).

d) ((S)-2-Chloro-9-methyl-8-oxo-4-trifluoromethyl-6,7,8,9-tetrahydro-5-oxa-9-aza-benzocyclohepten-7-yl)-carbamic acid tert-butyl ester The title compound was obtained in 65% yield according to the procedures described for example 5d using ((S)-2-chloro-8-oxo-4-trifluoromethyl-6,7,8,9-tetrahydro-5-oxa-9-aza-benzocyclohepten-7-yl)-carbamic acid tert-butyl ester, MS m/e (%): 395.0 (M+H$^+$, 100).

e) (S)-7-Amino-2-chloro-9-methyl-4-trifluoromethyl-6,7-dihydro-9H-5-oxa-9-aza-benzocyclohepten-8-one The title compound was obtained in 74% yield according to the procedures described for example 5e using ((S)-2-chloro-9-methyl-8-oxo-4-trifluoromethyl-6,7,8,9-tetrahydro-5-oxa-9-aza-benzocyclohepten-7-yl)-carbamic acid tert-butyl ester, MS m/e (%): 295.1 (M+H$^+$, 100).

f) N-((S)-2-Chloro-9-methyl-8-oxo-4-trifluoromethyl-6,7,8,9-tetrahydro-5-oxa-9-aza-benzocyclohepten-7-yl)-2-methyl-N'-(2,2,3,3,3-pentafluoro-propyl)-malonamide-epimer 1 and N-((S)-2-Chloro-9-methyl-8-oxo-4-trifluoromethyl-6,7,8,9-tetrahydro-5-oxa-9-aza-benzocyclohepten-7-yl)-2-methyl-N'-(2,2,3,3,3-pentafluoro-propyl)-malonamide-epimer 2

N-((S)-2-Chloro-9-methyl-8-oxo-4-trifluoromethyl-6,7,8,9-tetrahydro-5-oxa-9-aza-benzocyclohepten-7-yl)-2-methyl-N'-(2,2,3,3,3-pentafluoro-propyl)-malonamide was obtained in 75% yield according to the procedures described for example 2b using 2-methyl-N-(2,2,3,3,3-pentafluoro-propyl)-malonamic acid and (S)-7-amino-2-chloro-9-methyl-4-trifluoromethyl-6,7-dihydro-9H-5-oxa-9-aza-benzocyclohepten-8-one. Epimers were obtained by chromatography on silicagel with heptane/ethylacetate, Epimer-1:MS m/e (%): 523.8 (M−H$^+$, 100), Epimer-2:MS m/e (%): 523.8 (M−H$^+$, 100).

EXAMPLE 12a

2-Methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide-epimer 1 and

EXAMPLE 12b

2-Methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide-epimer 2

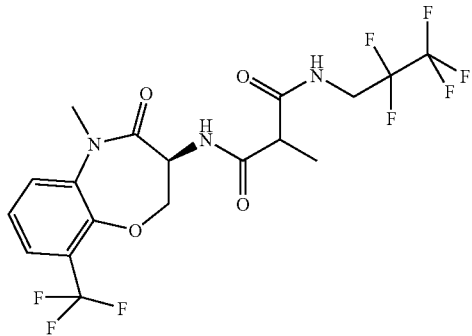

a) 5-Bromo-2-fluoro-1-nitro-3-trifluoromethyl-benzene and 1-Bromo-4-fluoro-2-nitro-5-trifluoromethyl-benzene 12.2 g (49 mmol) 5-bromo-2-fluorobenzotrifluoride were added at 15° C. to a mixture of 3.06 ml (73 mmol) nitric acid (99.5%) in 29.4 ml fuming sulfuric acid. The temperature increased to 30° C. The heterogeneous mixture was stirred vigorously for 4 hours and then poured on a mixture of ice/water. The organic material was extracted with diethylether. The organic phase was washed with saturated aqueous sodium hydrogencarbonate solution. Chromatography on silicagel with ethylacetate/heptane 1/10 yielded 9.70 g of a 2/1 mixture of 5-bromo-2-fluoro-1-nitro-3-trifluoromethyl-benzene and 1-bromo-4-fluoro-2-nitro-5-trifluoromethyl-benzene. A small sample was separated on silicagel with ethylacetate/heptane 1/19. 5-Bromo-2-fluoro-1-nitro-3-trifluoromethyl-benzene, $^1$H-NMR (ppm, CDCl$_3$): 8.010–8.038 (m, 1H) and 8.368–8.390 (m, 1H); MS m/e (%): 288.8 (79), 286.9 (78), 242.9 (19), 240.0 (22), 161.9 (100). 1-Bromo-4-fluoro-2-nitro-5-trifluoromethyl-benzene, 1H-NMR (ppm, CDCl$_3$): δ 7.709–7.731 (m, 1H) and 8.008–8.024 (m, 1H); MS m/e (%): 289 (48), 286.8 (50), 242.8 (27), 240.8 (30), 161.9 (100).

b) (S)-3-(4-Bromo-2-nitro-6-trifluoromethyl-phenoxy)-2-tert-butoxycarbonylamino-propionic acid The title compound was obtained in 64% yield according to the procedures described for example 5a using (S)-2-tert-butoxycarbonylamino-3-hydroxy-propionic acid and 5-bromo-2-fluoro-1-nitro-3-(trifluoromethyl)-benzene (2/1 mixture with 1-bromo-2-fluoro-1-nitro-3-(trifluoromethyl)-benzene), MS m/e (%): 490.1 and 492.2 (M+NH$_4^+$, 100).

c) (S)-3-(2-Amino-6-trifluoromethyl-phenoxy)-2-tert-butoxycarbonylamino-propionic acid The title compound was obtained in quantitative yield according to the procedures described for example 5b using (S)-3-(4-bromo-2-nitro-6-trifluoromethyl-phenoxy)-2-tert-butoxycarbonyl-amino-propionic acid, MS m/e (%): 365.1 (M+H$^+$, 100).

d) ((S)-8-Oxo-4-trifluoromethyl-6,7,8,9-tetrahydro-5-oxa-9-aza-benzocyclohepten-7-yl)-carbamic acid tert-butyl ester The title compound was obtained in 62% yield according to the procedures described for example 5c using (S)-3-(2-amino-6-trifluoromethyl-phenoxy)-2-tert-butoxycarbony-lamino-propionic acid, MS m/e (%): 347.4 (M+H$^+$, 56), 291.0 (100), 247.1 (32).

e) ((S)-9-Methyl-8-oxo-4-trifluoromethyl-6,7,8,9-tetrahydro-5-oxa-9-aza-benzocyclohepten-7-yl)-carbamic acid tert-butyl ester The title compound was obtained in 79% yield according to the procedures described for example 5d using ((S)-8-oxo-4-trifluoromethyl-6,7,8,9-tetrahydro-5-oxa-9-aza-benzocyclohepten-7-yl)-carbamic acid tert-butyl ester, MS m/e (%): 721.5 (2M+H$^+$, 100).

f) (S)-7-Amino-9-methyl-4-trifluoromethyl-6,7-dihydro-9H-5-oxa-9-aza-benzocyclohepten-8-one The title compound was obtained in 73% yield according to the procedures described for example 5e using ((S)-9-methyl-8-oxo-4-trifluoromethyl-6,7,8,9-tetrahydro-5-oxa-9-aza-benzocyclohepten-7-yl)-carbamic acid tert-butyl ester, MS m/e (%): 261.1 (M+H+, 100).

g) 2-Methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide-epimer 1 and 2-Methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide-epimer 2

2-Methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide was obtained in 77% yield according to the procedures described for example 2b using 2-methyl-N-(2,2,3,3,3-pentafluoro-propyl)-malonamic acid and (S)-7-amino-9-methyl-4-trifluoromethyl-6,7-dihydro-1 9H-5-oxa-9-aza-benzocyclohepten-8-one. Epimers were obtained by chromatography on silicagel with heptane/ethylacetate, Epimer-1:MS m/e (%): 492.1 (M+H+, 100), Epimer-2:MS m/e (%): 492.1 (M+H+, 100).

EXAMPLE 13

N-((S)-2-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide

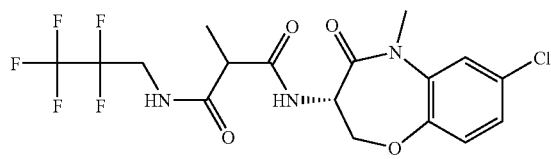

a) (S)-2-tert-Butoxycarbonylamino-3-(4-chloro-2-nitro-phenoxy)-propionic acid

The title compound was obtained in 38% yield according to the procedures described for example 5a using (S)-2-tert-butoxycarbonylamino-3-hydroxy-propionic acid and 5-chloro-2-fluoronitrobenzene, MS m/e (%): 359.1 (M–H+, 100).

b) (S)-3-(2-Amino-4-chloro-phenoxy)-2-tert-butoxycarbonylamino-propionic acid

The title compound was obtained in 69% yield according to the procedures described for example 5b using (S)-2-tert-butoxycarbonylamino-3-(4-chloro-2-nitro-phenoxy)-propionic acid, MS m/e (%): 331.1 (M+H+, 100).

c) ((S)-2-Chloro-8-oxo-6,7,8,9-tetrahydro-5-oxa-9-aza-benzocyclohepten-7-yl)-carbamic acid tert-butyl ester The title compound was obtained in 15% yield according to the procedures described for example 5c using (S)-3-(2-amino-4-chloro-phenoxy)-2-tert-butoxycarbonylamino-propionic acid, MS m/e: 311.0 (M–H+).

d) ((S)-2-Chloro-9-methyl-8-oxo-6,7,8,9-tetrahydro-5-oxa-9-aza-benzocyclohepten-7-yl)-carbamic acid tert-butyl ester The title compound was obtained in 32% yield according to the procedures described for example 5d using ((S)-2-chloro-8-oxo-6,7,8,9-tetrahydro-5-oxa-9-aza-benzocyclohepten-7-yl)-carbamic acid tert-butyl ester, MS m/e (%): 327.1 (M+H+, 100).

e) (S)-7-Amino-2-chloro-9-methyl-6,7-dihydro-9H-5-oxa-9-aza-benzocyclohepten-8-one The title compound was obtained in 86% yield according to the procedures described for example 5e using ((S)-2-chloro-9-methyl-8-oxo-6,7,8,9-tetrahydro-5-oxa-9-aza-benzocyclohepten-7-yl)-carbamic acid tert-butyl ester, MS n/e (%): 227.0 (M+H+, 100).

f) N-((S)-2-Chloro-9-methyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 84% yield according to the procedures described for example 2b using 2-methyl-N-(2,2,3,3,3-pentafluoro-propyl)-malonamic acid and (S)-7-amino-2-chloro-9-methyl-6,7-dihydro-9H-5-oxa-9-aza-benzocyclohepten-8-one, MS m/e (%): 458.0 (M+H+, 100).

EXAMPLE 14

N-((S)-9-Ethyl-8-oxo-6,7,8,9-tetrahydro-5-oxa-9-aza-benzocyclohepten-7-yl)-2-methyl-N'-(2,2,3,3,3-pentafluoro-propyl)-malonamide

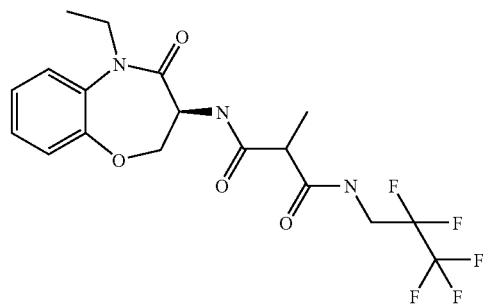

a) ((S)-9-Ethyl-8-oxo-6,7,8,9-tetrahydro-5-oxa-9-aza-benzocyclohepten-7-yl)-carbamic acid tert-butyl ester In an analogous manner to that described in example 5d), the alkylation by iodoethane of (S)-(8-oxo-6,7,8,9-tetrahydro-5-oxa-9-aza-benzocyclohepten-7-yl)-carbamic acid tert-butyl ester [Chem.Pharm.Bull. 1986, 34(3), 1128–47] yielded (87% of theory) the title compound as a white solid, m.p.: 112° C., MS m/e (%): 307.1 (M+H+, 93).

b) (S)-7-Amino-9-ethyl-6,7-dihydro-9H-5-oxa-9-aza-benzocyclohepten-8-one

The title compound was obtained in 36% yield according to the procedure described in example 5e) by cleavage of the protecting group of ((S)-9-ethyl-8-oxo-6,7,8,9-tetrahydro-5-oxa-9-aza-benzocyclohepten-7-yl)-carbamic acid tert-butyl ester as a white solid, m.p.: 97° C., MS m/e (%): 207.3 (M+H+, 72).

c) N-((S)-9-Ethyl-8-oxo-6,7,8,9-tetrahydro-5-oxa-9-aza-benzocyclohepten-7-yl)-2-methyl-N-(2,2,3,3,3-pentafluoro-propyl)-malonamide The title compound was obtained in 74% yield according to the procedure described in example 2b) by condensation of (S)-7-amino-9-ethyl-6,7-dihydro-9H-5-oxa-9-aza-benzocyclohepten-8-one with 2-methyl-N-(2,2,3,3,3-pentafluoro-propyl)-malonamic acid [ex 1c)], m.p.: 152° C., MS m/e (%): 438.3 (M+H+, 100).

EXAMPLE 15

N-(3,5-Difluoro-benzyl)-2-methyl-N'-((6R,7S)-6-methyl-8-oxo-6,7,8,9-tetrahydro-5-oxa-9-aza-benzocyclohepten-7-yl)-malonamide

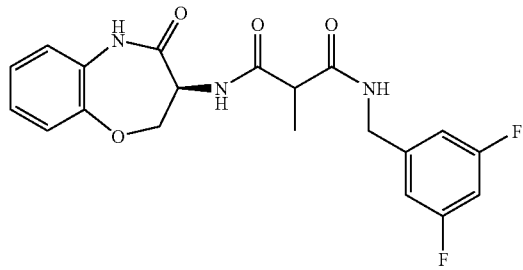

a) (2S,3R)-2-tert-Butoxycarbonylamino-3-(2-nitro-phenoxy)-butyric acid

The title compound was obtained in 73% yield according to the procedures described for example 5a using N-tert-butoxycarbonyl-L-threonine and 1-fluoro-2-nitrobenzene, MS m/e (%): 339.3 (M–H+, 100).

b) (2S,3R)-3-(2-Amino-phenoxy)-2-tert-butoxycarbonylamino-butyric acid

The title compound was obtained in 58% yield according to the procedures described for example 5b using (2S,3R)-2-tert-butoxycarbonylamino-3-(2-nitro-phenoxy)-butyric acid, MS m/e (%): 311 (M+H+, 81), 255 (100), 211 (71).

c) ((6R,7S)-6-Methyl-8-oxo-6,7,8,9-tetrahydro-5-oxa-9-aza-benzocyclohepten-7-yl)-carbamic acid tert-butyl ester The title compound was obtained in 32% yield according to the procedures described for example 5c using (2S,3R)-3-(2-amino-phenoxy)-2-tert-butoxycarbonylamino-butyric acid, MS m/e (%): 293.1 (M+H+, 26), 236.9 (100), 192.8 (90).

d) (6R,7S)-7-Amino-6-methyl-6,7-dihydro-9H-5-oxa-9-aza-benzocyclohepten-8-one The title compound was obtained in 20% yield according to the procedures described for example 5e using ((6R,7S)-6-methyl-8-oxo-6,7,8,9-tetrahydro-5-oxa-9-aza-benzocyclohepten-7-yl)-carbamic acid tert-butyl ester, MS m/e (%): 193.3 (M+H+, 100).

e) N-(3,5-Difluoro-benzyl)-2-methyl-N'-((6R,7S)-6-methyl-8-oxo-6,7,8,9-tetrahydro-5-oxa-9-aza-benzocyclohepten-7-yl)-malonamide The title compound was obtained in 83% yield according to the procedures described for example 2b using N-(3,5-difluoro-benzyl)-2-methyl-malonamic acid and (6R,7S)-7-amino-6-methyl-6,7-dihydro-9H-5-oxa-9-aza-benzocyclohepten-8-one, MS m/e (%): 418.3 (M+H+, 100).

EXAMPLE 16

N-(3,5-Difluoro-benzyl)-2-[1,3] dioxolan-2-ylmethyl-N'-((6R,7S)-6-methyl-8-oxo-6,7,8,9-tetrahydro-5-oxa-9-aza-benzocyclohepten-7-yl)-malonamide

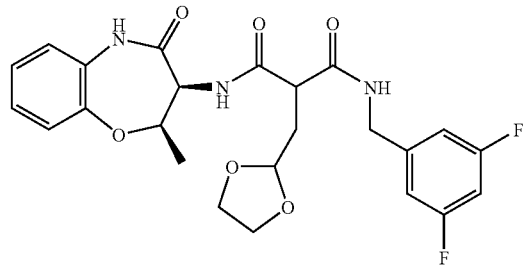

a) 2-[1,3]Dioxolan-2-ylmethyl-malonic acid monomethyl ester

To a solution of 1.03 g (18 mmol) potassium hydroxide in 15 ml methanol were added 4.00 g (18 mmol) (1,3-dioxolan-2-ylmethyl)propanedioic acid dimethyl ester. After stirring overnight at 85° C. the solvent was distilled off. The residue was extracted with water/ethylacetate. The aqueous phase was then acidified with concentrated hydrochloric acid. Extraction with ethylacetate gave 2.11 g (56%) 2-[1,3] dioxolan-2-ylmethyl-malonic acid monomethyl ester as light yellow oil, $^1$H-NMR (ppm, CDCl$_3$) δ 2.38–2.42 (m, 2H), 3.65 (t, 1H, J=6.9 Hz), 3.77 (s, 3H), 3.79–3.97 (m, 4H), 5.03 (t, 1H, J=3.6 Hz).

b) N-(3,5-Difluoro-benzyl)-2-[1,3]dioxolan-2-ylmethyl-malonamic acid methyl ester The title compound was obtained in 64% yield according to the procedures described for example 1b using 2-[1,3] dioxolan-2-ylmethyl-malonic acid monomethyl ester and 3,5-difluorobenzylamine, $^1$H-NMR (ppm, CDCl$_3$) δ

2.37–2.41 (m, 2H), 3.51 (t, 1H, J=6.8 Hz), 3.76 (s, 3H), 3.84–3.95 (m, 4H), 4.42–4.47 (m, 2H), 4.97 (t, 1H, J=4.0 Hz), 6.67–6.83 (m, 3H).

c) N-(3,5-Difluoro-benzyl)-2-[1,3]dioxolan-2-ylmethyl-malonamic acid

The title compound was obtained in 90% yield according to the procedures described for example 1c using N-(3,5-difluoro-benzyl)-2-[1,3]dioxolan-2-ylmethyl-malonamic acid methyl ester, NMR (ppm, DMSO-$d_6$) δ 2.05–2.08 (m, 2H), 3.43 (t, 1H, J=6.9 Hz), 3.73–3.90 (m, 4H), 4.27–4.36 (m, 2H), 4.79 (t, 1H, J=4.6 Hz), 6.98–7.12 (m, 3H), 8.75 (t, 1H, J=6.0 Hz), 12.71 (s, broad, 1H).

d) N-(3,5-Difluoro-benzyl)-2-[1,3]dioxolan-2-ylmethyl-N'-((6R,7S)-6-methyl-8-oxo-6,7,8,9-tetrahydro-5-oxa-9-aza-benzocyclohepten-7-yl)-malonamide The title compound was obtained in 60% yield according to the procedures described for example 2b using N-(3,5-difluoro-benzyl)-2-[1,3]dioxolan-2-ylmethyl-malonamic acid and (6R,7S)-7-amino-6-methyl-6,7-dihydro-9H-5-oxa-9-aza-benzocyclohepten-8-one, MS m/e (%): 490.5 (M+H$^+$, 100).

EXAMPLE 17

N-(3,5-Difluoro-benzyl)-2-fluoro-N'-((6R,7S)-6-methyl-8-oxo-6,7,8,9-tetrahydro-5-oxa-9-aza-benzocyclohepten-7-yl)-2-propyl-malonamide

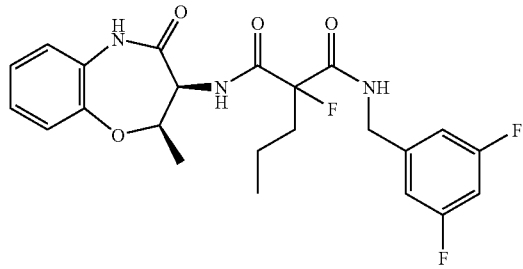

a) 2-Fluoro-2-propyl-malonic acid monoethyl ester

The title compound was obtained in 64% yield according to the procedures described for example 1a using fluoropropyl-propanedioic acid diethyl ester, $^1$H-NMR (ppm, CDCl$_3$) δ 0.98 (t, 3H, J=7.4 Hz), 1.34 (t, 3H, J=7.1 Hz), 1.46–1.51 (m, 2H), 2.10–2.24 (m, 2H), 4.33 (q, 2H, J=7.1 Hz).

b) 2-(3,5-Difluoro-benzylcarbamoyl)-2-fluoro-pentanoic acid ethyl ester

The title compound was obtained in 49% yield according to the procedures described for example 1b using 2-fluoro-2-propyl-malonic acid monoethyl ester and 3,5-difluorobenzylamine, $^1$H-NMR (ppm, CDCl$_3$) δ 0.97 (t, 3H, J=7.4 Hz), 1.32 (t, 3H, J=7.1 Hz), 1.34–1.53 (m, 2H), 4.25–4.34 (m, 2H), 4.38–4.58 (m, 2H), 6.69–6.85 (m, 4H).

c) 2-(3,5-Difluoro-benzylcarbamoyl)-2-fluoro-pentanoic acid

The title compound was obtained in 70% yield according to the procedures described for example 1c using 2-(3,5-difluoro-benzylcarbamoyl)-2-fluoro-pentanoic acid ethyl ester, $^1$H-NMR (ppm, DMSO-$d_6$) δ 0.89 (t, 3H, J=7.4 Hz), 1.90–2.10 (m, 2H), 4.24–4.40 (m, 2H), 6.91–6.96 (m, 2H), 7.07–7.13 (m, 1H), 9.02 (t, broad, 1H), 13.79 (s, broad, 1H).

d) N-(3,5-Difluoro-benzyl)-2-fluoro-N'-((6R,7S)-6-methyl-8-oxo-6,7,8,9-tetrahydro-5-oxa-9-aza-benzocyclohepten-7-yl)-2-propyl-malonamide The title compound was obtained in 66% yield according to the procedures described for example 2b using 2-(3,5-difluoro-benzylcarbamoyl)-2-fluoro-pentanoic acid and (6R,7S)-7-amino-6-methyl-6,7-dihydro-9H-5-oxa-9-aza-benzocyclohepten-8-one, MS m/e (%): 464.2 (M+H$^+$, 100).

EXAMPLE 18

2-Methyl-N-((6R,7S)-6-methyl-8-oxo-6,7,8,9-tetrahydro-5-oxa-9-aza-benzocyclohepten-7-yl)-N'-(2,2,3,3,3-pentafluoro-propyl)-malonamide

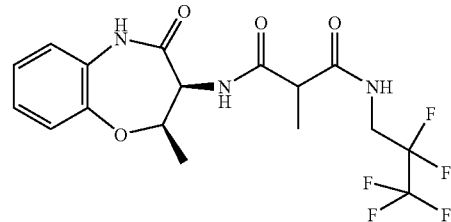

The title compound was obtained in 82% yield according to the procedures described for example 2b using 2-methyl-N-(2,2,3,3,3-pentafluoro-propyl)-malonamic acid and (6R,7S)-7-amino-6-methyl-6,7-dihydro-9H-5-oxa-9-aza-benzocyclohepten-8-one, MS m/e (%): 424.3 (M+H$^+$, 100).

EXAMPLE 19

2,2-Dimethyl-N-((6R,7S)-6-methyl-8-oxo-6,7,8,9-tetrahydro-5-oxa-9-aza-benzocyclohepten-7yl)-N'-(2,2,3,3,3-pentafluoro-propyl)-malonamide

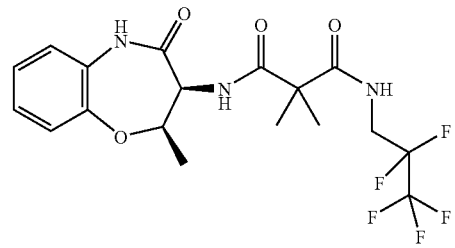

The title compound was obtained in 60% yield according to the procedures described for example 2b using 2,2-dimethyl-N-(2,2,3,3,3-pentafluoro-propyl)-malonamic acid and (6R,7S)-7-amino-6-methyl-6,7-dihydro-9H-5-oxa-9-aza-benzocyclohepten-8-one, MS m/e (%): 238.3 (M+H$^+$, 100).

EXAMPLE 20

2-Methyl-N-((6S,7S)-6-methyl-8-oxo-6,7,8,9-tetrahydro-5-oxa-9-aza-benzocyclohepten-7-yl)-N'-(2,2,3,3,3-pentafluoro-propyl)-malonamide

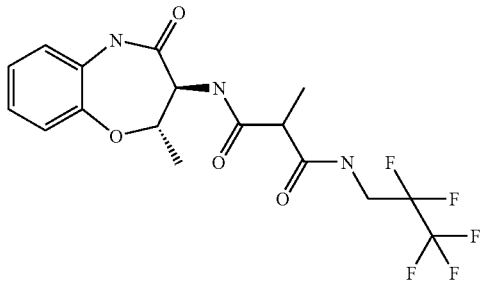

a) (6S,7S)-7-Amino-6-methyl-6,7-dihydro-9H-5-oxa-9-aza-benzocyclohepten-8-one In analogy to the reaction sequence for the synthesis of (6R,7S)-7-amino-6-methyl-6,7-dihydro-9H-5-oxa-9-aza-benzocyclohepten-8-one in example 15, the title compound was obtained by starting with L-(+)-allo-threonine instead of L-threonine, MS m/e (%): 193.4 (M+H$^+$, 100).

b) 2-Methyl-N-((6S,7S)-6-methyl-8-oxo-6,7,8,9-tetrahydro-5-oxa-9-aza-benzocyclohepten-7-yl)-N'-(2,2,3,3,3-pentafluoro-propyl)-malonamide The title compound was obtained according to the procedure described in example 2b) by condensation of (6S,7S)-7-amino-6-methyl-6,7-dihydro-9H-5-oxa-9-aza-benzocyclohepten-8-one with 2-methyl-N-(2,2,3,3,3-pentafluoropropyl)-malonamic acid [ex 1c)], MS m/e (%): 424.3 (M+H$^+$, 100).

EXAMPLE 21

N-((6R,7S)-1-Fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

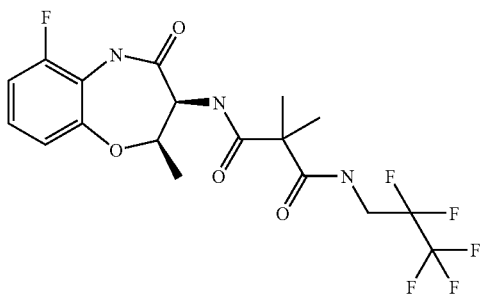

a) (2S,3R)-2-tert-Butoxycarbonylamino-3-(3-fluoro-2-nitro-phenoxy)-butyric acid In analogous manner to that described in example 5a), the reaction of (2S,3R)-2-tert-butoxycarbonylamino-3-hydroxy-butyric acid and 2,6-difluoro-nitrobenzene yielded (78% of theory) the title compound as a brown oil, MS m/e (%): 357.3 (M–H$^+$, 100).

b) (2S,3R)-3-(2-Amino-3-fluoro-phenoxy)-2-tert-butoxycarbonylamino-butyric acid The title compound was obtained in 91% yield according to the procedure described in example 5b) by hydrogenation of (2S,3R)-2-tert-butoxycarbonylamino-3-(3-fluoro-2-nitrophenoxy)-butyric acid as a light brown solid, m.p.: 158–160° C., MS m/e (%): 327.4 (M–H$^+$, 100).

c) ((6R,7S)-Fluoro-6-methyl-8-oxo-6,7,8,9-tetrahydro-5-oxa-9-aza-benzocyclohepten-7-yl)-carbamic acid tert-butyl ester The title compound was obtained in 54% yield according to the procedure described in example 5c) by intramolecular condensation of (2S,3R)-3-(2-amino-3-fluoro-phenoxy)-2-tert-butoxycarbonylamino-butyric acid as a light yellow oil, MS m/e (%): 311.1 (M+H$^+$, 12).

d) (6R,7S)-7-Amino-1-fluoro-6-methyl-6,7-dihydro-9H-5-oxa-9-aza-benzocyclohepten-8-one The title compound was obtained in 69% yield according to the procedure described in example 5e) by cleavage of the protecting group of ((6R,7S)-1-fluoro-6-methyl-8-oxo-6,7,8,9-tetrahydro-5-oxa-9-aza-benzocyclohepten-7-yl)-carbamic acid tert-butyl ester as a white foam, MS m/e (%): 211.1 (M+H$^+$, 100).

e) N-((6R,7S)-1-Fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained in 77% yield according to the procedure described in example 2b) by condensation of (6R,7S)-7-amino-1-fluoro-6-methyl-6,7-dihydro-9H-5-oxa-9-aza-benzocyclohepten-8-one with 2,2-dimethyl-N-(2,2,3,3,3-pentafluoro-propyl)-malonamic acid [ex. 4a)], MS m/e (%): 456.4 (M+H$^+$, 100).

EXAMPLE 22

N-((6R,7S)-1-Fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide

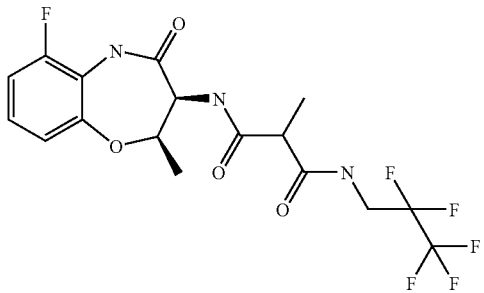

The title compound was obtained in 76% yield according to the procedure described in example 2b) by condensation of (6R,7S)-7-amino-1-fluoro-6-methyl-6,7-dihydro-9H-5-oxa-9-aza-benzocyclohepten-8-one with 2-methyl-N-(2,2,3,3,3-pentafluoro-propyl)-malonamic acid [example 1c)], MS m/e (%): 442.3 (M+H$^+$, 100).

EXAMPLE 23

N-((6R,7S)-2-Fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide

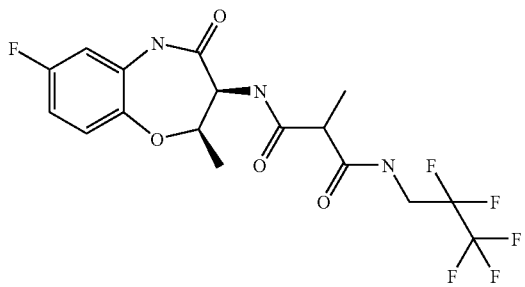

a) (2S,3R)-2-tert-Butoxycarbonylamino-3-(4-fluoro-2-nitro-phenoxy)-butyric acid In analogous manner to that described in example 5a), the reaction of (2S,3R)-2-tert-butoxycarbonylamino-3-hydroxy-butyric acid and 2,5-difluoro-nitrobenzene yielded (72% of theory) the title compound as a brown oil, MS m/e (%): 357.1 (M−H$^+$, 100).

b) (2S,3R)-3-(2-Amino-4-fluoro-phenoxy)-2-tert-butoxycarbonylamino-butyric acid The title compound was obtained in quantitative yield according to the procedure described in example 5b) by hydrogenation of (2S,3R)-2-tert-butoxycarbonylamino-3-(4-fluoro-2-nitro-phenoxy)-butyric acid as a brown foam, MS m/e (%): 329.1 (M+H$^+$, 100).

c) ((6R,7S)-2-Fluoro-6-methyl-8-oxo-6,7,8,9-tetrahydro-5-oxa-9-aza-benzocyclohepten-7-yl)-carbamic acid tert-butyl ester The title compound was obtained in 36% yield according to the procedure described in example 5c) by intramolecular condensation of (2S,3R)-3-(2-amino-4-fluoro-phenoxy)-2-tert-butoxycarbonylamino-butyric acid as a light yellow solid, m.p.: 141–148° C., [α]$_{589}$=−180.47° (c=0.483% in MeOH), MS m/e (%): 311 (M+H$^+$, 38).

d) (6R,7S)-7-Amino-2-fluoro-6-methyl-6,7-dihydro-9H-5-oxa-9-aza-benzocyclohepten-8-one The title compound was obtained in 64% yield according to the procedure described in example 5e) by cleavage of the protecting group of ((6R,7S)-2-fluoro-6-methyl-8-oxo-6,7,8,9-tetrahydro-5-oxa-9-aza-benzocyclohepten-7-yl)-carbamic acid tert-butyl ester as a light brown solid, m.p.: 173–177° C., MS m/e (%): 210.9 (M+H$^+$, 100).

e) N-((6R,7S)-2-Fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 77% yield according to the procedure described in example 2b) by condensation of (6R,7S)-7-amino-2-fluoro-6-methyl-6,7-dihydro-9H-5-oxa-9-aza-benzocyclohepten-8-one with 2-methyl-N-(2,2,3,3,3-pentafluoro-propyl)-malonamic acid [example 1c)] as an off-white solid, m.p.: 215–216° C., MS m/e (%): 442.3 (M+H$^+$, 14).

EXAMPLE 24

N-Butyl-2,2-dimethyl-N'-((6R,7S)-6-methyl-8-oxo-6,7,8,9-tetrahydro-5-oxa-9-aza-benzocyclohepten-7-yl)-malonamide

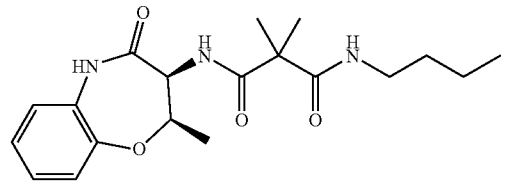

a) N-Butyl-2,2-dimethyl-malonamic acid 1.72 g (10 mmol) 2,2,5,5-Tetramethyl-[1,3]dioxane-4,6-dione and 1.02 ml butylamine were stirred in 7 ml N,N-diisopropyl-ethylamine for 18 hours at room temperature. The excess N,N-diisopropyl-ethylamine was decanted and the residue was extracted with 1N aqueous hydrochloric acid/ethylacetate. The ethylacetate phase was washed with 1N aqueous hydrochloric acid, brine and was dried over sodiumsulfate. Evaporation of the solvent and recrystallisation from dichloromethane/heptane yielded 60% N-butyl-2,2-dimethyl-malonamic acid as white solid, MS m/e (%): 188.4 (M+H$^+$, 100).

b) N-Butyl-2,2-dimethyl-N'-((6R,7S)-6-methyl-8-oxo-6,7,8,9-tetrahydro-5-oxa-9-aza-benzocyclohepten-7-yl)-malonamide The title compound was obtained in 83% yield according to the procedures described for example 2b using N-butyl-2,2-dimethyl-malonamic acid and (6R,7S)-7-amino-6-methyl-6,7-dihydro-9H-5-oxa-9-aza-benzocyclohepten-8-one, MS m/e (%): 362.3 (M+H+, 100).

EXAMPLE 25

2,2-Dimethyl-N-((6R,7S)-6-methyl-8-oxo-6,7,8,9-tetrahydro-5-oxa-9-aza-benzocyclohepten-7-yl)-N'-pentyl-malonamide

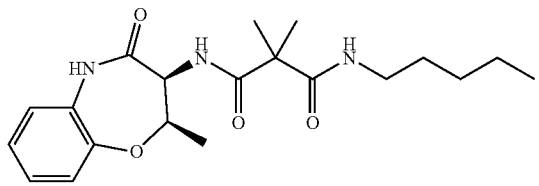

a) 2,2-Dimethyl-N-pentyl-malonamic acid

The title compound was obtained in 60% yield according to the procedures described for example 24a using 2,2,5,5-tetramethyl-[1,3]dioxane-4,6-dione and pentylamine, MS m/e (%): 202.3 (M+H+, 100).

b) 2,2-Dimethyl-N-((6R,7S)-6-methyl-8-oxo-6,7,8,9-tetrahydro-5-oxa-9-aza-benzocyclohepten-7-yl)-N'-pentyl-malonamide The title compound was obtained in 89% yield according to the procedures described for example 2b using 2,2-dimethyl-N-pentyl-malonamic acid and (6R,7S)-7-amino-6-methyl-6,7-dihydro-9H-5-oxa-9-aza-benzocyclohepten-8-one, MS m/e (%): 376.4 (M+H+, 100).

EXAMPLE 26

N-Hexyl-2,2-dimethyl-N'-((6R,7S)-6-methyl-8-oxo-6,7,8,9-tetrahydro-5-oxa-9-aza-benzocyclohepten-7-yl)-malonamide

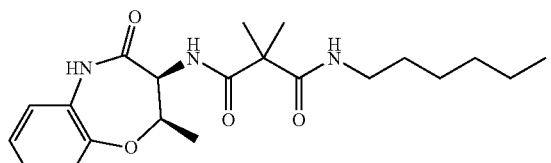

a) N-Hexyl-2,2-dimethyl-malonamic acid

The title compound was obtained in 59% yield according to the procedures described for example 24a using 2,2,5,5-tetramethyl-[1,3]dioxane-4,6-dione and hexylamine, MS m/e (%): 216.3 (M+H+, 100).

b) N-Hexyl-2,2-dimethyl-N'-((6R,7S)-6-methyl-8-oxo-6,7,8,9-tetrahydro-5-oxa-9-aza-benzocyclohepten-7-yl)-malonamide The title compound was obtained in 86% yield according to the procedures described for example 2b using N-hexyl-2,2-dimethyl-malonamic acid and (6R,7S)-7-amino-6-methyl-6,7-dihydro-9H-5-oxa-9-aza-benzocyclohepten-8-one, MS m/e (%): 390.3 (M+H+, 100).

EXAMPLE 27

N-((6R,7S)-6,9-Dimethyl-8-oxo-6,7,8,9-tetrahydro-5-oxa-9-aza-benzocyclohepten-7-yl)-N'-(2,2,3,3,3-pentafluoro-propyl)-malonamide

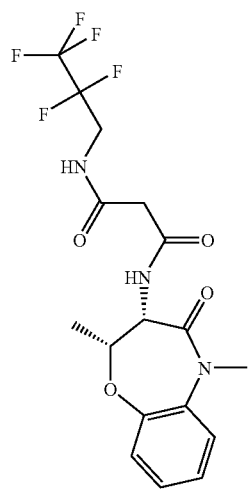

a) ((6R,7S)-6,9-Dimethyl-8-oxo-6,7,8,9-tetrahydro-5-oxa-9-aza-benzocyclohepten-7-yl)-carbamic acid tert-butyl ester The title compound was obtained in 69% yield according to the procedures described for example 5d using ((6R,7S)-6-methyl-8-oxo-6,7,8,9-tetrahydro-5-oxa-9-aza-benzocyclohepten-7-yl)-carbamic acid tert-butyl ester, MS m/e (%): 307.2 (M+H+, 100).

b) (6R,7S)-7-Amino-6,9-dimethyl-6,7-dihydro-9H-5-oxa-9-aza-benzocyclohepten-8-one The title compound was obtained in 52% yield according to the procedures described for example 5e using ((6R,7S)-6,9-dimethyl-8-oxo-6,7,8,9-tetrahydro-5-oxa-9-aza-benzocyclohepten-7-yl)-carbamic acid tert-butyl ester, MS m/e (%): 207.0 (M+H+, 100).

c) N-((6R,7S)-6,9-Dimethyl-8-oxo-6,7,8,9-tetrahydro-5-oxa-9-aza-benzocyclohepten-7-yl)-N'-(2,2,3,3,3-pentafluoro-propyl)-malonamide The title compound was obtained in 89% yield according to the procedures described for example 2b using N-(2,2,3,3,3-pentafluoro-propyl)-malonamic acid and (6R,7S)-7-amino-6,9-dimethyl-6,7-dihydro-9H-5-oxa-9-aza-benzocyclohepten-8-one, MS m/e (%): 424.3 (M+H+, 100).

EXAMPLE 28

N-((6R,7S)-6,9-Dimethyl-8-oxo-6,7,8,9-tetrahydro-5-oxa-9-aza-benzocyclohepten-7-yl)-2-methyl-N'-(2,2,3,3,3-pentafluoro-propyl)-malonamide

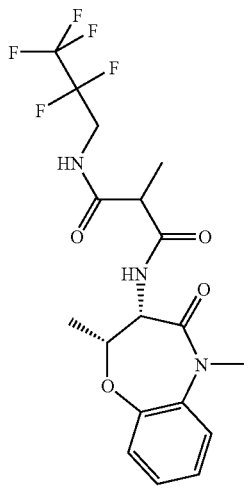

The title compound was obtained in 79% yield according to the procedures described for example 2b using 2-methyl-N-(2,2,3,3,3-pentafluoro-propyl)-malonamic acid and (6R,7S)-7-amino-6,9-dimethyl-6,7-dihydro-9H-5-oxa-9-aza-benzocyclohepten-8-one, MS m/e (%): 436.1 (M–H$^+$, 100).

EXAMPLE 29

N-((6R,7S)-6,9-Dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

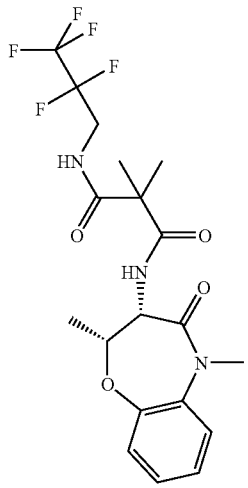

The title compound was obtained in 97% yield according to the procedures described for example 2b using 2,2-dimethyl-N-(2,2,3,3,3-pentafluoro-propyl)-malonamide and (6R,7S)-7-amino-6,9-dimethyl-6,7-dihydro-9H-5-oxa-9-aza-benzocyclohepten-8-one, MS m/e (%): 452.0 (M+H$^+$, 100).

EXAMPLE 30

N-((6R,7S)-6,9-Dimethyl-8-oxo-6,7,8,9-tetrahydro-5-oxa-9-aza-benzocyclohepten-7-yl)-2-isopropyl-N'-(2,2,3,3,3-pentafluoro-propyl)-malonamide

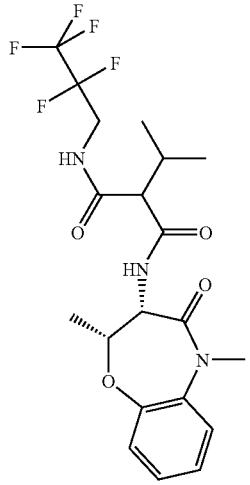

a) 3-Methyl-2-(2,2,3,3,3-pentafluoro-propylcarbamoyl)-butyric acid ethyl ester

The title compound was obtained in similar yield according to the procedures described for example 1b using 1-methylethyl-propanedioic acid monoethyl ester and 2,2,3,3,3-pentafluoropropyl-amine, MS m/e (%): 306.3 (M+H$^+$, 100).

b) 3-Methyl-2-(2,2,3,3,3-pentafluoro-propylcarbamoyl)-butyric acid

The title compound was obtained in quantitative yield according to the procedures described for example 1c using 3-methyl-2-(2,2,3,3,3-pentafluoro-propylcarbamoyl)-butyric acid ethyl ester, MS m/e (%): 276.0 (M–H$^+$, 100).

c) N-((6R,7S)-6,9-Dimethyl-8-oxo-6,7,8,9-tetrahydro-5-oxa-9-aza-benzocyclohepten-7-yl)-2-isopropyl-N'-(2,2,3,3,3-pentafluoro-propyl)-malonamide The title compound was obtained in 96% yield according to the procedures described for example 2b using 3-methyl-2-(2,2,3,3,3-pentafluoro-propylcarbamoyl)-butyric acid and (6R,7S)-7-amino-6,9-dimethyl-6,7-dihydro-9H-5-oxa-9-aza-benzocyclohepten-8-one, MS m/e (%): 466.3 (M+H$^+$, 100).

EXAMPLE 31

N-(3,5-Difluoro-benzyl)-N'-((6R,7S)-6,9-dimethyl-8-oxo-6,7,8,9-tetrahydro-5-oxa-9-aza-benzocyclohepten-7-yl)-2-methyl-malonamide

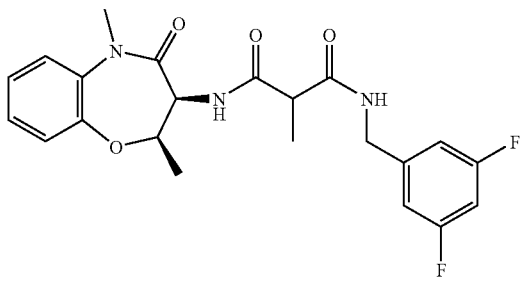

The title compound was obtained in 59% yield according to the procedures described for example 2b using N-(3,5-difluoro-benzyl)-2-methyl-malonamic acid and (6R,7S)-7-amino-6,9-dimethyl-6,7-dihydro-9H-5-oxa-9-aza-benzocyclohepten-8-one, MS m/e (%): 432.4 (M+H$^+$, 100).

EXAMPLE 32

N-(3,5-Difluoro-benzyl)-N'-((6R,7S)-6,9-dimethyl-8-oxo-6,7,8,9-tetrahydro-5-oxa-9-aza-benzocyclohepten-7-yl)-2-[1,3] dioxolan-2-ylmethyl-malonamide

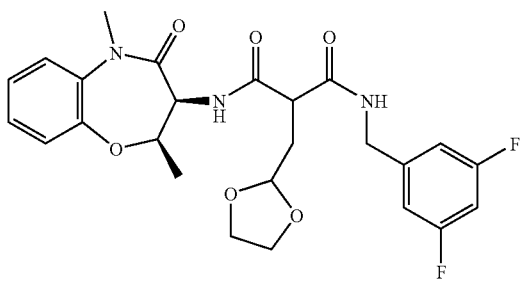

The title compound was obtained in 42% yield according to the procedures described for example 2b using N-(3,5-difluoro-benzyl)-2-[1,3]dioxolan-2-ylmethyl-malonamic acid and (6R,7S)-7-amino-6,9-dimethyl-6,7-dihydro-9H-5-oxa-9-aza-benzocyclohepten-8-one, MS m/e (%): 504.4 (M+H$^+$, 100).

EXAMPLE 33

N-(3,5-Difluoro-benzyl)-N'-((6R,7S)-6,9-dimethyl-8-oxo-6,7,8,9-tetrahydro-5-oxa-9-aza-benzocyclohepten-7-yl)-2-fluoro-2-propyl-malonamide

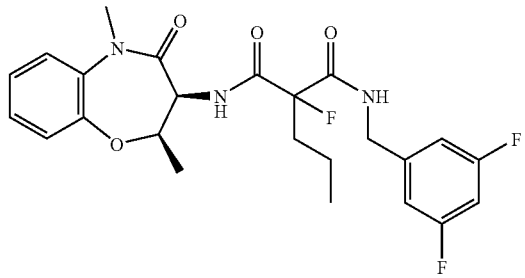

The title compound was obtained in 71% yield according to the procedures described for example 2b using 2-(3,5-difluoro-benzylcarbamoyl)-2-fluoro-pentanoic acid and (6R,7S)-7-amino-6,9-dimethyl-6,7-dihydro-9H-5-oxa-9-aza-benzocyclohepten-8-one, MS m/e (%): 478.4 (M+H$^+$, 100).

EXAMPLE 34

N-((6R,7S)-6,9-Dimethyl-8-oxo-6,7,8,9-tetrahydro-5-oxa-9-aza-benzocyclohepten-7-yl)-2-ethyl-N'-(2,2,3,3,3-pentafluoro-propyl)-malonamide

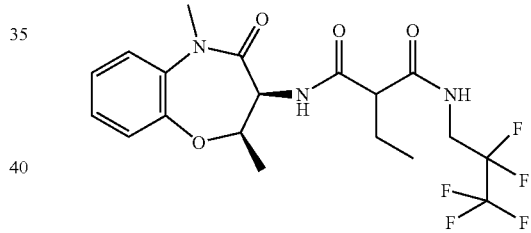

a)
2-(2,2,3,3,3-Pentafluoro-propylcarbamoyl)-butyric acid ethyl ester

The title compound was obtained in similar yield according to the procedures described for example 1b using ethylpropanedioic acid monoethyl ester and 2,2,3,3,3-pentafluoropropylamine, MS m/e (%): 292.0 (M+H$^+$, 100).

b)
2-(2,2,3,3,3-Pentafluoro-propylcarbamoyl)-butyric acid

The title compound was obtained in quantitative yield according to the procedures described for example 1c using 2-(3,5-difluoro-benzylcarbamoyl)-2-fluoro-pentanoic acid ethyl ester, MS m/e (%): 261.9 (M–H$^+$, 100).

c) N-((6R,7S)-6,9-Dimethyl-8-oxo-6,7,8,9-tetrahydro-5-oxa-9-aza-benzocyclohepten-7-yl)-2-ethyl-N'-(2,2,3,3,3-pentafluoro-propyl)-malonamide The title compound was obtained in 99% yield according to the procedures described for example 2b using 2-(2,2,3,3,3-pentafluoro-propylcarbamoyl)-butyric acid and (6R,7S)-

7-amino-6,9-dimethyl-6,7-dihydro-9H-5-oxa-9-aza-benzo-cyclohepten-8-one, MS m/e (%): 452.3 (M+H⁺, 100).

EXAMPLE 35

N-[(6R,7S)-9-(4-Chloro-benzyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide

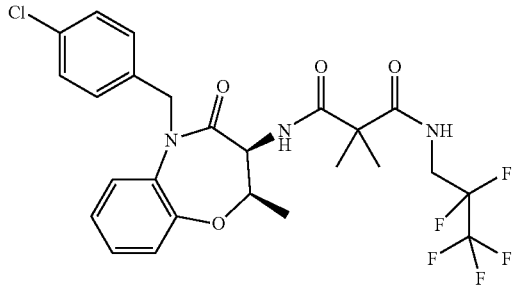

a) [(6R,7S)-9-(4-Chloro-benzyl)-6-methyl-8-oxo-6,7,8,9-tetrahydro-5-oxa-9-aza-benzocyclohepten-7-yl]-carbamic acid tert-butyl ester A solution of 0.10 g (342 mmol) ((6R,7S)-6-methyl-8-oxo-6,7,8,9-tetrahydro-5-oxa-9-aza-benzocyclohepten-7-yl)-carbamic acid tert-butyl ester in 1 ml dimethylformamide was added at 0° C. over a period of 20 minutes to a suspension of 0.015 g (342 mmol) sodiumhydride (55%) in 2 ml dimethylformamide. After 30 minutes 0.056 g (342 mmol) 4-chlorobenzylchloride was added and stirring was continued for 3 hours at 0° C. Extraction with water/ethylacetate and chromatography on silicagel with ethylacetate/heptane yielded 0.12 g (84%) [(6R,7S)-9-(4-chloro-benzyl)-6-methyl-8-oxo-6,7,8,9-tetrahydro-5-oxa-9-aza-benzocyclohepten-7-yl]-carbamic acid tert-butyl ester as white solid, MS m/e (%): 417.2 (M+H⁺, 69), 361.2 (100), 317.1 (91).

b) (6R,7S)-7-Amino-9-(4-chloro-benzyl)-6-methyl-6,7-dihydro-9H-5-oxa-9-aza-benzocyclohepten-8-one The title compound was obtained in 91% yield according to the procedures described for example 5e using [(6R,7S)-9-(4-chloro-benzyl)-6-methyl-8-oxo-6,7,8,9-tetrahydro-5-oxa-9-aza-benzocyclohepten-7-yl]-carbamic acid tert-butyl ester, MS m/e (%): 317.1 (M+H⁺, 100).

c) N-[(6R,7S)-9-(4-Chloro-benzyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide The title compound was obtained in 85% yield according to the procedures described for example 2b using 2,2-dimethyl-N-(2,2,3,3,3-pentafluoro-propyl)-malonamic acid and (6R,7S)-7-amino-9-(4-chloro-benzyl)-6-methyl-6,7-dihydro-9H-5-oxa-9-aza-benzocyclohepten-8-one, MS m/e (%): 562.3 (M+H⁺, 100).

EXAMPLE 36

N-[(6R,7S)-9-(4-Chloro-benzyl)-6-methyl-8-oxo-6,7,8,9-tetrahydro-5-oxa-9-aza-benzocyclohepten-7-yl]-2-methyl-N'-(2,2,3,3,3-pentafluoro-propyl)-malonamide

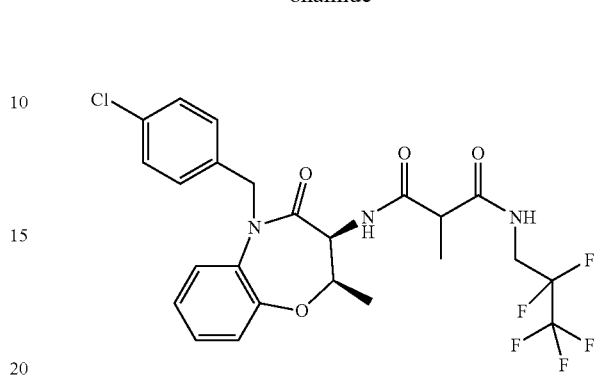

The title compound was obtained in 87% yield according to the procedures described for example 2b using 2-methyl-N-(2,2,3,3,3-pentafluoro-propyl)-malonamic acid and (6R,7S)-7-amino-9-(4-chloro-benzyl)-6-methyl-6,7-dihydro-9H-5-oxa-9-aza-benzocyclohepten-8-one, MS m/e (%): 548.3 (M+H⁺, 100).

EXAMPLE 37

N-((6R,7S)-1-Fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide

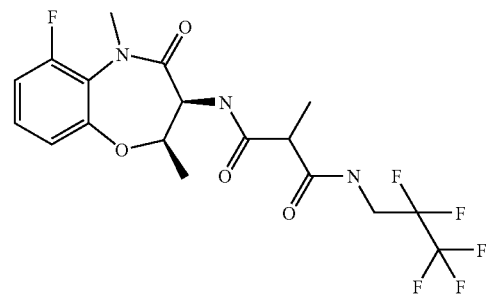

a) ((6R,7S)-1-Fluoro-6,9-dimethyl-8-oxo-6,7,8,9-tetrahydro-5-oxa-9-aza-benzocyclohepten-7-yl)-carbamic acid tert-butyl ester The title compound was obtained in 96% yield according to the procedure described in example 5d) by alkylation with methyliodide of ((6R,7S)-1-fluoro-6-methyl-8-oxo-6,7,8,9-tetrahydro-5-oxa-9-aza-benzocyclohepten-7-yl)-carbamic acid tert-butyl ester [example 21 c)] as a light brown solid, m.p.: 130–138° C., [α]₅₈₉=−121.8° (c=0.827% in MeOH), MS m/e (%): 325.4 (M+H⁺, 62).

b) (6R,7S)-7-Amino-1-fluoro-6,9-dimethyl-6,7-dihydro-9H-5-oxa-9-aza-benzocyclohepten-8-one The title compound was obtained in quantitative yield according to the procedure described in example 5e) by cleavage of the protecting group of ((6R,7S)-1-fluoro-6,9-dimethyl-8-oxo-6,7,8,9-tetrahydro-5-oxa-9-aza-benzocyclohepten-7-yl)-carbamic acid tert-butyl ester as a off-white solid, m.p.: 185–188° C., [α]$_{589}$=–141.9° (c=0.692% in MeOH), MS m/e (%): 225.1 (M+H$^+$, 100).

c) N-((6R,7S)-1-Fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide (RO4922693)

The title compound was obtained in 86% yield according to the procedure described in example 2b) by condensation of (6R,7S)-7-amino-1-fluoro-6,9-dimethyl-6,7-dihydro-9H-5-oxa-9-aza-benzocyclohepten-8-one with 2-methyl-N-(2,2,3,3,3-pentafluoro-propyl)-malonamic acid [example 1c)], m.p.: 126–134° C., [α]$_{589}$=–91.73° (c=0.964% in MeOH), MS m/e (%): 456.4 (M+H$^+$, 100).

EXAMPLE 38

N-((6R,7S)-2-Fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide

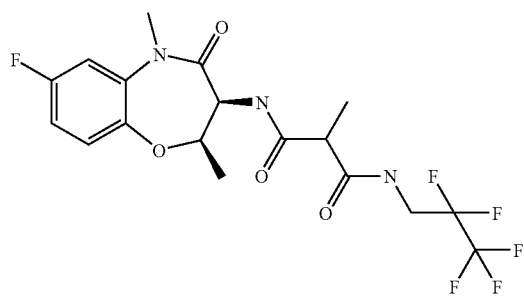

a) ((6R,7S)-2-Fluoro-6,9-dimethyl-8-oxo-6,7,8,9-tetrahydro-5-oxa-9-aza-benzocyclohepten-7-yl)-carbamic acid tert-butyl ester The title compound was obtained in 83% yield according to the procedure described in example 5d) by alkylation with methyliodide of ((6R,7S)-2-fluoro-6-methyl-8-oxo-6,7,8,9-tetrahydro-5-oxa-9-aza-benzocyclohepten-7-yl)-carbamic acid tert-butyl ester [example 23 c)] as a light yellow solid, m.p.: 129–133° C., [α]$_{589}$=–210.45° (c=0.790% in MeOH), MS m/e (%): 325 (M+H$^+$, 79).

b) (6R,7S)-7-Amino-2-fluoro-6,9-dimethyl-6,7-dihydro-9H-5-oxa-9-aza-benzocyclohepten-8-one The title compound was obtained in 99% yield according to the procedure described in example 5e) by cleavage of the protecting group of ((6R,7S)-2-fluoro-6,9-dimethyl-8-oxo-6,7,8,9-tetrahydro-5-oxa-9-aza-benzocyclohepten-7-yl)-carbamic acid tert-butyl ester as a dark brown oil, MS m/e (%): 225.4 (M+H$^+$, 100).

c) N-((6R,7S)-2-Fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide The title compound was obtained in 89% yield according to the procedure described in example 2b) by condensation of (6R,7S)-7-amino-2-fluoro-6,9-dimethyl-6,7-dihydro-9H-5-oxa-9-aza-benzocyclohepten-8-one with 2-methyl-N-(2,2,3,3,3-pentafluoro-propyl)-malonamic acid [example 1c)] as a light brown foam, m.p.: 126–134° C., [α]$_{589}$=–148.18° (c=0.803% in MeOH), MS m/e (%): 456.4 (M+H$^+$, 100).

EXAMPLE 39

N-((6R,7S)-1-Fluoro-6,9-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

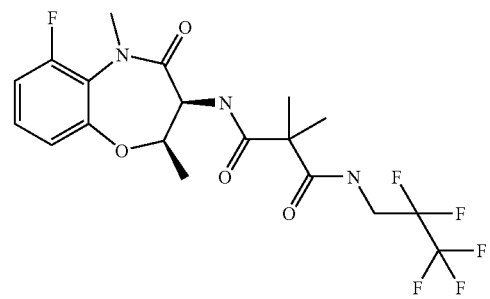

The title compound was obtained in 69% yield according to the procedure described in example 2b) by condensation of (6R,7S)-7-amino-1-fluoro-6,9-dimethyl-6,7-dihydro-9H-5-oxa-9-aza-benzocyclohepten-8-one [example 37 b)] with 2,2-dimethyl-N-(2,2,3,3,3-pentafluoropropyl)-malonamic acid [example 4a)], [α]$_{589}$=–79.75° (c=1.036% in MeOH), MS m/e (%): 470.3 (M+H$^+$, 29).

EXAMPLE 40

N-((6R,7S)-2-Fluoro-6,9-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

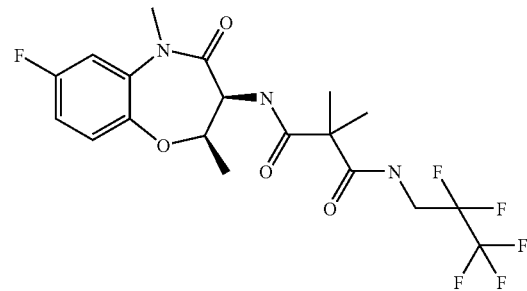

The title compound was obtained in 74% yield according to the procedure described in example 2b) by condensation of (6R,7S)-7-amino-2-fluoro-6,9-dimethyl-6,7-dihydro-9H-

5-oxa-9-aza-benzocyclohepten-8-one [example 38 b)] with 2,2-dimethyl-N-(2,2,3,3,3-pentafluoropropyl)-malonamic acid [example 4a)]; [α]$_{589}$=−151.23° (c=0.969% in MeOH), MS m/e (%): 470.1 (M+H$^+$, 66).

EXAMPLE 41

N-((6R,7S)-2-Fluoro-6-methyl-8-oxo-6,7,8,9-tetrahydro-5-oxa-9-aza-benzocyclohepten-7-yl)-2-methoxy-N'-(2,2,3,3,3-pentafluoro-propyl)-malonamide

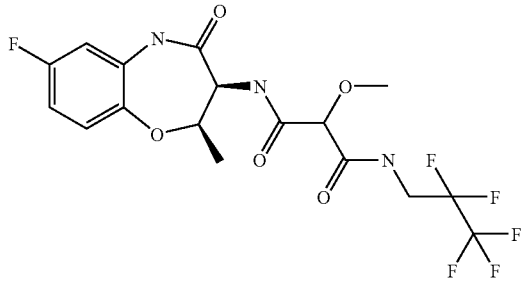

a) 2-Methoxy-N-(2,2,3,3,3-pentafluoro-propyl)-malonamic acid

The title compound was obtained in comparable yields according to the procedures described for 2-methyl-N-(2,2,3,3,3-pentafluoro-propyl)-malonamic acid (see example 1) using diethyl 2-methoxy-malonate instead of diethyl methyl-malonate in step a), MS m/e (%): 266.0 (M+H$^+$, 69).

b) N-((6R,7S)-2-Fluoro-6-methyl-8-oxo-6,7,8,9-tetrahydro-5-oxa-9-aza-benzocyclohepten-7-yl)-2-methoxy-N'-(2,2,3,3,3-pentafluoro-propyl)-malonamide The title compound was obtained in 86% yield according to the procedure described in example 2b) by condensation of (6R,7S)-7-amino-2-fluoro-6-methyl-6,7-dihydro-9H-5-oxa-9-aza-benzocyclohepten-8-one [example 23] with 2-methoxy-N-(2,2,3,3,3-pentafluoro-propyl)-malonamic acid as an off-white solid, [α]$_{589}$=−172.79° (c=0.795% in MeOH), MS m/e (%): 458.4 (M+H$^+$, 100).

EXAMPLE 42

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2,2-dimethyl-N'-(2,2,3,3,3-pentafluoro-propyl)-malonamide

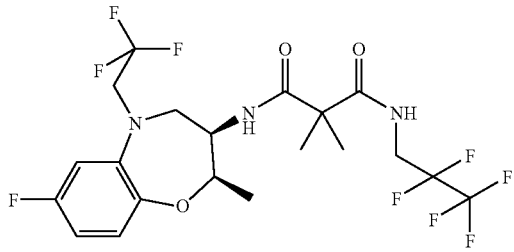

a) [(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-carbamic acid tert-butyl ester To a solution of 0.50 g (1.61 mmol) ((6R,7S)-2-fluoro-6-methyl-8-oxo-6,7,8,9-tetrahydro-5-oxa-9-aza-benzocyclohepten-7-yl)-carbamic acid tert-butyl ester in 5 ml dimethylformamide were added at room temperature 0.57 g (2.42 mmol) 2,2,2-trifluorethyl triflate and 0.80 g (2.43 mmol) cesium carbonate. Stirring was continued for 5 hours. Extraction with ethylacetate/water and chromatography on silicagel with heptane to ethylacetate/heptane 2:8 yielded 0.55 g (87%) [(6R,7S)-2-fluoro-6-methyl-8-oxo-9-(2,2,2-trifluoro-ethyl)-6,7,8,9-tetrahydro-5-oxa-9-aza-benzocyclohepten-7-yl]-carbamic acid tert-butyl ester, MS m/e (%): 415.3 (M+Na$^+$, 100), 393.2 (M+H$^+$, 8), 293.1 (43).

b) (6R,7S)-7-Amino-2-fluoro-6-methyl-9-(2,2,2-trifluoro-ethyl)-6,7-dihydro-9H-5-oxa-9-aza-benzocyclohepten-8-one To a solution of 0.50 g (1.27 mmol) [(6R,7S)-2-fluoro-6-methyl-8-oxo-9-(2,2,2-trifluoro-ethyl)-6,7,8,9-tetrahydro-5-oxa-9-aza-benzocyclohepten-7-yl]-carbamic acid tert-butyl ester in 5 ml tetrahydrofurane were added 1.89 g orthophosphoric acid. The mixture was stirred at room temperature for 2 days. Extraction with ethylacetate/water and chromatography on silicagel with dichloromethane/methanol 98/2 yielded 0.31 g (83%) (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 293.1 (M+H$^+$, 100).

c) N-[(6R,7S)-2-Fluoro-6-methyl-8-oxo-9-(2,2,2-trifluoro-ethyl-6,7,8,9-tetrahydro-5-oxa-9-aza-benzocyclohepten-7-yl]-2,2-dimethyl-N'-(2,2,3,3,3-pentafluoro-propyl)-malonamide The title compound was obtained in 91% yield according to the procedures described for example 2b using 2,2-dimethyl-N-(2,2,3,3,3-pentafluoro-propyl)-malonamic acid and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 538.3 (M+H$^+$, 100).

EXAMPLE 43

(2,2,3,3,3-Pentafluoro-propyl)-carbamic acid (S)-1-((6R,7S)-6,9-dimethyl-8-oxo-6,7,8,9-tetrahydro-5-oxa-9-aza-benzocyclohepten-7-ylcarbamoyl)-ethyl ester

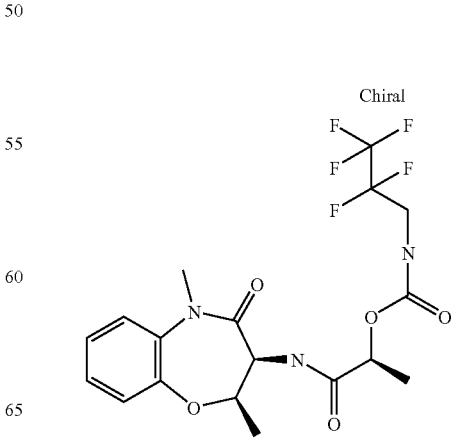

a) (S)-N-((6R,7S)-6,9-Dimethyl-8-oxo-6,7,8,9-tetrahydro-5-oxa-9-aza-benzocyclohepten-7-yl)-2-hydroxy-propionamide The title compound was obtained in 78% yield according to the procedure described in example 2b) by condensation of (6R,7S)-7-amino-6,9-dimethyl-6,7-dihydro-9H-5-oxa-9-aza-benzocyclohepten-8-one (example 27b) with L-(+)-lactic acid as a white solid, MS m/e (%): 279 (M+H$^+$, 100).

b) (2,2,3,3,3-Pentafluoro-propyl)-carbamic acid (S)-1-((6R,7S)-6,9-dimethyl-8-oxo-6,7,8,9-tetrahydro-5-oxa-9-aza-benzocyclohepten-7-ylcarbamoyl)-ethyl ester In an inert atmosphere and under exclusion of moisture, a solution of 95 mg (0.34 mmol) of (S)—N-((6R,7S)-6,9-dimethyl-8-oxo-6,7,8,9-tetrahydro-5-oxa-9-aza-benzocyclohepten-7-yl)-2-hydroxy-propionamide in 1 ml of toluene was treated with 0.57 ml (0.41 mmol) of triethylamine and 70.9 mg (0.34 mmol) of 4-nitrophenyl chloroformate at room temperature. After stirring at room temperature during the weekend, 0.374 ml (0.34 mmol) of 2,2,3,3,3-pentafluoropropylamine were added and stirring was continued overnight. The solvent was removed by distillation and the crude product was chromatographed on silica gel using a gradient of a 1:3- to 3:1-mixture of ethyl acetate and heptane as the eluent. There were obtained 28 mg (18% of theory) of the title compound as a colourless oil, MS m/e (%): 454.4 (M+H$^+$, 100).

EXAMPLE 44

(2,2,3,3,3-Pentafluoro-propyl)-carbamic acid (S)-1-((S)-3,9-dimethyl-8-oxo-6,7,8,9-tetrahydro-5-oxa-9-aza-benzocyclohepten-7-ylcarbamoyl)-ethyl ester

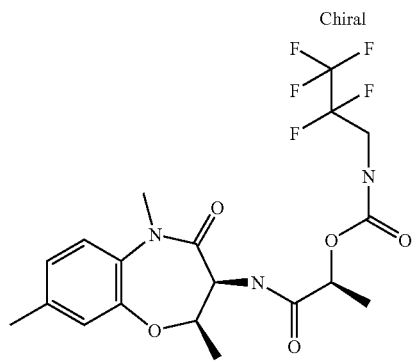

a) (S)-N—((S)-3,9-Dimethyl-8-oxo-6,7,8,9-tetrahydro-5-oxa-9-aza-benzocyclohepten-7-yl)-2-hydroxy-propionamide The title compound was obtained according to the procedure described in example 2b) by condensation of (S)-7-amino-3,9-dimethyl-6,7-dihydro-9H-5-oxa-9-aza-benzocyclohepten-8-one [example 7e)] with L-(+)-lactic acid, MS m/e (%): 279.3 (M+H$^+$, 98); the crude product was used in the next step without further purification.

b) (2,2,3,3,3-Pentafluoro-propyl)-carbamic acid (S)-1-((S)-3,9-dimethyl-8-oxo-6,7,8,9-tetrahydro-5-oxa-9-aza-benzocyclohepten-7-ylcarbamoyl)-ethyl ester The title compound was obtained in 6% yield according to the procedure described in example 43 d) by the consecutive treatment of (S)-N—((S)-3,9-dimethyl-8-oxo-6,7,8,9-tetrahydro-5-oxa-9-aza-benzocyclohepten-7-yl)-2-hydroxy-propionamide with 4-nitrophenyl chloroformate and 2,2,3,3,3-pentafluoropropylamine, white solid, MS m/e (%): 452.5 (M–H$^+$, 90).

EXAMPLE 45

(2,2,3,3,3-Pentafluoro-propyl)-carbamic acid (S)-1-((6R,7S)-6-methyl-8-oxo-6,7,8,9-tetrahydro-5-oxa-9-aza-benzocyclohepten-7-ylcarbamoyl)-ethyl ester

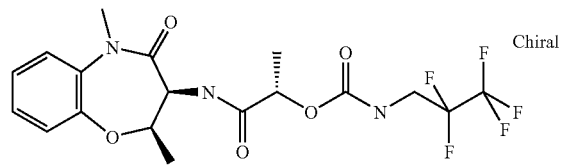

a) (S)-2-Hydroxy-N-((6R,7S)-6-methyl-8-oxo-6,7,8,9-tetrahydro-5-oxa-9-aza-benzocyclohepten-7-yl)-propionamide The title compound was obtained in quantitative yield according to the procedure described in example 2b) by condensation of (6R,7S)-7-amino-6-methyl-6,7-dihydro-9H-5-oxa-9-aza-benzocyclohepten-8-one (example 15 d) with L-(+)-lactic acid as a light brown solid, MS m/e (%): 265.0 (M+H$^+$, 100).

b) Carbonic acid (S)-1-((6R,7S)-6-methyl-8-oxo-6,7,8,9-tetrahydro-5-oxa-9-aza-benzocyclohepten-7-ylcarbamoyl)-ethyl ester 4-nitro-phenyl ester A mixture of 290 mg (1.1 mmol) of (S)-2-hydroxy-N-((6R,7S)-6-methyl-8-oxo-6,7,8,9-tetrahydro-5-oxa-9-aza-benzocyclohepten-7-yl)-propionamide and 0.177 ml (2.19 mmol) of pyridine in 10 ml of dichloromethane was treated with 274 mg (1.32 mmol) of 4-nitrophenyl chloroformate and stirred overnight at room temperature. The solvent was removed by distillation and the crude product was purified by flash-chromatography on silica gel using an ascending gradient of ethyl acetate in heptane as the eluent to yield 220 mg (47% of theory) of the title compound as a white solid, MS m/e (%): 430.3 (M+H$^+$, 100).

c) (2,2,3,3,3-Pentafluoro-propyl)-carbamic acid (S)-1-((6R,7S)-6-methyl-8-oxo-6,7,8,9-tetrahydro-5-oxa-9-aza-benzocyclohepten-7-ylcarbamoyl)-ethyl ester A mixture of 60 mg (0.14 mmol) of carbonic acid (S)-1-((6R,7S)-6-methyl-8-oxo-6,7,8,9-tetrahydro-5-oxa-9-aza-benzocyclohepten-7-ylcarbamoyl)-ethyl ester 4-nitro-phenyl ester and 0.304 ml (2.8 mmol) of 2,2,3,3,3-pentafluoropropylamine was stirred at room temperature overnight. The mixture was purified by flash-chromatography on silica gel using an ascending gradient of ethyl acetate in heptane as the eluent to yield 60 mg (98% of theory) of the title compound as a white solid, MS m/e (%): 440.3 (M+H⁺, 100).

EXAMPLE 46

(3,5-Difluoro-benzyl)-carbamic acid (S)-1-((6R,7S)-6-methyl-8-oxo-6,7,8,9-tetrahydro-5-oxa-9-aza-benzocyclohepten-7-ylcarbamoyl)-ethyl ester

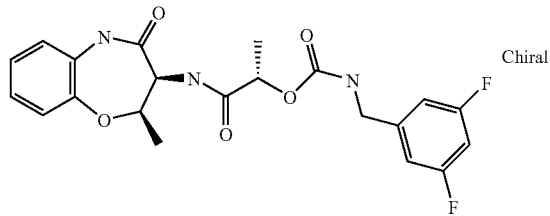

The title compound was obtained in 87% yield according to the procedure described in example 45 c) by reaction of carbonic acid (S)—1-((6R,7S)-6-methyl-8-oxo-6,7,8,9-tetrahydro-5-oxa-9-aza-benzocyclohepten-7-ylcarbamoyl)-ethyl ester 4-nitro-phenyl ester with 3,5-difluorobenzylamine as a white solid, MS m/e (%): 434.4 (M+H⁺, 95).

EXAMPLE 47

(2,2,3,3,3-Pentafluoro-propyl)-carbamic add (S)-1-((6R,7S)-1-fluoro-6-methyl-8-oxo-6,7,8,9-tetrahydro-5-oxa-9-aza-benzocyclohepten-7-ylcarbamoyl)-ethyl ester

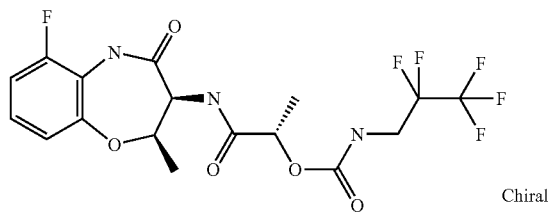

a) (S)—N-((6R,7S)-1-Fluoro-6-methyl-8-oxo-6,7,8,9-tetrahydro-5-oxa-9-aza-benzocyclohepten-7-yl)-2-hydroxy-propionamide The title compound was obtained in 92% yield according to the procedure described in example 2b) by condensation of (6R,7S)-7-amino-1-fluoro-6-methyl-6,7-dihydro-9H-5-oxa-9-aza-benzocyclohepten-8-one [example 21 d)] with L-(+)-lactic acid as an off-white solid, m.p.: 221–225° C., MS m/e (%): 283.0 (M+H⁺, 100).

b) Carbonic acid (S)-1-((6R,7S)-1-fluoro-6-methyl-8-oxo-6,7,8,9-tetrahydro-5-oxa-9-aza-benzocyclohepten-7-ylcarbamoyl)-ethyl ester 4-nitro-phenyl ester The title compound was obtained in 85% yield according to the procedure described in example 45 b) by reaction of (S)—N-((6R,7S)-1-fluoro-6-methyl-8-oxo-6,7,8,9-tetrahydro-5-oxa-9-aza-benzocyclohepten-7-yl)-2-hydroxy-propionamide with 4-nitrophenyl chloroformate as a white solid, m.p.: 140–145° C., MS m/e (%): 448.1 (M+H⁺, 83).

c) (2,2,3,3,3-Pentafluoro-propyl)-carbamic acid (S)-1-((6R,7S)-1-fluoro-6-methyl-8-oxo-6,7,8,9-tetrahydro-5-oxa-9-aza-benzocyclohepten-7-ylcarbamoyl)-ethyl ester The title compound was obtained in 89% yield according to the procedure described in example 45 c) by reaction of carbonic acid (S)-1-((6R,7S)-1-fluoro-6-methyl-8-oxo-6,7,8,9-tetrahydro-5-oxa-9-aza-benzocyclohepten-7-ylcarbamoyl)-ethyl ester 4-nitro-phenyl ester with 2,2,3,3,3-pentafluoropropylamine as a white foam, MS m/e (%): 458.3 (M+H⁺, 100).

EXAMPLE 48

(2,2,3,3,3-Pentafluoro-propyl)-carbamic acid (S)-1-((6R,7S)-2-fluoro-6,9-dimethyl-8-oxo-6,7,8,9-tetrahydro-5-oxa-9-aza-benzocyclohepten-7-ylcarbamoyl)-ethyl ester

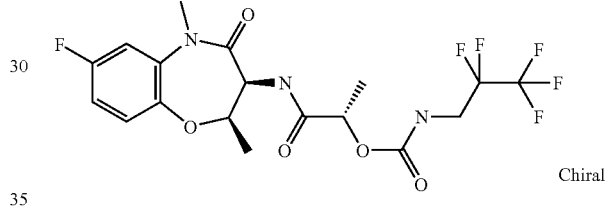

a) (S)-N-((6R,7S)-2-Fluoro-6,9-dimethyl-8-oxo-6,7,8,9-tetrahydro-5-oxa-9-aza-benzocyclohepten-7-yl)-2-hydroxy-propionamide The title compound was obtained in 99% yield according to the procedure described in example 2b) by condensation of (6R,7S)-7-amino-2-fluoro-6,9-dimethyl-6,7-dihydro-9H-5-oxa-9-aza-benzocyclohepten-8-one [example 38 b)] with L-(+)-lactic acid as a light brown oil, MS m/e (%): 297.1 (M+H⁺, 36).

b) Carbonic acid (S)-1-((6R,7S)-2-fluoro-6,9-dimethyl-8-oxo-6,7,8,9-tetrahydro-5-oxa-9-aza-benzocyclohepten-7-ylcarbamoyl)-ethyl ester 4-nitro-phenyl ester The title compound was obtained in 81% yield according to the procedure described in example 45 b) by reaction of (S)—N-((6R,7S)-2-fluoro-6,9-dimethyl-8-oxo-6,7,8,9-tetrahydro-5-oxa-9-aza-benzocyclohepten-7-yl)-2-hydroxy-propionamide with 4-nitrophenyl chloroformate as a light brown oil, MS m/e (%): 462.3 (M+H⁺, 89).

c) (2,2,3,3,3-Pentafluoro-propyl)-carbamic acid (S)-1-((6R,7S)-2-fluoro-6,9-dimethyl-8-oxo-6,7,8,9-tetrahydro-5-oxa-9-aza-benzocyclohepten-7-ylcarbamoyl)-ethyl ester The title compound was obtained in 84% yield according to the procedure described in example 45 c) by reaction of carbonic acid (S)-1-((6R,7S)-2-fluoro-6,9-dimethyl-8-oxo-6,7,8,9-tetrahydro-5-oxa-9-aza-benzocyclohepten-7-ylcarbamoyl)-ethyl ester 4-nitro-phenyl ester with 2,2,3,3,3-pentafluoropropylamine as a light yellow solid, m.p.: 148–150° C., $[\alpha]_{589}=-165.41°$ (c=0.98% in MeOH), MS m/e (%): 472.1 (M+H$^+$, 100).

EXAMPLE 49

(2,2,3,3,3-Pentafluoro-propyl)-carbamic acid (S)-1-((6S,7S)-2-fluoro-8-oxo-6-trifluoromethyl-6,7,8,9-tetrahydro-5-oxa-9-aza-benzocyclohepten-7-ylcarbamoyl)-ethyl ester

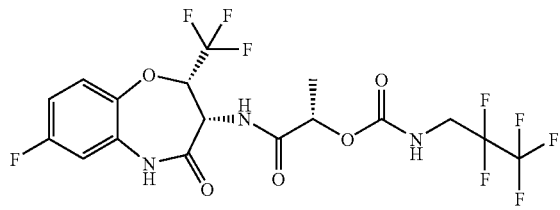

a) Racemic (2S,3S and 2R,3R)-2-dibenzylamino-4,4,4-trifluoro-3-(4-fluoro-2-nitro-phenoxy)-butyric To 15.4 g (43.6 mmol) DL-4,4,4-trifluoro-N,N-bis(phenylmethyl)-threonine in 60 ml dimethylformamide were added in portions 4.03 g (92.4 mmol) sodium hydride (55%) at 0° C. The suspension was stirred for 2 hours and then 10.5 ml (95.9 mmol) 2,5-difluoro-nitrobenzene were added. After stirring overnight at 0° C. the mixture was poured on ice/water. Extraction with ethylacetate and chromatography on silicagel with ethylacetate/heptane 1:1 (and adding 30% methanol after the first five 250 ml fractions) yielded 11.7 g (55%) racemic (2S,3S and 2R,3R)-2-dibenzylamino-4,4,4-trifluoro-3-(4-fluoro-2-nitro-phenoxy)-butyric acid acid as yellow oil, MS m/e (%): 491.1 (M–H$^+$, 100).

b) Racemic (2S,3S and 2R,3R)-3-(2-amino-4-fluoro-phenoxy)-2-dibenzylamino-4,4,4-trifluoro-butyric acid 5.00 g (10.2 mmol) (2S,3S and 2R,3R)-2-dibenzylamino-4,4,4-trifluoro-3-(4-fluoro-2-nitro-phenoxy)-butyric acid acid in 300 ml methanol were hydrogenated with 1.19 g Raney-Nickel. Filtration and removal of the solvent by distillation yielded 4.19 g (89%) racemic (2S,3S and 2R,3R)-3-(2-amino-4-fluoro-phenoxy)-2-dibenzylamino-4,4,4-trifluoro-butyric acid as light yellow oil, MS m/e (%): 461.2 (M–H$^+$, 100).

c) Racemic (6S,7S and 6R,7R)-7-dibenzylamino-2-fluoro-6-trifluoromethyl-6,7-dihydro-9H-5-oxa-9-aza-benzocyclohepten-8-one The title compound was obtained in similar yield yield according to the procedures described for example 5c using racemic (2S,3S and 2R,3R)-3-(2-amino-4-fluoro-phenoxy)-2-dibenzylamino-4,4,4-trifluoro-butyric acid, MS m/e (%): 445.2 (M+H$^+$, 100).

d) (–)-(6S,7S)-7-dibenzylamino-2-fluoro-6-trifluoromethyl-6,7-dihydro-9H-5-oxa-9-aza-benzocyclohepten-8-one (RO4963779) and (+)-(6R,7R)-7-dibenzylamino-2-fluoro-6-trifluoromethyl-6,7-dihydro-9H-5-oxa-9-aza-benzocyclohepten-8-one Racemic (2S,3S and 2R,3R)-3-(2-amino-4-fluoro-phenoxy)-2-dibenzylamino-4,4,4-trifluoro-butyric acid was separated by chiral HPLC on Chiralpak AD with ethylacetate/heptane 1/9 to yield the title compounds.

e) (6S,7S)-7-Amino-2-fluoro-6-trifluoromethyl-6,7-dihydro-9H-5-oxa-9-aza-benzocyclohepten-8-one The title compound was prepared by hydrogenation of (–)-(6S,7S)-7-dibenzylamino-2-fluoro-6-trifluoromethyl-6,7-dihydro-9H-5-oxa-9-aza-benzocyclohepten-8-one in methanol with Pd/C (10%), MS m/e (%): 265.2 (M+H$^+$, 100).

f) (S)-N-((6S,7S)-2-Fluoro-8-oxo-6-trifluoromethyl-6,7,8,9-tetrahydro-5-oxa-9-aza-benzocyclohepten-7-yl)-2-hydroxy-propionamide The title compound was obtained in 89% yield according to the procedure described in example 2b) by condensation of (6S,7S)-7-amino-2-fluoro-6-trifluoromethyl-6,7-dihydro-9H-5-oxa-9-aza-benzocyclohepten-8-one with L-(+)-lactic acid as a white solid, MS m/e (%): 337.2 (M+H$^+$, 100).

g) (2,2,3,3,3-Pentafluoro-propyl)-carbamic acid (S)-1-((6S,7S)-2-fluoro-8-oxo-6-trifluoromethyl-6,7,8,9-tetrahydro-5-oxa-9-aza-benzocyclohepten-7-ylcarbamoyl)-ethyl ester The title compound was obtained in similar yield in analogy to the procedure described in example 43d by treatment of (S)-N-((6S,7S)-2-fluoro-8-oxo-6-trifluoromethyl-6,7,8,9-tetrahydro-5-oxa-9-aza-benzocyclohepten-7-yl)-2-hydroxy-propionamide with 4-nitrophenyl chloroformate, isolation of the resulting carbonate by chromatography on silicagel with heptane/ethylacetate, and treatment with 2,2,3,3,3-pentafluoropropylamine, white solid, MS m/e (%): 512.3 (M+H$^+$, 100).

EXAMPLE 50

Racemic N-((6S,7S and 6R,7R)-2-Fluoro-8-oxo-6-trifluoromethyl-6,7,8,9-tetrahydro-5-oxa-9-aza-benzocyclohepten-7-yl)-2,2-dimethyl-N'-(2,2,3,3,3-pentafluoro-propyl)-malonamide

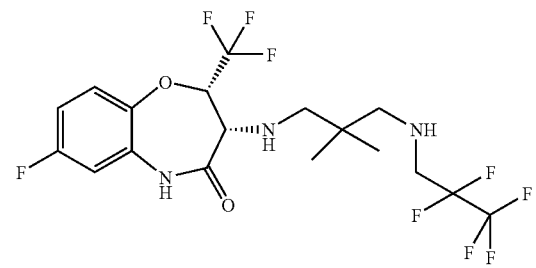

Racemic (6S,7S and 6R,7R)-7-amino-2-fluoro-6-trifluoromethyl-6,7-dihydro-9H-5-oxa-9-aza-benzocyclohepten- 8-one was prepared according to the procedure described in example 49e by hydrogenation of racemic (6S,7S and 6R,7R)-7-dibenzylamino-2-fluoro-6-trifluoromethyl-6,7-dihydro-9H-5-oxa-9-aza-benzocyclohepten-8-one in methanol with Pd/C (10%). The title compound was obtained according to the procedures described for example 2b using 2,2-dimethyl-N-(2,2,3,3,3-pentafluoro-propyl)-malonamic acid and racemic (6S,7S and 6R,7R)-7-amino-2-fluoro-6-trifluoromethyl-6,7-dihydro-9H-5-oxa-9-aza-benzocyclohepten-8-one, MS m/e (%): 508.2 (M−H⁺, 100).

EXAMPLE 51

N-((6R,7S)-9-Cyclopropylmethyl-2-fluoro-6-methyl-8-oxo-6,7,8,9-tetrahydro-5-oxa-9-aza-benzocyclohepten-7-yl)-2,2-dimethyl-N-(2,2,3,3,3-pentafluoro-propyl)-malonamide

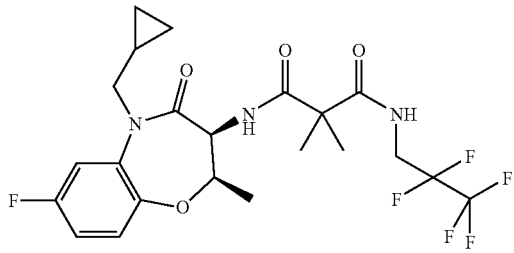

a) ((6R,7S)-9-Cyclopropylmethyl-2-fluoro-6-methyl-8-oxo-6,7,8,9-tetrahydro-5-oxa-9-aza-benzocyclohepten-7-yl)-carbamic acid tert-butyl ester The title compound was obtained in 88% yield according to the procedure described in example 42a from ((6R,7S)-2-fluoro-6-methyl-8-oxo-6,7,8,9-tetrahydro-5-oxa-9-aza-benzocyclohepten-7-yl)-carbamic acid tert-butyl ester and (bromomethyl)-cyclopropane, colorless oil, MS m/e (%): 365.1 (M+H⁺, 21), 309.5 (34), 265.2 (100).

b) (6R,7S)-7-Amino-9-cyclopropylmethyl-2-fluoro-6-methyl-6,7-dihydro-9H-5-oxa-9-aza-benzocyclohepten-8-one The title compound was obtained in 13% yield according to the procedure described in example 42b from ((6R,7S)-9-cyclopropylmethyl-2-fluoro-6-methyl-8-oxo-6,7,8,9-tetrahydro-5-oxa-9-aza-benzocyclohepten-7-yl)-carbamic acid tert-butyl ester, MS m/e (%): 265.3 (M+H⁺, 100).

c) N-((6R,7S)-9-Cyclopropylmethyl-2-fluoro-6-methyl-8-oxo-6,7,8,9-tetrahydro-5-oxa-9-aza-benzocyclohepten-7-yl)-2,2-dimethyl-N-(2,2,3,3,3-pentafluoro-propyl)-malonamide The title compound was obtained in 87% yield according to the procedures described for example 2b using 2,2-dimethyl-N-(2,2,3,3,3-pentafluoro-propyl)-malonamic acid and (6R,7S)-7-amino-9-cyclopropylmethyl-2-fluoro-6-methyl-6,7-dihydro-9H-5-oxa-9-aza-benzocyclohepten-8-one, MS m/e (%): 510.5 (M+H⁺, 100).

EXAMPLE 52

N-((6R,7S)-9-Allyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

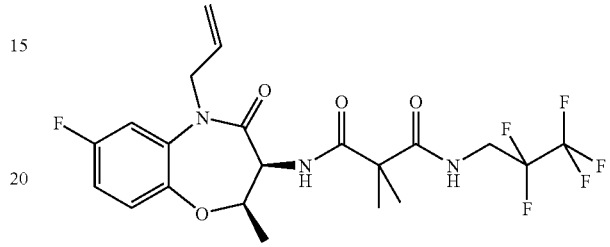

a) ((6R,7S)-9-Allyl-2-fluoro-6-methyl-8-oxo-6,7,8,9-tetrahydro-5-oxa-9-aza-benzocyclohepten-7-yl)-carbamic acid tert-butyl ester To a suspension of 0.28 g (6.44 mmol) sodium hydride in 40 ml dimethylformamide were added at 0° C. 2.0 g (6.44 mmol) ((6R,7S)-2-fluoro-6-methyl-8-oxo-6,7,8,9-tetrahydro-5-oxa-9-aza-benzocyclohepten-7-yl)-carbamic acid tert-butyl ester in 20 ml dimethylformamide. After 30 minutes 0.55 ml (6.44 mmol) allyl bromide was added. Stirring was continued for 3 hours. Extraction with ethylacetate/water and chromatography on silicagel with heptane to ethylacetate/heptane 1:1 yielded 2.24 g (99%) ((6R,7S)-9-allyl-2-fluoro-6-methyl-8-oxo-6,7,8,9-tetrahydro-5-oxa-9-aza-benzocyclohepten-7-yl)-carbamic acid tert-butyl ester, MS m/e (%): 351.2 (M+H⁺, 80), 295.3 (100), 251.1 (82).

b) (6R,7S)-9-Allyl-7-amino-2-fluoro-6-methyl-6,7-dihydro-9H-5-oxa-9-aza-benzocyclohepten-8-one The title compound was obtained in quantitative % yield (raw material) according to the procedure described in example 42b from ((6R,7S)-9-allyl-2-fluoro-6-methyl-8-oxo-6,7,8,9-tetrahydro-5-oxa-9-aza-benzocyclohepten-7-yl)-carbamic acid tert-butyl ester, MS m/e (%): 251.2 (M+H⁺, 100).

c) N-((6R,7S)-9-Allyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained in 63% yield according to the procedures described for example 2b using 2,2-dimethyl-N-(2,2,3,3,3-pentafluoro-propyl)-malonamic acid and (6R,7S)-9-allyl-7-amino-2-fluoro-6-methyl-6,7-dihydro-9H-5-oxa-9-aza-benzocyclohepten-8-one, MS m/e (%): 496.4 (M+H⁺, 100).

EXAMPLE 53

N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide

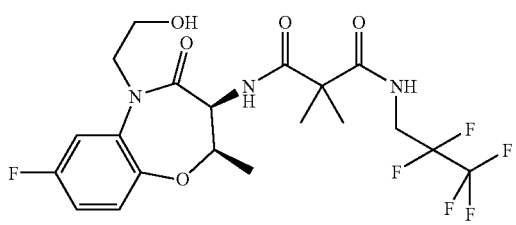

a) [(6R,7S)-2-Fluoro-6-methyl-8-oxo-9-(2-oxo-ethyl)-6,7,8,9-tetrahydro-5-oxa-9-aza-benzocyclohepten-7-yl]-carbamic acid tert-butyl ester A solution of 2.20 g (6.28 mmol) ((6R,7S)-9-allyl-2-fluoro-6-methyl-8-oxo-6,7,8,9-tetrahydro-5-oxa-9-aza-benzocyclohepten-7-yl)-carbamic acid tert-butyl ester in 120 ml dichloromethane was treated with ozone at −75° C. for 20 minutes. Methyl sulfide, 2.27 g (30.6 mmol), was added and the solution was stirred for 4.5 hours at room temperature. The solvent was distilled off under vacuum and the residue was extracted with ethylacetate/water to yield 2.05 g crude [(6R,7S)-2-fluoro-6-methyl-8-oxo-9-(2-oxo-ethyl)-6,7,8,9-tetrahydro-5-oxa-9-aza-benzocyclohepten-7-yl]-carbamic acid tert-butyl ester, MS m/e (%): 353.2 (M+H$^+$, 11), 297.3 (60), 253.2 (100).

b) [(6R,7S)-2-Fluoro-9-(2-hydroxy-ethyl)-6-methyl-8-oxo-6,7,8,9-tetrahydro-5-oxa-9-aza-benzocyclohepten-7-yl]-carbamic acid tert-butyl ester 0.10 g (0.28 mmol) [(6R,7S)-2-Fluoro-6-methyl-8-oxo-9-(2-oxo-ethyl)-6,7,8,9-tetrahydro-5-oxa-9-aza-benzocyclohepten-7-yl]-carbamic acid tert-butyl ester in 4 ml tetrahydrofurane were reduced with 0.02 g (0.34 mmol) sodium borohydride. Chromatography on silicagel with ethylacetate/heptane 8:2 yielded 0.06 g (56%) [(6R,7S)-2-fluoro-9-(2-hydroxy-ethyl)-6-methyl-8-oxo-6,7,8,9-tetrahydro-5-oxa-9-aza-benzocyclohepten-7-yl]-carbamic acid tert-butyl ester, MS m/e (%): 377.3 (M+Na$^+$, 86), 355.2 (M+H$^+$, 14), 255.3 (100).

c) (6R,7S)-7-Amino-2-fluoro-9-(2-hydroxy-ethyl)-6-methyl-6,7-dihydro-9H-5-oxa-9-aza-benzocyclohepten-8-one The title compound was obtained in 50% yield according to the procedure described in example 42b from [(6R,7S)-2-fluoro-9-(2-hydroxy-ethyl)-6-methyl-8-oxo-6,7,8,9-tetrahydro-5-oxa-9-aza-benzocyclohepten-7-yl]-carbamic acid tert-butyl ester, MS m/e (%): 255.3 (M+H$^+$, 100).

d) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide The title compound was obtained in 49% yield according to the procedures described for example 2b using 2,2-dimethyl-N-(2,2,3,3,3-pentafluoro-propyl)-malonamic acid and (6R,7S)-7-amino-2-fluoro-9-(2-hydroxy-ethyl)-6-methyl-6,7-dihydro-9H-5-oxa-9-aza-benzocyclohepten-8-one, MS m/e (%): 517.3 (M+NH$_4^+$, 100), 500.2 (M+H$^+$, 63).

EXAMPLE 54

N-((6R,7S)-9-Allyl-2-fluoro-6-methyl-8-oxo-6,7,8,9-tetrahydro-5-oxa-9-aza-benzocyclohepten-7-yl)-N'-cyclopropylmethyl-2,2-dimethyl-malonamide

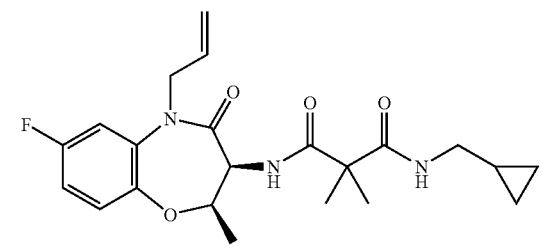

a) N-((6R,7S)-9-Allyl-2-fluoro-6-methyl-8-oxo-6,7,8,9-tetrahydro-5-oxa-9-aza-benzocyclohepten-7-yl)-2,2-dimethyl-malonamic acid ethyl ester The title compound was obtained in 78% yield according to the procedures described for example 2b using 2,2-dimethylmalonic acid monoethyl ester and (6R,7S)-9-allyl-7-amino-2-fluoro-6-methyl-6,7-dihydro-9H-5-oxa-9-aza-benzocyclohepten-8-one, MS m/e (%): 491.2 (M−H$^+$, 100).

b) N-((6R,7S)-9-Allyl-2-fluoro-6-methyl-8-oxo-6,7,8,9-tetrahydro-5-oxa-9-aza-benzocyclohepten-7-yl)-2,2-dimethyl-malonamic acid 0.72 g (1.84 mmol) N-((6R,7S)-9-Allyl-2-fluoro-6-methyl-8-oxo-6,7,8,9-tetrahydro-5-oxa-9-aza-benzocyclohepten-7-yl)-2,2-dimethyl-malonamic acid ethyl ester in 10 ml tetrahydrofurane were treated with 0.08 g (1.84 mmol) lithium hydroxide monohydrate in 3 ml water for 5 hours at room temperature. The tetrahydrofurane was distilled off and the aqueous phase was extracted with diethylether. The water phase was acidified with 1.84 ml 1 N aqueous hydrochloric acid and extracted with ethylacetate to yield 482 mg (72%) N-((6R,7S)-9-allyl-2-fluoro-6-methyl-8-oxo-6,7,8,9-tetrahydro-5-oxa-9-aza-benzocyclohepten-7-yl)-2,2-dimethyl-malonamic acid as white solid, MS m/e (%): 365.0 (M+H$^+$, 100).

c) N-((6R,7S)-9-Allyl-2-fluoro-6-methyl-8-oxo-6,7,8,9-tetrahydro-5-oxa-9-aza-benzocyclohepten-7-yl)-N'-cyclopropylmethyl-2,2-dimethyl-malonamide The title compound was obtained in quantitative yield according to the procedures described for example 2b using N-((6R,7S)-9-allyl-2-fluoro-6-methyl-8-oxo-6,7,8,9-tetrahydro-5-oxa-9-aza-benzocyclohepten-7-yl)-2,2-dimethyl-malonamic acid and cyclopropanemethylamine, MS m/e (%): 416.6 (M−H⁺, 100).

EXAMPLE 55

N-((6R,7S)-9-Allyl-2-fluoro-6-methyl-8-oxo-6,7,8,9-tetrahydro-5-oxa-9-aza-benzocyclohepten-7-yl)-2,2-dimethyl-N'-pyridin-3-ylmethyl-malonamide

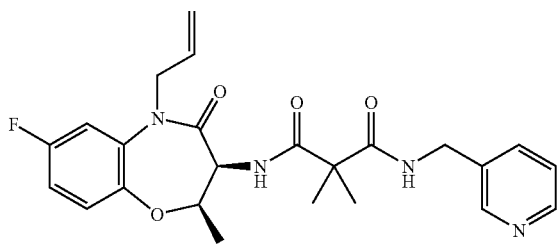

The title compound was obtained in 66% yield according to the procedures described for example 2b using N-((6R,7S)-9-allyl-2-fluoro-6-methyl-8-oxo-6,7,8,9-tetrahydro-5-oxa-9-aza-benzocyclohepten-7-yl)-2,2-dimethyl-malonamic acid and 3-(aminomethyl)pyridine, MS m/e (%): 455.1(M+H⁺, 100).

EXAMPLE 56

{(6R,7S)-2-Fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid methyl ester

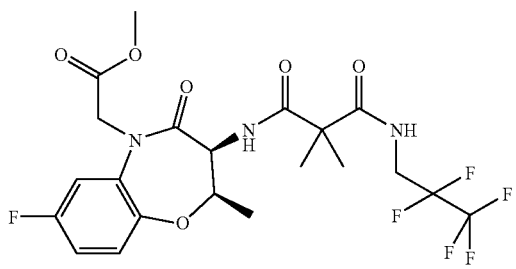

a) ((6R,7S)-7-tert-Butoxycarbonylamino-2-fluoro-6-methyl-8-oxo-7,8-dihydro-6H-5-oxa-9-aza-benzocyclohepten-9-yl)-acetic acid methyl ester 0.30 g (0.97 mmol) ((6R,7S)-2-Fluoro-6-methyl-8-oxo-6,7,8,9-tetrahydro-5-oxa-9-aza-benzocyclohepten-7-yl)-carbamic acid tert-butyl ester in 8 ml dimethylformamide were stirred with 0.14 ml (1.45 mmol) methyl bromoacetate and 0.48 g (1.45 mmol) cesium carbonate overnight. Extraction with water/ethylacetate and chromatography on silicagel with ethylacetate/heptane 1:4 yielded 0.37 g (quant.) ((6R,7S)-7-tert-butoxycarbonylamino-2-fluoro-6-methyl-8-oxo-7,8-dihydro-6H-5-oxa-9-aza-benzocyclohepten-9-yl)-acetic acid methyl ester, MS m/e (%): 383.1 (M+H⁺, 14), 327.3 (24), 283.4 (199).

b) ((6R,7S)-7-Amino-2-fluoro-6-methyl-8-oxo-7,8-dihydro-6H-5-oxa-9-aza-benzocyclohepten-9-yl)-acetic acid methyl ester The title compound was obtained in 77% yield according to the procedures described for example 5e using ((6R,7S)-7-tert-butoxycarbonylamino-2-fluoro-6-methyl-8-oxo-7,8-dihydro-6H-5-oxa-9-aza-benzocyclohepten-9-yl)-acetic acid methyl ester, MS m/e (%): 283.2 (M+H⁺, 100).

c) {(6R,7S)-2-Fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid methyl ester The title compound was obtained in 92% yield according to the procedures described for example 2b using 2,2-dimethyl-N-(2,2,3,3,3-pentafluoro-propyl)-malonamic acid and ((6R,7S)-7-amino-2-fluoro-6-methyl-8-oxo-7,8-dihydro-6H-5-oxa-9-aza-benzocyclohepten-9-yl)-acetic acid methyl ester, MS m/e (%): 528.2 (M+H⁺, 100).

EXAMPLE 57

{(6R,7S)-2-Fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid

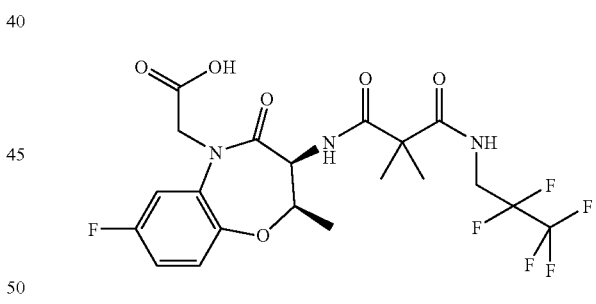

0.10 g (0.19 mmol) {(6R,7S)-2-Fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid methyl ester in 4 ml tetrahydrofurane were stirred with 0.005 g (0.21 mmol) lithium hydroxide in 1 ml water and 0.15 ml methanol for 3 hours. 1N aqueous hydrochloric acid (2 ml) were added. Extraction with ethylacetate and chromatography on silicagel with dichloromethane/methanol 8:2 yielded 0.08 g (78%) {(6R,7S)-2-fluoro-6-methyl-7-[2-methyl-2-(2,2,3,3,3-pentafluoro-propylcarbamoyl)-propionylamino]-8-oxo-7,8-dihydro-6H!-5-oxa-9-aza-benzocyclohepten-9-yl}-acetic acid, MS m/e (%): 514.4 (M+H⁺, 100).

EXAMPLE 58

N-((6R,7S)-9-Carbamoylmethyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoropropyl)-malonamide

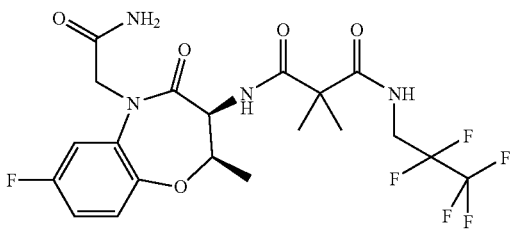

a) ((6R,7S)-9-Carbamoylmethyl-2-fluoro-6-methyl-8-oxo-6,7,8,9-tetrahydro-5-oxa-9-aza-benzocyclohepten-7-yl)-carbamic acid tert-butyl ester The title compound was obtained in 59% yield according to the procedures described for example 56a using ((6R,7S)-2-fluoro-6-methyl-8-oxo-6,7,8,9-tetrahydro-5-oxa-9-aza-benzocyclohepten-7-yl)-carbamic acid tert-butyl ester and 2-bromoacetamide MS m/e (%): 368.1 (M+H$^+$, 26), 312.2 (48), 268 (100).

b) N-((6R,7S)-9-Carbamoylmethyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide ((6R,7S)-9-Carbamoylmethyl-2-fluoro-6-methyl-8-oxo-6,7,8,9-tetrahydro-5-oxa-9-aza-benzocyclohepten-7-yl)-carbamic acid tert-butyl ester was deprotected according to the procedure in example 42b. The resulting 2-((6R,7S)-7-amino-2-fluoro-6-methyl-8-oxo-7,8-dihydro-6H-5-oxa-9-aza-benzocyclohepten-9-yl)-acetamide was reacted with 2,2-dimethyl-N-(2,2,3,3,3-pentafluoro-propyl)-malonamic acid in analogy to the procedure described in example 2b to yield N-((6R,7S)-9-carbamoylmethyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, MS m/e (%): 511.3 (M–H$^+$, 100).

EXAMPLE 59

N-[(6R,7S)-2-Fluoro-6-methyl-9-(2-morpholin-4-yl-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide

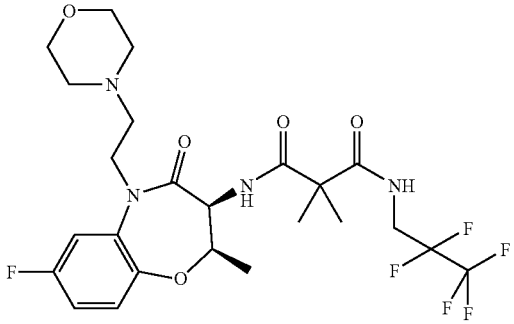

a) [(6R,7S)-2-Fluoro-6-methyl-9-(2-morpholin-4-yl-ethyl)-8-oxo-6,7,8,9-tetrahydro-5-oxa-9-aza-benzocyclohepten-7-yl]-carbamic acid tert-butyl ester 0.10 mg (0.28 mmol) [(6R,7S)-2-Fluoro-6-methyl-8-oxo-9-(2-oxo-ethyl)-6,7,8,9-tetrahydro-5-oxa-9-aza-benzocyclohepten-7-yl]-carbamic acid tert-butyl ester in 4 ml methanol was reacted with 0.036 ml (0.40 mmol) morpholine, 0.07 ml acetic acid and 0.03 g sodium cyanoborohydride at room temperature. Chromatography on silicagel with ethylacetate/heptane 1:1 yielded 0.09 g (73%) [(6R,7S)-2-fluoro-6-methyl-9-(2-morpholin-4-yl-ethyl)-8-oxo-6,7,8,9-tetrahydro-5-oxa-9-aza-benzocyclohepten-7-yl]-carbamic acid tert-butyl ester, MS m/e (%): 424.3 (M+H$^+$, 100).

b) N-[(6R,7S)-2-Fluoro-6-methyl-9-(2-morpholin-4-yl-ethyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide

[(6R,7S)-2-fluoro-6-methyl-9-(2-morpholin-4-yl-ethyl)-8-oxo-6,7,8,9-tetrahydro-5-oxa-9-aza-benzocyclohepten-7-yl]-carbamic acid tert-butyl ester was deprotected according to the procedure in example 42b. The resulting (6R,7S)-7-amino-2-fluoro-6-methyl-9-(2-morpholin-4-yl-ethyl)-6,7-dihydro-9H-5-oxa-9-aza-benzocyclohepten-8-one was reacted with 2,2-dimethyl-N-(2,2,3,3,3-pentafluoro-propyl)-malonamic acid in analogy to the procedure described in example 2b to yield N-[(6R,7S)-2-fluoro-6-methyl-9-(2-morpholin-4-yl-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide, MS m/e (%): 569.3 (M+H$^+$, 100).

EXAMPLE 60

N-((6R,7S)-2-Fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

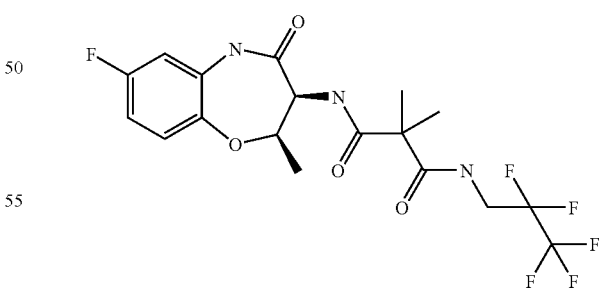

The title compound was obtained in 69% yield according to the procedure described in example 2b) by condensation of (6R,7S)-7-amino-2-fluoro-6-methyl-6,7-dihydro-9H-5-oxa-9-aza-benzocyclohepten-8-one [example 23] with 2,2-dimethyl-N-(2,2,3,3,3-pentafluoro-propyl)-malonamic acid (example 4a) as an off-white solid, MS m/e (%): 456.4 (M+H$^+$, 100).

EXAMPLE 61

2,2-Dimethyl-N-((6R,7S)-6-methyl-8-oxo-3-trifluoromethyl-6,7,8,9-tetrahydro-5-oxa-9-aza-benzocyclohepten-7-yl)-N'-(2,2,3,3,3-pentafluoro-propyl)-malonamide

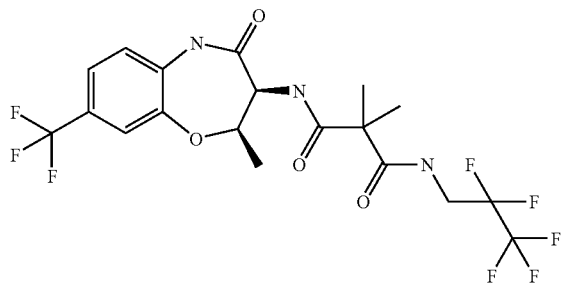

a) (2S,3R)-2-tert-Butoxycarbonylamino-3-(2-nitro-4-trifluoromethyl-phenoxy)-butyric acid In analogous manner to that described in example 5a), the reaction of (2S,3R)-2-tert-butoxycarbonylamino-3-hydroxy-butyric acid and 1-fluoro-2-nitro-4-trifluoromethyl-benzene yielded quantitatively the title compound as a brown oil, MS m/e (%): 426.4(M+NH$_4^+$, 85).

b) (2S,3R)-3-(2-Amino-4-trifluoromethyl-phenoxy)-2-tert-butoxycarbonylamino-butyric acid The title compound was obtained in 88% yield according to the procedure described in example 5b) by hydrogenation of (2S,3R)-2-tert-butoxycarbonylamino-3-(2-nitro-4-trifluoromethyl-phenoxy)-butyric acid as a light brown solid, MS m/e (%): 379.1 (M+H$^+$, 64).

c) ((6R,7S)-6-Methyl-8-oxo-3-trifluoromethyl-6,7,8,9-tetrahydro-5-oxa-9-aza-benzocyclohepten-7-yl)-carbamic acid tert-butyl ester The title compound was obtained in 96% yield according to the procedure described in example 5c) by intramolecular condensation of (2S,3R)-3-(2-amino-4-trifluoromethyl-phenoxy)-2-tert-butoxycarbonylamino-butyric acid as an off-white solid, MS m/e (%): 361.4 (M+H$^+$, 39).

d) (6R,7S)-7-Amino-6-methyl-3-trifluoromethyl-6,7-dihydro-9H-5-oxa-9-aza-benzocyclohepten-8-one The title compound was obtained in 60% yield according to the procedure described in example 5e) by cleavage of the protecting group of ((6R,7S)-6-methyl-8-oxo-3-trifluoromethyl-6,7,8,9-tetrahydro-5-oxa-9-aza-benzocyclohepten-7-yl)-carbamic acid tert-butyl ester as an off-white solid, MS m/e (%): 261.3 (M+H$^+$, 56).

e) 2,2-Dimethyl-N-((6R,7S)-6-methyl-8-oxo-3-trifluoromethyl-6,7,8,9-tetrahydro-5-oxa-9-aza-benzocyclohepten-7-yl)-N'-(2,2,3,3,3-pentafluoro-propyl)-malonamide The title compound was obtained in 90% yield according to the procedure described in example 2b) by condensation of (6R,7S)-7-amino-6-methyl-3-trifluoromethyl-6,7-dihydro-9H-5-oxa-9-aza-benzocyclohepten-8-one with 2,2-dimethyl-N-(2,2,3,3,3-pentafluoro-propyl)-malonamic acid [example 4a)] as alight yellow solid, [α]$_{589}$=−97.17° (c=0.92% in MeOH), MS m/e (%): 506.4 (M+H$^+$, 100).

EXAMPLE 62

2-Methoxy-N-((6R,7S)-6-methyl-8-oxo-3-trifluoromethyl-6,7,8,9-tetrahydro-5-oxa-9-aza-benzocyclohepten-7-yl)-N'-(2,2,3,3,3-pentafluoro-propyl)-malonamide

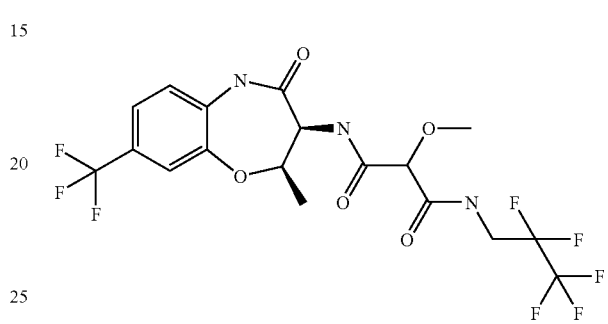

The title compound was obtained in 87% yield according to the procedure described in example 2b) by condensation of (6R,7S)-7-amino-6-methyl-3-trifluoromethyl-6,7-dihydro-9H-5-oxa-9-aza-benzocyclohepten-8-one (example 61d) with 2-methoxy-N-(2,2,3,3,3-pentafluoro-propyl)-malonamic acid [example 41] as alight yellow solid, [α]$_{589}$=−107.05° (c=0.81% in MeOH), MS m/e (%): 508.5(M+H$^+$, 100).

EXAMPLE 63a

N-((6S,7R)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide and

EXAMPLE 63b

N-((6R,7S)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide

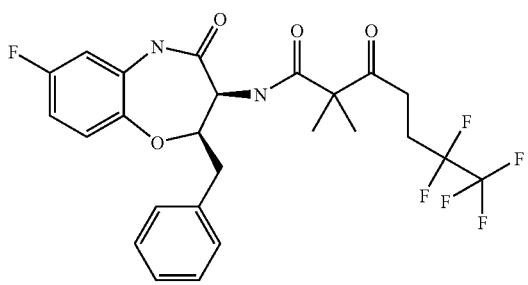

a) racemic (2S,3R and 2R,3S)-2-Dibenzylamino-3-hydroxy-4-phenyl-butyric acid ethyl ester and racemic (2R,3R and 2S,3S)-2-Dibenzylamino-3-hydroxy-4-phenyl-butyric acid ethyl ester A solution of 20 g (70.6 mmol) dibenzylamino-acetic acid ethyl ester in 240 ml tetrahydrofuran was stirred at −78° C. with 38.8 ml (77.6 mmol) lithium diisopropylamide (2M in heptane) for 30 minutes. 17.4 ml (77.6 mmol) phenylacetaldehyde were added and stirring was continued overnight. The mixture was allowed to warm to room temperature, water was added and most of the organic solvent was removed by distillation. About 20 g citric acid were dissolved in the aqueous residue. Extraction with ethylacetate and chromatography on silicagel with ethylacetate/heptane 1/5 yielded as first eluting fraction 5.4 g (19%) racemic (2S,3R and 2R,3S)-2-dibenzylamino-3-hydroxy-4-phenyl-butyric acid ethyl ester, MS m/e (%): 404.3 (M+H$^+$, 100) and as second eluting fraction 4.1 g (15%) racemic (2R,3R and 2S,3S)-2-dibenzylamino-3-hydroxy-4-phenyl-butyric acid ethyl ester, MS m/e (%): 404.3 (M+H$^+$, 100).

b) racemic (2S,3R and 2R,3S)-2-Dibenzylamino-3-hydroxy-4-phenyl-butyric acid To 5.43 g (13.5 mmol) racemic (2S,3R and 2R,3S)-2-dibenzylamino-3-hydroxy-4-phenyl-butyric acid ethyl ester in 75 ml tetrahydrofurane were added 2.28 g (53.8 mmol) lithium hydroxide monohydrate dissolved in 13.5 ml water. The mixture was stirred at 60° C. overnight. Water was added followed by extraction with ethyl acetate. The waterphase was adjusted to pH 1 with 1 N aqueous hydrochloric acid. Extraction with ethylacetate and chromatography on silicagel with dichloromethane/methanol 9/1 yielded 3.50 g (69%) racemic (2S,3R and 2R,3S)-2-dibenzylamino-3-hydroxy-4-phenyl-butyric acid, MS m/e (%): 376.5 (M+H$^+$, 100).

c) racemic (2S,3R and 2R,3S)-2-Dibenzylamino-3-(4-fluoro-2-nitro-phenoxy)-4-phenyl-butyric acid 3.50 g (9.32 mmol) racemic (2S,3R and 2R,3S)-2-dibenzylamino-3-hydroxy-4-phenyl-butyric acid in 14 ml dimethylformamide were added at 0° C. to 0.86 g (19.8 mmol) sodium hydride (55%) in 2 ml dimethylformamide. The suspension was stirred for 2 hours and then 2.25 ml (20.5 mmol) 2,5-difluoro-nitrobenzene in 3.4 ml dimethylformamide were added. After stirring overnight at 0° C. the mixture was poured on ice/water. The pH was adjusted to 1 by adding aqueous hydrochloric acid. Extraction with ethylacetate and chromatography on silicagel with dichloromethane/methanol (100:0 to 95:5) yielded 2.95 g (62%) racemic (2S,3R and 2R,3S)-2-dibenzylamino-3-(4-fluoro-2-nitro-phenoxy)-4-phenyl-butyric acid as yellow oil, MS m/e (%): 515.3 (M+H$^+$, 100).

d) racemic (2S,3R and 2R,3S)-3-(2-Amino-4-fluoro-phenoxy)-2-dibenzylamino-4-phenyl-butyric acid 2.95 g (5.73 mmol) racemic (2S,3R and 2R,3S)-2-dibenzylamino-3-(4-fluoro-2-nitro-phenoxy)-4-phenyl-butyric acid in 59 ml methanol were hydrogenated with 1.76 g Raney-Nickel. Filtration and removal of the solvent by distillation yielded 2.26 g (81%) racemic (2S,3R and 2R,3S)-3-(2-amino-4-fluoro-phenoxy)-2-dibenzylamino-4-phenyl-butyric acid as light yellow oil, MS m/e (%): 485.5 (M+H$^+$, 100).

e) racemic (6S,7R and 6R,7S)-6-Benzyl-7-dibenzylamino-2-fluoro-6,7-dihydro-9H-5-oxa-9-aza-benzocyclohepten-8-one The title compound was obtained in similar yield yield according to the procedures described for example 5c using racemic (2S,3R and 2R,3S)-3-(2-amino-4-fluoro-phenoxy)-2-dibenzylamino-4-phenyl-butyric acid, MS m/e (%): 467.1 (M+H$^+$, 100).

f) (+)-(6S,7R)-6-Benzyl-7-dibenzylamino-2-fluoro-6,7-dihydro-9H-5-oxa-9-aza-benzocyclohepten-8-one and (−)-(6R,7S)-6-Benzyl-7-dibenzylamino-2-fluoro-6,7-dihydro-9H-5-oxa-9-aza-benzocyclohepten-8-one Racemic (6S,7R and 6R,7S)-6-benzyl-7-dibenzylamino-2-fluoro-6,7-dihydro-9H-5-oxa-9-aza-benzocyclohepten-8-one was separated by chiral HPLC on Chiralpak AD with isopropanol/heptane 1/9 to yield the tide compounds.

g) (6S,7R)-7-Amino-6-benzyl-2-fluoro-6,7-dihydro-9H-5-oxa-9-aza-benzocyclohepten-8-one The title compound was prepared by hydrogenation of (+)-(6S,7R)-6-benzyl-7-dibenzylamino-2-fluoro-6,7-dihydro-9H-5-oxa-9-aza-benzocyclohepten-8-one in methanol with Pd/C (10%), MS m/e (%): 287.1 (M+H$^+$, 100).

h) (6R,7S)-7-Amino-6-benzyl-2-fluoro-6,7-dihydro-9H-5-oxa-9-aza-benzocyclohepten-8-one The title compound was prepared by hydrogenation of (−)-(6R,7S)-6-benzyl-7-dibenzylamino-2-fluoro-6,7-dihydro-9H-5-oxa-9-aza-benzocyclohepten-8-one in methanol with Pd/C (10%), MS m/e (%): 287.1 (M+H$^+$, 100).

i) N-((6S7R)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6S,7R)-7-amino-6-benzyl-2-fluoro-6,7-dihydro-9H-5-oxa-9-aza-benzocyclohepten-8-one, MS m/e (%): 532.0 (M+H$^+$, 100).

j) N-((6R,7S)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6R,7S)-7-amino-6-benzyl-2-fluoro-6,7-dihydro-9H-5-oxa-9-aza-benzocyclohepten-8-one, MS m/e (%): 532.0 (M+H$^+$, 100).

EXAMPLE 64a

N-((6R,7R or 6S,7S)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, entity A

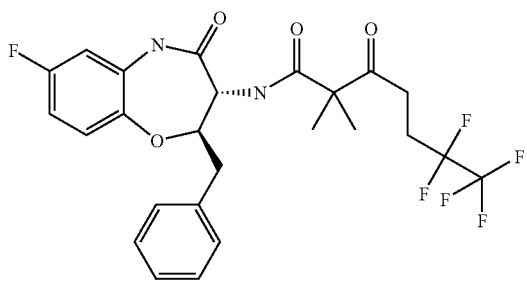

AND EXAMPLE 64b

N-((6S,7S or 6R,7R)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, entity B a) racemic (2R,3R and 2S,3S)-2-Dibenzylamino-3-hydroxy-4-phenyl-butyric acid To 4.12 g (10.2 mmol) racemic (2R,3R and 2S,3S)-2-dibenzylamino-3-hydroxy-4-phenyl-butyric acid ethyl ester in 57 ml tetrahydrofurane were added 1.73 g (40.8 mmol) lithium hydroxide monohydrate dissolved in 10 ml water. The mixture was stirred at 60° C. overnight. Water was added followed by extraction with ethyl acetate. The water-phase was adjusted to pH 1 with 1 N aqueous hydrochloric acid. Extraction with ethylacetate and chromatography on silicagel with dichloromethane/methanol 9/1 yielded 3.40 g (89%) racemic (2R,3R and 2S,3S)-2-dibenzylamino-3-hydroxy-4-phenyl-butyric acid, MS m/e (%): 376.5 (M+H$^+$, 100).

b) racemic (2R,3R and 2S,3S)-2-Dibenzylamino-3-(4-fluoro-2-nitro-phenoxy)-4-phenyl-butyric acid 4.20 g (11.2 mmol) racemic (2R,3R and 2S,3S)-2-dibenzylamino-3-hydroxy-4-phenyl-butyric acid in 14 ml dimethylformamide were added at 0° C. to 1.04 g (23.7 mmol) sodium hydride (55%) in 2.5 ml dimethylformamide. The suspension was stirred for 2 hours and then 2.69 ml (24.6 mmol) 2.5-difluoro-nitrobenzene in 3.5 ml dimethylformamide were added. After stirring overnight at 0° C. the mixture was poured on ice/water. The pH was adjusted to 1 by adding aqueous hydrochloric acid. Extraction with ethylacetate and chromatography on silicagel with dichloromethane/methanol (100:0 to 95:5) yielded 4.02 g (70%) racemic (2R,3R and 2S,3S)-2-dibenzylamino-3-(4-fluoro-2-nitro-phenoxy)-4-phenyl-butyric acid as yellow oil, 1H-NMR (ppm, CDCl$_3$): 2.55–2.63 (m, 1H); 3.54–3.69 (m, 2H); 3.61, 3.66, 3.92, 3.97 (AB, 4H); 4.73–4.80 (m, 1H); 6.14–6.19 (m, 1H); 6.79–6.84 (m,1H); 7.01–7.03 (m, 2H); 7.14–7.16 (m, 3H); 7.2–7.4 (m,11H).

c) racemic (2R,3R and 2S,3S)-3-(2-Amino-4-fluoro-phenoxy)-2-dibenzylamino-4-phenyl-butyric acid 4.02 g (7.81 mmol) racemic (2R,3R and 2S,3S)-2-dibenzylamino-3-(4-fluoro-2-nitro-phenoxy)-4-phenyl-butyric acid in 80 ml methanol were hydrogenated with 2.40 g Raney-Nickel. Filtration and removal of the solvent by distillation yielded 3.36 g (89%) racemic (2R,3R and 2S,3S)-3-(2-amino-4-fluoro-phenoxy)-2-dibenzylamino-4-phenyl-butyric acid as light yellow oil, MS m/e (%): 485.5 (M+H$^+$, 100).

d) racemic (6R,7R and 6S,7S)-6-Benzyl-7-dibenzylamino-2-fluoro-6,7-dihydro-9H-5-oxa-9-aza-benzocyclohepten-8-one The title compound was obtained in similar yield yield according to the procedures described for example 5c using racemic (2R,3R and 2S,3S)-3-(2-amino-4-fluoro-phenoxy)-2-dibenzylamino-4-phenyl-butyric acid, MS m/e (%): 467.5 (M+H$^+$, 100).

e) (+)-(6R,7R or 6S,7S)-6-Benzyl-7-dibenzylamino-2-fluoro-6,7-dihydro-9H-5-oxa-9-aza-benzocyclohepten-8-one and (−)-(6S,7S or 6R,7R)-6-Benzyl-7-dibenzylamino-2-fluoro-6,7-dihydro-9H-5-oxa-9-aza-benzocyclohepten-8-one Racemic (6R,7R and 6S,7S)-6-benzyl-7-dibenzylamino-2-fluoro-6,7-dihydro-9H-5-oxa-9-aza-benzocyclohepten-8-one was separated by chiral HPLC on Chiralpak AD with isopropanol/heptane 1/9 to yield the title compounds.

f) (6R,7R or 6S,7S)-7-Amino-6-benzyl-2-fluoro-6,7-dihydro-9H-5-oxa-9-aza-benzocyclohepten-8-one, entity A The title compound was prepared by hydrogenation of (+)-(6R,7R or 6S,7S)-6-benzyl-7-dibenzylamino-2-fluoro-6,7-dihydro-9H-5-oxa-9-aza-benzocyclohepten-8-one in methanol with Pd/C (10%), MS m/e (%): 287.1 (M+H$^+$, 100).

g) (6S,7S or 6R,7R)-7-Amino-6-benzyl-2-fluoro-6,7-dihydro-9H-5-oxa-9-aza-benzocyclohepten-8-one, entity B The title compound was prepared by hydrogenation of (−)-(6S,7S or 6R,7R)-6-benzyl-7-dibenzylamino-2-fluoro-6,7-dihydro-9H-5-oxa-9-aza-benzocyclohepten-8-one in methanol with Pd/C (10%), MS m/e (%): 287.1 (M+H$^+$, 100).

h) N-((6R,7R or 6S,7S)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, entity A The title compound was obtained according to the procedures described for example 2b using 2,2-dimethyl-N-(2,2,3,3,3-pentafluoro-propyl)-malonamic acid and (6R,7R or 6S,7S)-7-amino-6-benzyl-2-fluoro-6,7-dihydro-9H-5-oxa-9-aza-benzocyclohepten-8-one, entity A, MS m/e (%): 532.0 (M+H$^+$, 100).

i) N-((6S,7S or 6R,7R)-6-Benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, entity B The title compound was obtained according to the procedures described for example 2b using 2,2-dimethyl-N-(2,2,3,3,3-pentafluoro-propyl)-malonamic acid and (6S,7S or 6R,7R)-7-amino-6-benzyl-2-fluoro-6,7-dihydro-9H-5-oxa-9-aza-benzocyclohepten-8-one, entity B. MS m/e (%): 532.0 (M+H$^+$, 100).

EXAMPLE 65a

N-((6S,7R)-6-Cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide

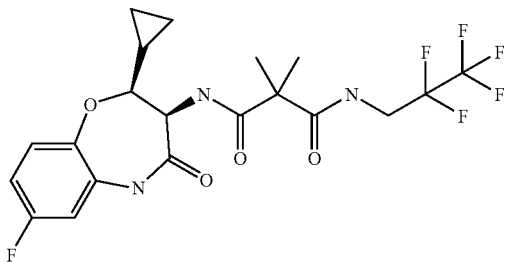

AND EXAMPLE 65b

N-((6R,7S)-6-Cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide

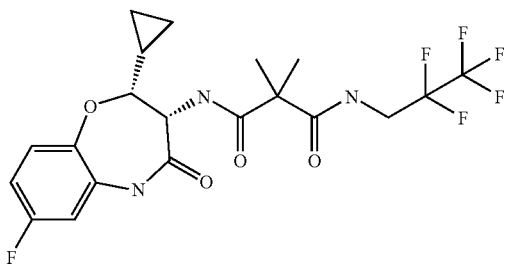

a) racemic (2R,3S and 2S,3R)-3-Cyclopropyl-2-dibenzylamino-3-hydroxy-propionic acid ethyl ester and racemic (2R,3R and 2S,3S)-3-Cyclopropyl-2-dibenzylamino-3-hydroxy-propionic acid ethyl ester A solution of 44.2 g (156 mmol) dibenzylamino-acetic acid ethyl ester in 300 ml tetrahydrofuran was stirred at −70° C. with 92.0 ml (184 mmol) lithium diisopropylamide (2M in heptane) for 60 minutes. 14.0 ml (184 mmol) cyclopropanecarboxaldehyde were added and stirring was continued overnight. The mixture was allowed to warm to room temperature an poured on saturated aqueous ammonium chloride. Extraction with diethyether and chromatography on silicagel with diethyether/heptane 1/2 yielded as first eluting fraction 17.1 g (31%) racemic (2R,3S and 2S,3R)-3-cyclopropyl-2-dibenzylamino-3-hydroxy-propionic acid ethyl ester, MS m/e (%): 354.1 (M+H$^+$, 100) and as second eluting fraction 20.1 g (36%) racemic (2R,3R and 2S,3S)-3-cyclopropyl-2-dibenzylamino-3-hydroxy-propionic acid ethyl ester, MS m/e (%): 354.3 (M+H$^+$, 100).

b) racemic (2R,3S and 2S,3R)-3-Cyclopropyl-2-dibenzylamino-3-hydroxy-propionic acid To 17.1 g (48.5 mmol) racemic (2R,3S and 2S,3R)-3-cyclopropyl-2-dibenzylamino-3-hydroxy-propionic acid ethyl ester in 446 ml tetrahydrofurane were added 8.22 g (194 mmol) lithium hydroxide monohydrate dissolved in 74 ml water. The mixture was stirred at 60° C. overnight. The organic solvent was removed by distillation. Sodium dihydrogenphosphate was added followed by extraction with ethyl acetate. Chromatography on silicagel with diethylether/heptane (1:1 to 1:0) yielded 9.03 g (57%) racemic (2R,3S and 2S,3R)-3-cyclopropyl-2-dibenzylamino-3-hydroxy-propionic acid, MS m/e (%): 326.1 (M+H$^+$, 100).

c) racemic (2R,3S and 2S,3R)-3-Cyclopropyl-2-dibenzylamino-3-(4-fluoro-2-nitro-phenoxy)-propionic acid 1.30 g (4.00 mmol) racemic (2R,3S and 2S,3R)-3-Cyclopropyl-2-dibenzylamino-3-hydroxy-propionic acid in 4 ml dimethylformamide were added at 0° C. to 0.37 g (8.48 mmol) sodium hydride (55%) in 4 ml dimethylformamide. The suspension was stirred for 2 hours and then 0.96 ml (8.8 mmol) 2,5-difluoro-nitrobenzene in 3.4 ml dimethylformamide were added. After stirring overnight the mixture was poured on ice/water. The pH was adjusted to 1 by adding aqueous hydrochloric acid. Extraction with ethylacetate and chromatography on silicagel with diethylether/heptane (25:75 to 100:0) yielded 1.57 g (85%) racemic (2R,3S and 2S,3R)-3-cyclopropyl-2-dibenzylamino-3-(4-fluoro-2-nitro-phenoxy)-propionic acid as light yellow foam, MS m/e (%): 465.0 (M+H$^+$, 100).

d) racemic (2R,3S and 2S,3R)-3-(2-Amino-4-fluoro-phenoxy)-3-cyclopropyl-2-dibenzylamino-propionic acid 1.47 g (3.17 mmol) racemic (2R,3S and 2S,3R)-3-Cyclopropyl-2-dibenzylamino-3-(4-fluoro-2-nitro-phenoxy)-propionic acid in 50 ml methanol were hydrogenated with 0.37 g Raney-Nickel. Filtration and removal of the solvent by distillation yielded 1.22 g (89%) racemic (2R,3S and 2S,3R)-3-(2-amino-4-fluoro-phenoxy)-3-cyclopropyl-2-dibenzylamino-propionic acid as light grey foam, MS m/e (%): 435.1 (M+H$^+$, 100).

e) racemic (6S,7R and 6R,7S)-6-Cyclopropyl-7-dibenzylamino-2-fluoro-6,7-dihydro-9H-5-oxa-9-aza-benzocyclohepten-8-one The title compound was obtained in 49% yield yield according to the procedures described for example 5c using racemic (2R,3S and 2S,3R)-3-(2-amino-4-fluoro-phenoxy)-3-cyclopropyl-2-dibenzylamino-propionic acid, MS m/e (%): 415.0 (M+H$^+$, 100).

f) (+)-(6S,7R)-6-Cyclopropyl-7-dibenzylamino-2-fluoro-6,7-dihydro-9H-5-oxa-9-aza-benzocyclohepten-8-one and (−)-(6R,7S)-6-Cyclopropyl-7-dibenzylamino-2-fluoro-6,7-dihydro-9H-5-oxa-9-aza-benzocyclohepten-8-one Racemic (6S,7R and 6R,7S)-6-Cyclopropyl-7-dibenzylamino-6,7-dihydro-9H-5-oxa-9-aza-benzocyclohepten-8-one was separated by chiral HPLC on Chiralpak AD with isopropanol/heptane 1/9 to yield the title compounds.

g) (6S,7R)-7-Amino-6-cyclopropyl-2-fluoro-6,7-dihydro-9H-5-oxa-9-aza-benzocyclohepten-8-one The title compound was prepared by hydrogenation of (+)-(6S,7R)-6-cyclopropyl-7-dibenzylamino-2-fluoro-6,7-dihydro-9H-5-oxa-9-aza-benzocyclohepten-8-one in methanol with Pd/C (10%), MS m/e (%): 235.1 (M−H, 100).

h) (6R,7S)-7-Amino-6-cyclopropyl-2-fluoro-6,7-dihydro-9H-5-oxa-9-aza-benzocyclohepten-8-one The title compound was prepared by hydrogenation of (−)-(6R,7S)-6-cyclopropyl-7-dibenzylamino-2-fluoro-6,7-dihydro-9H-5-oxa-9-aza-benzocyclohepten-8-one in methanol with Pd/C (10%), MS m/e (%): 235.1 (M+H⁺, 100).

i) N-((6S,7R)-6-Cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6S,7R)-7-amino-6-cyclopropyl-2-fluoro-6,7-dihydro-9H-5-oxa-9-aza-benzocyclohepten-8-one, MS m/e (%): 482.5 (M+H⁺, 100).

j) N-((6R,7S)-6-Cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6R,7S)-7-amino-6-cyclopropyl-2-fluoro-6,7-dihydro-9H-5-oxa-9-aza-benzocyclohepten-8-one, MS m/e (%): 482.0 (M+H⁺, 100).

EXAMPLE 65c (+)-N-((6S,7S or 6R,7R)-6-Cyclopropyl-2-fluoro-8-oxo-6,7,8,9-tetrahydro-5-oxa-9-aza-benzocyclohepten-7-yl)-2,2-dimethyl-N'-(2,2,3,3,3-pentafluoropropyl)-malonamide, entity A

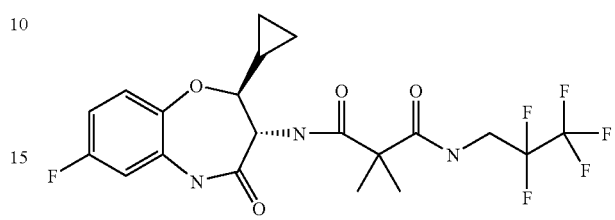

AND EXAMPLE 65d (−)-N-((6R,7R or 6S,7S)-6-Cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoropropyl)-malonamide, entity B The compounds of example 65c and 65d were prepared in analogy to example 65a and 65b but from racemic (2R,3R and 2S,3S)-3-cyclopropyl-2-dibenzylamino-3-hydroxy-propionic acid ethyl ester, MS m/e (%): 482.5 (M+H⁺, 100).

EXAMPLE 66a

N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, entity A AND EXAMPLE 66b N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, entity B

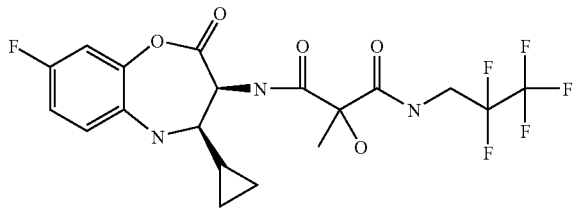

a) 2-Hydroxy-2-methyl-malonic acid monoethyl ester

To a solution of 3.52 g (20 mmol) diethyl methylmalonate in 40 ml dimethylformamide were added 13.1 g (40 mmol) cesium carbonate. The suspension was stirred at room temperature and air was bubbled in for 1 hour. The mixture was poured into water and extracted with ethylacetate. Extraction at pH 1 with ethylacetate yielded 2.28 g (70%) 2-hydroxy-2-methyl-malonic acid monoethyl ester, light yellow liquid, MS m/e (%): 161.0 (M−H, 100).

b) 2-Hydroxy-2-methyl-N-(2,2,3,3,3-pentafluoro-propyl)-malonamic acid ethyl ester To a solution of 2.08 g (12.8 mmol) 2-hydroxy-2-methyl-malonic acid monoethyl ester in 50 ml of tetrahydrofuran 1.39 g (12.8 mmol) of 2,2,3,3,3-pentafluoropropylamine, 2.51 g (12.8 mmol) of N-(3-dimethylaminopropyl)-N'-ethylcarbodiimide hydrochloride, 1.77 g (12.8 mmol) of 1-hydroxybenzotrizole hydrate and 4.48 ml (25.7 mmol) of N,N-diisopropyl-ethylamine were added. The mixture was stirred at room temperature for 18 h. Silicagel was added and the solvent was removed by distillation. The residue was purified by chromatography on silicagel (ethyl acetate/heptane=0:100 to 50:50) to yield 3.01 g (80%) of the title compound as white solid, MS m/e (%): 292.1 (M–H+, 100).

c) 2-Hydroxy-2-methyl-N-(2,2,3,3,3-pentafluoro-propyl)-malonamic acid

To a solution of 2.91 g (9.93 mmol) 2-hydroxy-2-methyl-N-(2,2,3,3,3-pentafluoro-propyl)-malonamic acid ethyl ester in 50 ml of tetrahydrofurane were added 0.42 g (9,92 mmol) of lithium hydroxide in 20 ml of water and the mixture was stirred overnight at room temperature. After concentration in vacuo water (50 ml) was added and the mixture was acidified to pH 1. Extraction with ethylacetate gave 2.46 g (94%) of the title compound as a solid, MS m/e (%): 263.9 (M–H, 100).

d) N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, entity A and Entity B N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide was obtained as mixture of epimers according to the procedures described for example 2b using racemic 2-hydroxy-2-methyl-N-(2,2,3,3,3-pentafluoro-propyl)-malonamic acid and (6R,7S)-7-amino-6-cyclopropyl-2-fluoro-6,7-dihydro-9H-5-oxa-9-aza-benzocyclohepten-8-one. The epimers were separated by chromatography on Chiralpak AD using isopropanol/heptane 15:85 to yield (–)-N-((6R,7S)-6-cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, entity A, MS m/e (%): 484.5 (M+H+, 100), as first eluting fraction, and (–)-N-((6R, 7S)-6-cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, entity B, as second eluting fraction, MS m/e (%): 484.5 (M+H+, 100).

EXAMPLE 67

Racemic N-((6R,7S and 6S,7R)-6-Cyclopropyl-2-fluoro-8-oxo-6,7,8,9-tetrahydro-5-oxa-9-aza-benzocyclohepten-7-yl)-N'-(3,5-difluoro-benzyl)-2,2-dimethyl-malonamide

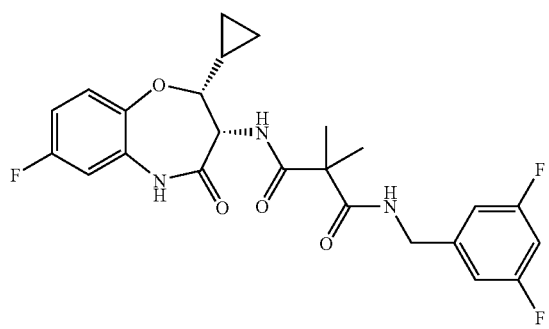

a) N-(3,5-difluoro-benzyl)-2,2-dimethyl-malonamic acid

N-(3,5-difluoro-benzyl)-2,2-dimethyl-malonamic acid was obtained in comparable yields according to the procedures described for 2-methyl-N-(2,2,3,3,3-pentafluoro-propyl)-malonamic acid (see example 1) using diethyl-2,2-dimethyl-malonate instead of diethyl methyl-malonate in step a) and 3,5-difluorobenzylamine instead of 2,2,3,3,3-pentafluoropropylamine in step b), MS m/e (%): 258.1 (M+H+, 100).

b) Racemic N-((6R,7S and 6S,7R)-6-Cyclopropyl-2-fluoro-8-oxo-6,7,8,9-tetrahydro-5-oxa-9-aza-benzocyclohepten-7-yl)-N'-(3,5-difluoro-benzyl)-2,2-dimethyl-malonamide The title compound was obtained according to the procedures described for example 2b using N-(3,5-difluoro-benzyl)-2,2-dimethyl-malonamic acid and racemic (6R,7S and 6S,7R)-7-amino-6-cyclopropyl-2-fluoro-6,7-dihydro-9H-5-oxa-9-aza-benzocyclohepten-8-one, MS m/e (%): 476.1 (M+H+, 100).

EXAMPLE 68a

N-((S)-2-Fluoro-6,6-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamid

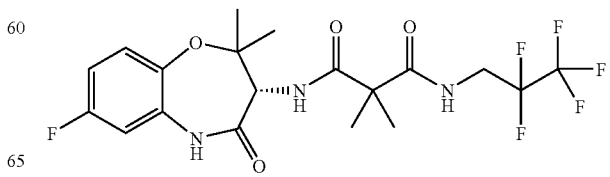

AND EXAMPLE 68b

N-((R)-2-Fluoro-6,6-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide a) 2-Dibenzylamino-3-hydroxy-3-methyl-butyric acid ethyl ester

A solution of 11.3 g (40.0 mmol) dibenzylamino-acetic acid ethyl ester in 107 ml tetrahydrofuran and 107 ml toluene was stirred at −70° C. with 22 ml (44 mmol) lithium diisopropylamide (2M in heptane) for 30 minutes. 3.40 ml (46 mmol) acetone were added and stirring was continued overnight. The mixture was allowed to warm to room temprature, aqueous ammonium chloride solution was added. Extraction with diethylether and chromatography on silicagel with diethylether/heptane 1/2 yielded 7.16 g (52%) 2-dibenzylamino-3-hydroxy-3-methyl-butyric acid ethyl ester, MS m/e (%): 342.3 (M+H$^+$, 100).

b) 2-Dibenzylamino-3-hydroxy-3-methyl-butyric acid

To 2.90 g (8.49 mmol) 2-dibenzylamino-3-hydroxy-3-methyl-butyric acid ethyl ester in 300 ml methanol were added 3.21 g (51.0 mmol) potassium hydroxide dissolved in 100 ml water. The mixture was stirred at 60° C. overnight. 500 ml saturated, aqueous sodium dihydrogenphosphate solution were added followed by extraction with ethyl acetate. Chromatography on silicagel with ethylacetate/heptan (50:50 to 100:0) yielded 1.41 g (53%) 2-dibenzylamino-3-hydroxy-3-methyl-butyric acid, MS m/e (%): 312.3 (M−H, 100).

c) 2-Dibenzylamino-3-(4-fluoro-2-nitro-phenoxy)-3-methyl-butyric acid 1.41 g (4.51 mmol) 2-dibenzylamino-3-hydroxy-3-methyl-butyric acid and 0.54 ml (4.95 mmol) 2,5-difluoronitrobenzene in 46 ml tetrahydrofuran were treated at 0° C. with 19.8 ml (9.9 mmol) potassium bis(trimethylsilyl)amide (0.5 M in toluene). The solution was stirred overnight at room temperature and was then poured on ice/water. Extraction with ethylacetate and chromatography on silicagel with diethylether/heptane (30:70 to 75:25) and yielded 0.40 g (20%) 2-dibenzylamino-3-(4-fluoro-2-nitro-phenoxy)-3-methyl-butyric acid as yellow solid, MS m/e (%): 453.4 (M+H$^+$, 100).

d) 3-(2-Amino-4-fluoro-phenoxy)-2-dibenzylamino-3-methyl-butyric acid 0.10 g (0.22 mmol) 2-dibenzylamino-3-(4-fluoro-2-nitrophenoxy)-3-methyl-butyric acid in 3.4 ml methanol were hydrogenated with 0.03 g Raney-Nickel. Filtration and removal of the solvent by distillation yielded 0.09 g (93%) 3-(2-amino-4-fluoro-phenoxy)-2-dibenzylamino-3-methyl-butyric acid as colorless solid, MS m/e (%): 423.3 (M+H$^+$, 100).

e) 7-Dibenzylamino-2-fluoro-6,6-dimethyl-6,7-dihydro-9H-5-oxa-9-aza-benzocyclohepten-8-one The title compound was obtained in similar yield yield according to the procedures described for example 5c using 3-(2-amino-4-fluoro-phenoxy)-2-dibenzylamino-3-methyl-butyric acid, MS m/e (%): 405.5 (M+H$^+$, 100).

f) (−)-(S)-7-Dibenzylamino-2-fluoro-6,6-dimethyl-6,7-dihydro-9H-5-oxa-9-aza-benzocyclohepten-8-one and (+)-(R)-7-Dibenzylamino-2-fluoro-6,6-dimethyl-6,7-dihydro-9H-5-oxa-9-aza-benzocyclohepten-8-one Racemic 7-dibenzylamino-2-fluoro-6,6-dimethyl-6,7-dihydro-9H-5-oxa-9-aza-benzocyclohepten-8-one was separated by chiral HPLC on Chiralpak AD with isopropanol/heptane 20:80 to yield the title compounds.

g) (S)-7-Amino-2-fluoro-6,6-dimethyl-6,7-dihydro-9H-5-oxa-9-aza-benzocyclohepten-8-one The title compound was prepared by hydrogenation of (−)-(S)-7-dibenzylamino-2-fluoro-6,6-dimethyl-6,7-dihydro-9H-5-oxa-9-aza-benzocyclohepten-8-one in methanol with Pd/C (10%), MS m/e (%): 225.3 (M+H$^+$, 100).

h) (R)-7-Amino-2-fluoro-6,6-dimethyl-6,7-dihydro-9H-5-oxa-9-aza-benzocyclohepten-8-one The title compound was prepared by hydrogenation of (+)-(R)-7-dibenzylamino-2-fluoro-6,6-dimethyl-6,7-dihydro-9H-5-oxa-9-aza-benzocyclohepten-8-one in methanol with Pd/C (10%), MS m/e (%): 225.3 (M+H$^+$, 100).

i) N-((S)-2-Fluoro-6,6-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamid The title compound was obtained according to the procedures described for example 2b using 2,2-dimethyl-N-(2,2,3,3,3-pentafluoro-propyl)-malonamic acid and (S)-7-amino-2-fluoro-6,6-dimethyl-6,7-dihydro-9H-5-oxa-9-aza-benzocyclohepten-8-one, MS m/e (%): 470.5 (M+H$^+$, 100).

j) N-((R)-2-Fluoro-6,6-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (R)-7-amino-2-fluoro-6,6-dimethyl-6,7-dihydro-9H-5-oxa-9-aza-benzocyclohepten-8-one, MS m/e (%): 470.5 (M+H$^+$, 100).

EXAMPLE 69a

N-((6R,7S)-6-Ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

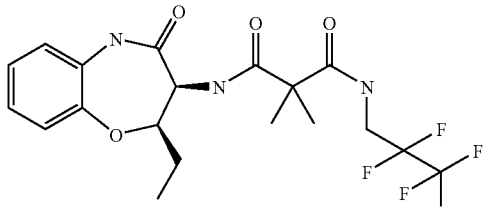

AND EXAMPLE 69b

N-((6S,7R)-6-Ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide

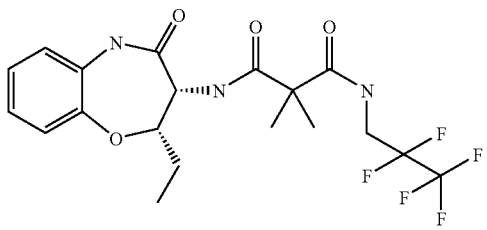

a) 2-tert-Butoxycarbonylamino-3-(2-nitro-phenoxy)-pentanoic acid 7.05 g (30.2 mmol) 2-tert-Butoxycarbonylamino-3-hydroxy-pentanoic acid in 7 ml dimethylformamide were added at 0° C. to 2.80 g (64.1 mmol) sodium hydride (55%) in 56 ml dimethylformamide. The suspension was stirred for 2 hours and then 3.54 ml (33.2 mmol) 1-fluoro-2-nitrobenzene were added. After stirring for 2 days the mixture was poured on ice/water and extracted with diethylether. The pH was adjusted to 1 by adding aqueous hydrochloric acid. Extraction with ethylacetate and chromatography on silicagel with ethylacetate/heptane 1/1 yielded 6.03 g (56%) 2-tert-butoxycarbonylamino-3-(2-nitro-phenoxy)-pentanoic acid as orange oil, MS m/e (%): 353.4 (M–H, 100).

b) 3-(2-Amino-phenoxy)-2-tert-butoxycarbonylamino-pentanoic acid 6.03 g (17.0 mmol) 2-tert-butoxycarbonylamino-3-(2-nitro-phenoxy)-pentanoic acid in 110 ml methanol were hydrogenated with 0.21 g Palladium 10% on charcoal. Filtration and removal of the solvent by distillation yielded 5.22 g (95%) 3-(2-amino-phenoxy)-2-tert-butoxycarbonylamino-pentanoic acid as red oil, MS m/e (%): 325.3 (M+H$^+$, 100).

c) ((6R,7S)-6-Ethyl-8-oxo-6,7,8,9-tetrahydro-5-oxa-9-aza-benzocyclohepten-7-yl)-carbamic acid tert-butyl ester and ((6S,7R)-6-Ethyl-8-oxo-6,7,8,9-tetrahydro-5-oxa-9-aza-benzocyclohepten-7-yl)-carbamic acid tert-butyl ester 5.22 g (16.0 mmol) 3-(2-Amino-phenoxy)-2-tert-butoxycarbonylamino-pentanoic acid and 3.12 g (15.9 mmol) N-(3-dimethylaminopropyl)-N'-ethyl-carbodiimid-hydrochloride in 71 ml dimethylformamide were stirred overnight at room temperature. Extraction with saturated aqueous sodium hydrogencarbonate/ethylacetate and chromatography on silicagel with ethylacetate/heptane 1:2 followed by chromatography on Chiralpak AD with heptane/ethanol 80:20 yielded 0.46 g (–)-((6R,7S)-6-ethyl-8-oxo-6,7,8,9-tetrahydro-5-oxa-9-aza-benzocyclohepten-7-yl)-carbamic acid tert-butyl ester, [1H-NMR (ppm, CDCl3): 1.11(t, 3H), 1.42 (s, 9H), 1.5–1.9 (m, 2H), 4.53–4.62 (m, 1H), 4.76 (mc, 1H), 5.57 (d, 1H), 6.94–6.97 (m, 1H), 7.0–7.1 (m, 1H), 7.1–7.18 (m, 2H), 8.08 (broad, 1H)], and 590 mg (+)-((6S,7R)-6-ethyl-8-oxo-6,7,8,9-tetrahydro-5-oxa-9-aza-benzocyclohepten-7-yl)-carbamic acid tert-butyl ester, [1H-NMR (ppm, CDCl3): 1.11(t, 3H), 1.42 (s, 9H), 1.5–1.9 (m, 2H), 4.53–4.62 (m, 1H), 4.76 (mc, 1H), 5.57 (d, 1H), 6.94–6.97 (m, 1H), 7.0–7.1 (m, 1H), 7.1–7.18 (m, 2H), 7.39 (broad, 1H)].

d) (6S,7R)-7-Amino-6-ethyl-6,7-dihydro-9H-5-oxa-9-aza-benzocyclohepten-8-one

The title compound was prepared in quantitative yield by reaction of 590 mg (1.93 mmol) ((6S,7R)-6-ethyl-8-oxo-6,7,8,9-tetrahydro-5-oxa-9-aza-benzocyclohepten-7-yl)-carbamic acid tert-butyl ester with 2.86 g (29 mmol) ortho phosphoric acid in 6 ml tetrahydrofurane, MS m/e (%): 207.1 (M+H$^+$, 100).

e) (6R,7S)-7-Amino-6-ethyl-6,7-dihydro-9H-5-oxa-9-aza-benzocyclohepten-8-one

The title compound was prepared in 81% yield by reaction of 460 mg (1.50 mmol) ((6R,7S)-6-ethyl-8-oxo-6,7,8,9-tetrahydro-5-oxa-9-aza-benzocyclohepten-7-yl)-carbamic acid tert-butyl ester with 2.23 g (22.5 mmol) ortho phosphoric acid in 4 ml tetrahydrofurane, MS m/e (%): 207.1 (M+H$^+$, 100).

f) N-((6S,7R)-6-Ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6S,7R)-7-amino-6-ethyl-6,7-dihydro-9H-5-oxa-9-aza-benzocyclohepten-8-one, MS m/e (%): 452.1 (M+H$^+$, 100).

g) N-((6R,7S)-6-Ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6R,7S)-7-amino-6-ethyl-6,7-dihydro-9H-5-oxa-9-aza-benzocyclohepten-8-one, MS m/e (%): 452.1 (M+H$^+$, 100).

EXAMPLE 70a

N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3-pentafluoro-propyl)-malonamide, entity A

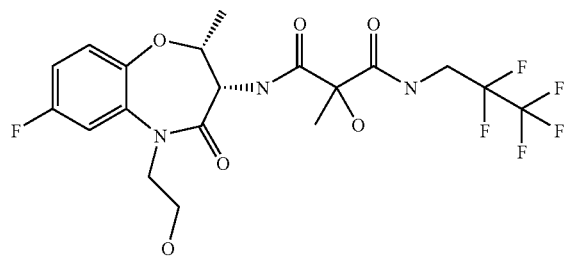

AND EXAMPLE 70b

N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3-pentafluoro-propyl)-malonamide, entity B a) N-((6R,7S)-9-Allyl-2-fluoro-6-methyl-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide The title compound was obtained according to the procedures described for example 2b using 2-hydroxy-2-methyl-N-(2,2,3,3,3-pentafluoro-propyl)-malonamic acid and (6R,7S)-9-allyl-7-amino-2-fluoro-6-methyl-6,7-dihydro-9H-5-oxa-9-aza-benzocyclohepten-8-one, MS m/e (%): 498.5 (M+H$^+$, 100).

b) N-[(6R,7S)-2-Fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide A solution of 1.30 g (3 mmol) (6R,7S)-9-allyl-7-amino-2-fluoro-6-methyl-6,7-dihydro-9H-5-oxa-9-aza-benzocyclohepten-8-one in 60 ml dichloromethane was treated with ozone at −75° C. for 60 minutes. Methyl sulfide, 0.81 g (13 mmol), was added and the solution was stirred for 16 hours at room temperature. The solvent was distilled off under vacuum and the residue was chromatographed in silicagel with n-heptane/ethylacetate 100:0 to 0:100 to yield 1.07 g (82%) N-[(6R,7S)-2-fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide, MS m/e (%): 500.3 (M+H$^+$, 100).

c) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide 1.00 g (2.0 mmol N-[(6R,7S)-2-Fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide in 30 ml tetrahydrofurane were reduced with 0.09 g (2.0 mmol) sodium borohydride. Chromatography on silicagel with ethylacetate/heptane 0:100 to 100:0 yielded 0.33 g (34%) N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide, MS m/e (%): 502.0 (M+H$^+$, 100).

d) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, entity A and N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, entity B 0.31 g (1.0 mmol) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide epimers were separated by chromatography on Chiralpak AD with isopropanol/heptane 15:85 to yield 0.11 g N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, entity A, MS m/e (%): 502.3 (M+H$^+$, 100) and 0.08 g N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, entity B, MS m/e (%): 502.1 (M+H$^+$, 100).

EXAMPLE 71a

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity A

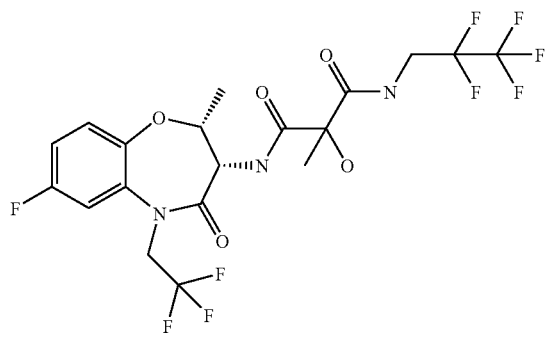

AND EXAMPLE 71b

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity B a) [(6R,7S)-2-Fluoro-6-methyl-8-oxo-9-(2,2,2-trifluoro-ethyl-6,7,8,9-tetrahydro-5-oxa-9-aza-benzocyclohepten-7-yl]-carbamic acid tert-butyl ester A solution of 3.00 g (10.0 mmol) ((6R,7S)-2-fluoro-6-methyl-8-oxo-6,7,8,9-tetrahydro-5-oxa-9-aza-benzocyclohepten-7-yl)-carbamic acid tert-butyl ester and 3.37 g (15.0 mmol) 2,2,2-trifluoroethyl triflate in 30 ml dimethylformamide were treated with 4.73 g (15.0 mmol) cesium carbonate for 6 hours. The solvent was distilled off at low pressure and the residue was extracted with water/ethylacetate. Chromatography on silicagel with heptane/ethylacetate 100:0 to 0:100 yielded 3.79 g (99%) [(6R,7S)-2-fluoro-6-methyl-8-oxo-9-(2,2,2-trifluoro-ethyl)-6,7,8,9-tetrahydro-5-oxa-9-aza-benzocyclohepten-7-yl]-carbamic acid tert-butyl ester, MS m/e (%): 393.3 (M+H$^+$, 100).

b) (6R,7S)-7-Amino-2-fluoro-6-methyl-9-(2,2,2-trifluoro-ethyl)-6,7-dihydro-9H-5-oxa-9-aza-benzocyclohepten-8-one The title compound was prepared in 75% yield by reaction of 3.70 g (9.0 mmol) [(6R,7S)-2-fluoro-6-methyl-8-oxo-9-(2,2,2-trifluoro-ethyl)-6,7,8,9-tetrahydro-5-oxa-9-aza-benzocyclohepten-7-yl]-carbamic acid tert-butyl ester with 18 ml trifluoroacetic acid in 75 ml dichloromethane, MS m/e (%): 293.1 (M+H$^+$, 100).

c) N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide The title compound was obtained as mixture of epimers according to the procedures described for example 2b using racemic 2-hydroxy-2-methyl-N-(2,2,3,3,3-pentafluoro-propyl)-malonamic acid and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 504.0 (M+H$^+$, 100).

d) N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity A and N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity B Epimeric N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide was separated by chromatography on Chiralpak AD using ethanol/heptane 10:90 to yield (−)-N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity A, MS m/e (%): 540.3 (M+H$^+$, 100), as first eluting fraction, and (−)-N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, entity B, as second eluting fraction, MS m/e (%): 540.3 (M+H$^+$, 100).

EXAMPLE 72a

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity A

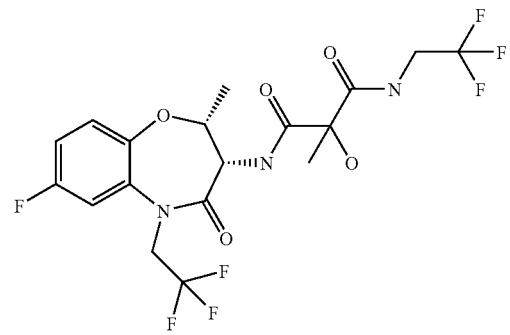

AND EXAMPLE 72b

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity B a) 2-Hydroxy-2-methyl-N-(2,2,2-trifluoro-ethyl)-malonamic acid ethyl ester RO5026120

To a solution of 31.5 g (15.5 mmol) 2-hydroxy-2-methyl-malonic acid monoethyl ester in 400 ml of tetrahydrofuran 16.9 g (17.1 mmol) of 2,2,2-trifluoroethylamine, 32.7 g (17.1 mmol) of N-(3-dimethylaminopropyl)-N'-ethylcarbodiimide hydrochloride, 23.1 g (17.1 mmol) of 1-hydroxybenzotrizole hydrate and 58.1 ml (34.2 mmol) of N,N-diisopropyl-ethylamine were added. The mixture was stirred at room temperature for 18 h. The solvent was removed by distillation and the residue was extracted with water/ethylacetate. Chromatography on silicagel with heptane/ethylacetate 1:1 yielded 25.4 g (67%) 2-hydroxy-2-methyl-N-(2,2,2-trifluoroethyl)-malonamic acid ethyl ester, MS m/e (%): 242.1 (M−H, 100).

b) (S or R)-2-Hydroxy-2-methyl-N-(2,2,2-trifluoro-ethyl)-malonamic acid ethyl ester, entity A and (S or R)-2-Hydroxy-2-methyl-N-(2,2,2-trifluoro-ethyl)-malonamic acid ethyl ester, entity B Racemic 2-hydroxy-2-methyl-N-(2,2,2-trifluoro-ethyl)-malonamic acid ethyl ester was separated by chromatography on Chiralpak AD with heptane/ethanol to yield (−)-(S or R)-2-hydroxy-2-methyl-N-(2,2,2-trifluoro-ethyl)-malonamic acid ethyl ester, entity A, MS m/e (%): 242.3 (M–H, 100), as the first eluting fraction and (+)-(S or R)-2-hydroxy-2-methyl-N-(2,2,2-trifluoro-ethyl)-malonamic acid ethyl ester, entity B, MS m/e (%): 242.4 (M–H, 100), as second eluting fraction.

c) (S or R)-2-Hydroxy-2-methyl-N-(2,2,2-trifluoro-ethyl)-malonamic acid, entity A To a solution of 3.60 g (15.0 mmol) (S or R)-2-hydroxy-2-methyl-N-(2,2,2-trifluoro-ethyl)-malonamic acid ethyl ester, entity A, in 50 ml of tetrahydrofurane were added 0.65 g (16 mmol) of lithium hydroxide in 25 ml of water and the mixture was stirred for 18 hours at room temperature. After removal of the organic solvent by distillation the mixture was acidified to pH 1. Extraction with ethylacetate gave 2.70 g (85%) of the title compound as an oil, MS m/e (%): 214.3 (M–H, 100).

d) (S or R)-2-Hydroxy-2-methyl-N-(2,2,2-trifluoro-ethyl)-malonamic acid, entity B To a solution of 3.680 g (16.0 mmol) (S or R)-2-hydroxy-2-methyl-N-(2,2,2-trifluoro-ethyl)-malonamic acid ethyl ester, entity B. in 50 ml of tetrahydrofurane were added 0.69 g (16 mmol) of lithium hydroxide in 25 ml of water and the mixture was stirred for 18 hours at room temperature. After removal of the organic solvent by distillation the mixture was acidified to pH 1. Extraction with ethylacetate gave 3.00 g (89%) of the title compound as an oil, MS m/e (%): 213.9 (M–H, 100).

e) N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide, epimer A The title compound was obtained according to the procedures described for example 2b using (S or R)-2-hydroxy-2-methyl-N-(2,2,2-trifluoro-ethyl)-malonamic acid, entity B, and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 490.0 (M+H+, 100).

f) N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide, epimer B The title compound was obtained according to the procedures described for example 2b using (S or R)-2-hydroxy-2-methyl-N-(2,2,2-trifluoro-ethyl)-malonamic acid, entity A, and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 490.0 (M+H+, 100).

EXAMPLE 73a

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, entity A

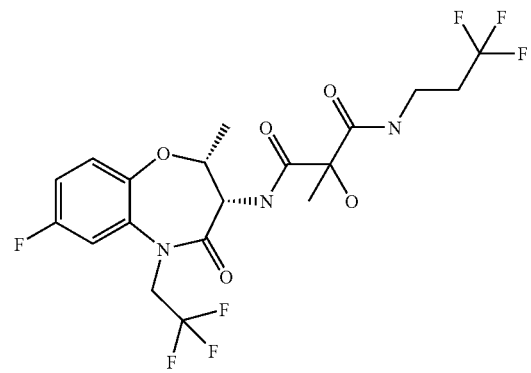

AND EXAMPLE 73b

N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, entity B 2-Hydroxy-2-methyl-N-(3,3,3-trifluoro-propyl)-malonamic acid ethyl ester To a solution of 2.00 g (8.51 mmol) 2-hydroxy-2-methyl-malonic acid monoethyl ester in 60 ml of tetrahydrofuran 1.27 g (8.51 mmol) of 3,3,3-trifluoropropylamine hydrochloride, 1.67 g (8.51 mmol) of N-(3-dimethylaminopropyl)-N'-ethylcarbodiimide hydrochloride, 1.17 g (8.51 mmol) of 1-hydroxybenzotrizole hydrate and 4.46 ml (25.5 mmol) of N,N-diisopropyl-ethylamine were added. The mixture was stirred at room temperature for 18 h. Silicagel was added and the solvent was removed by distillation. The residue was purified by chromatography on silicagel dichloromethane/methanol 7:3 to yield 2.33 g (94%) of the title compound, MS m/e (%): 258.1 (M+H+, 100).

b) 2-Hydroxy-2-methyl-N-(3,3,3-trifluoro-propyl)-malonamic acid

To a solution of 2.30 g (7.87 mmol) 2-hydroxy-2-methyl-N-(3,3,3-trifluoro-propyl)-malonamic acid ethyl ester in 40 ml of tetrahydrofurane were added 0.33 g (7.87 mmol) of lithium hydroxide in 20 ml of water and the mixture was stirred overnight at room temperature. After concentration in vacuo water (50 ml) was added and the mixture was acidified to pH 1. Extraction with ethylacetate gave 1.46 g (81%) of the title compound as a solid, MS m/e (%): 228.1 (M–H, 100).

c) N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, entity A and entity B N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide was obtained as mixture of epimers according to the procedures described for example 2b using racemic 2-hydroxy-2-methyl-N-(3,3,3-trifluoro-propyl)-malonamic acid and (6R,7S)-7-amino-2-fluoro-6-methyl-9-(2,2,2-trifluoro-ethyl)-6,7-dihydro-9H-5-oxa-9-aza-benzocyclohepten-8-one. The epimers were separated by chromatography on Chiralpak AD using ethanol/heptane 15:85 to yield (−)-N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, entity A, MS m/e (%): 504.0 (M+H$^+$, 100), as first eluting fraction, and (−)-N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, entity B, as second eluting fraction, MS m/e (%): 504.0 (M+H$^+$, 100).

EXAMPLE 74

N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide

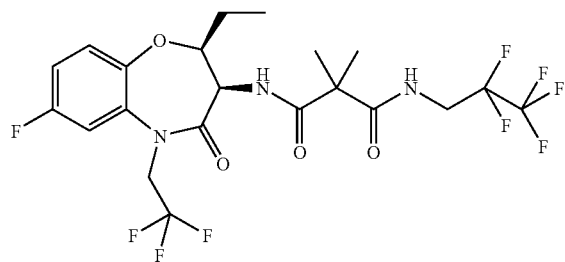

a) racemic (2S,3R and 2R,3S)-2-Dibenzylamino-3-hydroxy-pentanoic acid ethyl ester and racemic (2R,3R and 2S,3S)-2-Dibenzylamino-3-hydroxy-pentanoic acid ethyl ester A solution of 20 g (70.6 mmol) dibenzylamino-acetic acid ethyl ester in 240 ml tetrahydrofuran was stirred at −78° C. with 38.8 ml (77.6 mmol) lithium diisopropylamide (2M in heptane) for 30 minutes. 5.83 ml (77.6 mmol) Propionaldehyde in 5 ml tetrahydrofurane were added and stirring was continued overnight. The mixture was allowed to warm to room temprature, water was added and most of the organic solvent was removed by distillation. Extraction with ethylacetate and chromatography on silicagel with ethylacetate/heptane 1/5 yielded as first eluting fraction 6.85 g (28%) racemic (2S,3R and 2R,3S)-2-dibenzylamino-3-hydroxy-pentanoic acid ethyl ester, MS m/e (%): 342.3 (M+H$^+$, 100) and as second eluting fraction 6.15 g (26%) racemic (2R,3R and 2S,3S)-2-dibenzylamino-3-hydroxy-pentanoic acid ethyl ester, MS m/e (%): 342.2 (M+H$^+$, 100).

b) racemic (2S,3R and 2R,3S)-2-Dibenzylamino-3-hydroxy-pentanoic acid

To 17.7 g (51.9 mmol) racemic (2S,3R and 2R,3S)-2-dibenzylamino-3-hydroxy-pentanoic acid ethyl ester in 245 ml tetrahydrofurane were added 8.80 g (208 mmol) lithium hydroxide monohydrate dissolved in 44 ml water. The mixture was stirred at 60° C. for 2.5 days and the organic solvent was removed by distillation. Water was added followed by extraction with diethylether. The waterphase was adjusted to pH 1. Extraction with ethylacetate yielded 14.8 g (91%) racemic (2S,3R and 2R,3S)-2-dibenzylamino-3-hydroxy-pentanoic acid, MS m/e (%): 314.1 (M+H$^+$, 100).

c) racemic (2S,3R and 2R,3S)-2-Dibenzylamino-3-(4-fluoro-2-nitro-phenoxy)-pentanoic acid To 14.8 g (47.3 mmol) racemic (2S,3R and 2R,3S)-2-dibenzylamino-3-hydroxy-pentanoic acid in 90 ml dimethylformamide were added at 0° C. 8.26 g (189 mmol) sodium hydride (55%). The suspension was stirred for 2 hours and then 10.4 ml (94.6 mmol) 2,5-difluoro-nitrobenzene in 10 ml dimethylformamide were added. After stirring overnight the mixture was poured under cooling on aqueous 2M citric acid solution. Extraction with ethylacetate and chromatography on silicagel with ethylacetate/heptane (3:7) yielded 12.9 g (61%) racemic (2S,3R and 2R,3S)-2-dibenzylamino-3-(4-fluoro-2-nitro-phenoxy)-pentanoic acid as orange solid, MS m/e (%): 453.0 (M+H$^+$, 100).

d) racemic (2S,3R and 2R,3S)-3-(2-Amino-4-fluoro-phenoxy)-2-dibenzylamino-pentanoic acid 4.30 g (9.50 mmol) racemic (2S,3R and 2R,3S)-2-dibenzylamino-3-(4-fluoro-2-nitro-phenoxy)-pentanoic acid in 30 ml methanol were hydrogenated with 1.12 g Raney-Nickel. Filtration and removal of the solvent by distillation yielded 3.95 g (98%) (2S,3R and 2R,3S)-3-(2-amino-4-fluoro-phenoxy)-2-dibenzylamino-pentanoic acid as foam, MS m/e (%): 423.1 (M+H$^+$, 100).

e) racemic (6S,7R and 6R,7S)-7-Dibenzylamino-6-ethyl-2-fluoro-6,7-dihydro-9H-5-oxa-9-aza-benzocyclohepten-8-one The title compound was obtained in similar yield yield according to the procedures described for example 5c using racemic (2S,3R and 2R,3S)-3-(2-amino-4-fluoro-phenoxy)-2-dibenzylamino-pentanoic acid, MS m/e (%): 405.2 (M+H$^+$, 100).

f) (+)-(6S,7R)-7-Dibenzylamino-6-ethyl-2-fluoro-6,7-dihydro-9H-5-oxa-9-aza-benzocyclohepten-8-one and (−)-(6R,7S)-7-Dibenzylamino-6-ethyl-2-fluoro-6,7-dihydro-9H-5-oxa-9-aza-benzocyclohepten-8-one Racemic (6S,7R and 6R,7S)-7-dibenzylamino-6-ethyl-2-fluoro-6,7-dihydro-9H-5-oxa-9-aza-benzocyclohepten-8-one was separated by chiral HPLC on Chiralpak AD with isopropanol/heptane 20/80 to yield the title compounds.

g) (6R,7S)-7-Dibenzylamino-6-ethyl-2-fluoro-9-(2,2,2-trifluoro-ethyl)-6,7-dihydro-9H-5-oxa-9-aza-benzocyclohepten-8-one A solution of 0.50 g (1.24 mmol) (−)-(6R,7S)-7-dibenzylamino-6-ethyl-2-fluoro-6,7-dihydro-9H-5-oxa-9-aza-benzocyclohepten-8-one and 0.44 g (1.85 mmol) 2,2,2-trifluoroethyl triflate in 5 ml dimethylformamide were treated with 0.61 g (1.85 mmol) cesium carbonate for 18 hours. The mixture was extracted with water/ethylacetate. Chromatography on silicagel with heptane/ethylacetate 70:30 yielded 0.34 g (57%) (6R,7S)-7-dibenzylamino-6-ethyl-2-fluoro-9-(2,2,2-trifluoro-ethyl)-6,7-dihydro-9H-5-oxa-9-aza-benzocyclohepten-8-one, MS m/e (%): 487.4 (M+H+, 100).

h) (6R,7S)-7-Amino-6-ethyl-2-fluoro-9-(2,2,2-trifluoro-ethyl)-6,7-dihydro-9H-5-oxa-9-aza-benzocyclohepten-8-one The title compound was prepared in 66% yield by hydrogenation of (6R,7S)-7-dibenzylamino-6-ethyl-2-fluoro-9-(2,2,2-trifluoro-ethyl)-6,7-dihydro-9H-5-oxa-9-aza-benzocyclohepten-8-one in methanol with Pd/C (10%), MS m/e (%): 307.1 (M+H+, 100).

i) N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6R,7S)-7-amino-6-ethyl-2-fluoro-9-(2,2,2-trifluoro-ethyl)-6,7-dihydro-9H-5-oxa-9-aza-benzocyclohepten-8-one. MS m/e (%): 552.2 (M+H+, 100).

EXAMPLE 75a (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, entity A

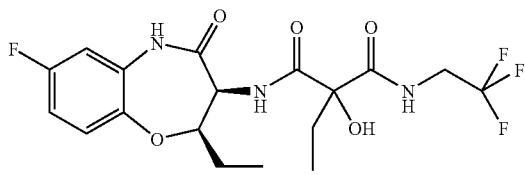

AND EXAMPLE 75b (S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, entity B a) (6R,7S)-7-Amino-6-ethyl-2-fluoro-6,7-dihydro-9H-5-oxa-9-aza-benzocyclohepten-8-one The title compound was prepared in quantitative yield by hydrogenation of (−)-(6R,7S)-7-dibenzylamino-6-ethyl-2-fluoro-6,7-dihydro-9H-5-oxa-9-aza-benzocyclohepten-8-one in methanol with Pd/C (10%), MS m/e (%): 225.3 (M+H+, 100).

b) 2-Ethyl-2-hydroxy-malonic acid monoethyl ester

The title compound was prepared in similar yields in analogy to example 66a starting from diethyl ethylmalonate, MS m/e (%): 175.1 (M−H, 100).

c) 2-Hydroxy-2-(2,2,2-trifluoro-ethylcarbamoyl)-butyric acid ethyl ester

The title compound was prepared in similar yields in analogy to example 72a starting from 2-ethyl-2-hydroxy-malonic acid monoethyl ester, MS m/e (%): 256.3 (M−H, 100).

d) 2-Hydroxy-2-(2,2,2-trifluoro-ethylcarbamoyl)-butyric acid

The title compound was prepared in similar yields in analogy to example 72c starting from 2-hydroxy-2-(2,2,2-trifluoro-ethylcarbamoyl)-butyric acid ethyl ester, MS m/e (%): 228.2 (M−H, 100).

e) (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, entity A and entity B (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide was obtained as mixture of epimers in 74% yield according to the procedures described for example 2b using 2-hydroxy-2-(2,2,2-trifluoro-ethylcarbamoyl)-butyric acid and (6R,7S)-7-amino-6-ethyl-2-fluoro-6,7-dihydro-9H-5-oxa-9-aza-benzocyclohepten-8-one. The epimers were separated by chromatography on Chiralpak AD using isopropanol/heptane 15:85 to yield (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, entity A, MS m/e (%): 436.1 (M+H+, 100), as first eluting fraction, and (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, entity B, as second eluting fraction, MS m/e (%): 436.1 (M+H+, 100).

EXAMPLE 76a (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, entity A

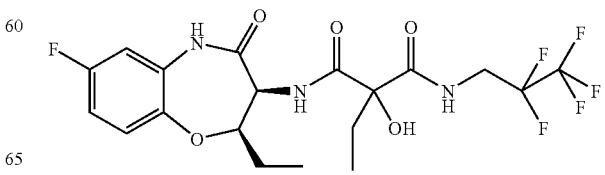

AND EXAMPLE 76b (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, entity B a) 2-Hydroxy-2-(2,2,3,3,3-pentafluoro-propylcarbamoyl)-butyric acid ethyl ester The title compound was prepared in similar yields in analogy to example 66b starting from 2-ethyl-2-hydroxy-malonic acid monoethyl ester, MS m/e (%): 306.2 (M−H, 100).

b) 2-Hydroxy-2-(2,2,3,3,3-pentafluoro-propylcarbamoyl)-butyric acid

The title compound was prepared in similar yields in analogy to example 66c starting from 2-hydroxy-2-(2,2,3,3,3-pentafluoro-propylcarbamoyl)-butyric acid ethyl ester, MS m/e (%): 278.1 (M−H, 100).

c) (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, entity A and entity B (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide was obtained as mixture of epimers in 66% yield according to the procedures described for example 2b using 2-hydroxy-2-(2,2,3,3,3-pentafluoro-propylcarbamoyl)-butyric acid and (6R,7S)-7-amino-6-ethyl-2-fluoro-6,7-dihydro-9H-5-oxa-9-aza-benzocyclohepten-8-one. The epimers were separated by chromatography on Chiralpak AD using isopropanol/heptane 10:90 to yield (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, entity A, MS m/e (%): 486.2 (M+H$^+$, 100), as first eluting-fraction, and (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, entity B, as second eluting fraction, MS m/e (%): 486.2 (M+H$^+$, 100).

EXAMPLE 77a (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, entity A

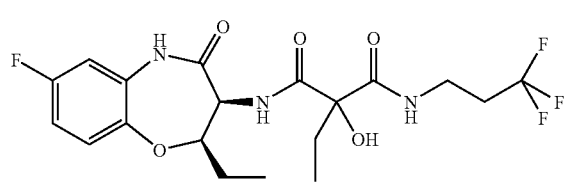

AND EXAMPLE 77b (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, entity B a) 2-Hydroxy-2-(3,3,3-trifluoro-propylcarbamoyl)-butyric acid ethyl ester The title compound was prepared in similar yields in analogy to example 73a starting from 2-ethyl-2-hydroxy-malonic acid monoethyl ester, MS m/e (%): 270.3 (M−H, 100).

b) 2-Hydroxy-2-(3,3,3-trifluoro-propylcarbamoyl)-butyric acid

The title compound was prepared in similar yields in analogy to example 73b starting from 2-hydroxy-2-(2,2,3,3,3-pentafluoro-propylcarbamoyl)-butyric acid ethyl ester, MS m/e (%): 242.1 (M−H, 100).

c) (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, entity A and entity B (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide was obtained as mixture of epimers in 43% yield according to the procedures described for example 2b using 2-hydroxy-2-(3,3,3-trifluoro-propylcarbamoyl)-butyric acid and (6R,7S)-7-amino-6-ethyl-2-fluoro-6,7-dihydro-9H-5-oxa-9-aza-benzocyclohepten-8-one. The epimers were separated by chromatography on Chiralpak AD using isopropanol/heptane 10:90 to yield (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, entity A, MS m/e (%): 450.1 (M+H$^+$, 100), as first eluting fraction, and (−)-(R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, entity B, as second eluting fraction, MS m/e (%): 450.1 (M+H$^+$, 100).

EXAMPLE 78a (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, entity A

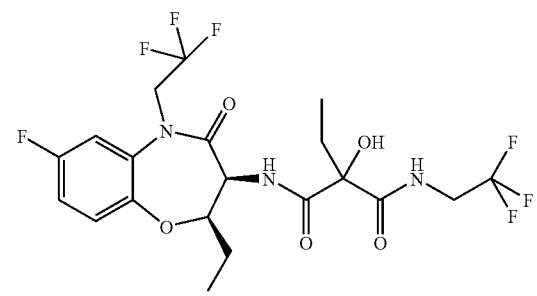

AND EXAMPLE 78b (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, entity B (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide was obtained as mixture of epimers in 70% yield according to the procedures described for example 2b using 2-hydroxy-2-(2,2,2-trifluoro-ethylcarbamoyl)-butyric acid and (6R,7S)-7-amino-6-ethyl-2-fluoro-9-(2,2,2-trifluoro-ethyl)-6,7-dihydro-9H-5-oxa-9-aza-benzocyclohepten-8-one. The epimers were separated by chromatography on Chiralpak AD using isopropanol/heptane 15:85 to yield (−)-(R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, entity A, MS m/e (%): 518.2 (M+H$^+$, 100), as first eluting fraction, and (−)-(R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, entity B, as second eluting fraction, MS m/e (%): 518.3 (M+H$^+$, 100).

EXAMPLE 79a (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, entity A

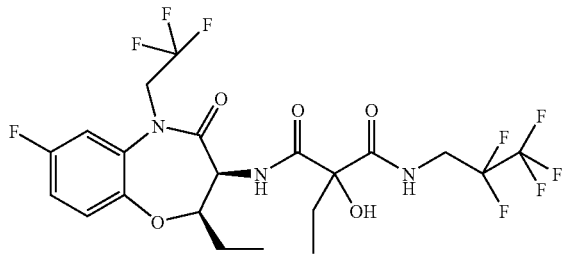

AND EXAMPLE 79b (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, entity B (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide was obtained as mixture of epimers in 62% yield according to the procedures described for example 2b using 2-hydroxy-2-(2,2,3,3,3-pentafluoro-propylcarbamoyl)-butyric acid and (6R,7S)-7-amino-6-ethyl-2-fluoro-9-(2,2,2-trifluoro-ethyl)-6,7-dihydro-9H-5-oxa-9-aza-benzocyclohepten-8-one. The epimers were separated by chromatography on Chiralpak AD using isopropanol/heptane 15:85 to yield (−)-(R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, entity A, MS m/e (%): 568.2 (M+H$^+$, 100), as first eluting fraction, and (−)-(R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, entity B, as second eluting fraction, MS m/e (%): 568.2 (M+H$^+$, 100).

EXAMPLE 80

N-[(6R,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide

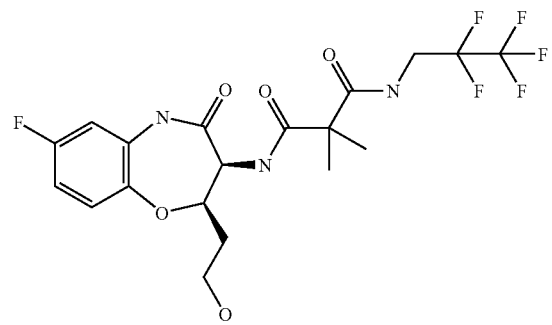

a) racemic (2S,3R and 2R,3S)-5-Benzyloxy-2-dibenzylamino-3-hydroxy-pentanoic acid ethyl ester and racemic (2R,3R and 2S,3S)-5-Benzyloxy-2-dibenzylamino-3-hydroxy-pentanoic acid ethyl ester A solution of 42 g (148 mmol) dibenzylamino-acetic acid ethyl ester in 1 l tetrahydrofuran was stirred at −70° C. with 87 ml (77.6 mmol) lithium diisopropylamide (2M in tetrahydrofurane) for 60 minutes. 28.7 g (175 mmol) 3-(Benzyloxy)propanal were added and stirring was continued overnight. The mixture was allowed to warm to room temperature and 200 ml saturated aqueous ammonium chloride solution was added. Extraction with diethylether and chromatography on silicagel with ethylacetate/heptane 0:100 to 100:0 yielded as first eluting fraction 13.0 g (20%) racemic (2S,3R and 2R,3S)-5-benzyloxy-2-dibenzylamino-3-hydroxy-pentanoic acid ethyl ester, MS m/e (%): 448.1 (M+H$^+$, 100) and as second diluting fraction 11.0 g (17%) racemic (2R,3R and 2S,3S)-5-benzyloxy-2-dibenzylamino-3-hydroxy-pentanoic acid ethyl ester, MS m/e (%): 448.1 (M+H$^+$, 100).

b) racemic (2S,3R and 2R,3S)-5-Benzyloxy-2-dibenzylamino-3-hydroxy-pentanoic acid To 13.0 g (29 mmol) racemic (2S,3R and 2R,3S)-5-benzyloxy-2-dibenzylamino-3-hydroxy-pentanoic acid ethyl ester in 150 ml tetrahydrofurane were added 4.88 g (116 mmol) lithium hydroxide monohydrate dissolved in 41 ml water. The mixture was stirred at 60° C. for 16 hours. A 1 M aqueous solution of potassium dihydrogenphosphate was added followed by extraction with ethylacetate. Chromatography on silicagel with heptane/etylacetate 4:1 to 1:1 yielded 8.57 g (70%) racemic (2S,3R and 2R,3S)-5-benzyloxy-2-dibenzylamino-3-hydroxy-pentanoic acid, MS m/e (%): 420.1 (M+H$^+$, 100).

c) racemic (2S,3R and 2R,3S)-5-Benzyloxy-2-dibenzylamino-3-(4-fluoro-2-nitro-phenoxy)-pentanoic acid 8.00 g (19 mmol) racemic (2S,3R and 2R,3S)-5-Benzyloxy-2-dibenzylamino-3-hydroxy-pentanoic acid in 25 ml dimethylformamide were added at 0° C. to a suspension of 1.83 g (42 mmol) sodium hydride (55%) in 25 ml dimethylformamide. The suspension was stirred for 3 hours and then 6.67 g (42 mmol) 2,5-difluoro-nitrobenzene in 10 ml dimethylformamide were added. After stirring overnight the mixture was poured under ice water and the pH was adjusted to 1. Extraction with ethylacetate and chromatography on silicagel with heptane/ethylacetate (2:1 to 1:1) yielded 9.1 g (85%) racemic (2S,3R and 2R,3S)-5-benzyloxy-2-dibenzylamino-3-(4-fluoro-2-nitro-phenoxy)-pentanoic acid as yellow oil, MS m/e (%): 559.3 (M+H$^+$, 100).

d) racemic (2S,3R and 2R,3S)-3-(2-Amino-4-fluoro-phenoxy)-5-benzyloxy-2-dibenzylamino-pentanoic acid 9.30 g (17 mmol) racemic (2S,3R and 2R,3S)-5-Benzyloxy-2-dibenzylamino-3-(4-fluoro-2-nitro-phenoxy)-pentanoic acid in 100 ml methanol were hydrogenated with 1.5 g Raney-Nickel. Filtration and removal of the solvent by distillation yielded 5.30 g (60%) (2S,3R and 2R,3S)-3-(2-amino-4-fluoro-phenoxy)-5-benzyloxy-2-dibenzylamino-pentanoic acid as foam, MS m/e (%): 529.0 (M+H$^+$, 100).

e) racemic (6S,7R and 6R,7S)-6-(2-Benzyloxy-ethyl)-7-dibenzylamino-2-fluoro-6,7-dihydro-9H-5-oxa-9-aza-benzocyclohepten-8-one The title compound was obtained in similar yield yield according to the procedures described for example 5c using racemic (2S,3R and 2R,3S)-3-(2-amino-4-fluoro-phenoxy)-5-benzyloxy-2-dibenzylamino-pentanoic acid, MS m/e (%): 511.5 (M+H$^+$, 100).

f) (+)-(6S,7R)-6-(2-Benzyloxy-ethyl)-7-dibenzylamino-2-fluoro-6,7-dihydro-9H-5-oxa-9-aza-benzocyclohepten-8-one and (−)-(6R,7S)-6-(2-Benzyloxy-ethyl)-7-dibenzylamino-2-fluoro-6,7-dihydro-9H-5-oxa-9-aza-benzocyclohepten-8-one Racemic (6S,7R and 6R,7S)-6-(2-benzyloxy-ethyl)-7-dibenzylamino-2-fluoro-6,7-dihydro-9H-5-oxa-9-aza-benzocyclohepten-8-one was separated by chiral HPLC on Chiralpak AD with isopropanol/heptane 10/90 to yield the title compounds.

g) (6R,7S)-7-Amino-2-fluoro-6-(2-hydroxy-ethyl)-6,7-dihydro-9H-5-oxa-9-aza-benzocyclohepten-8-one The title compound was prepared in 96% yield by hydrogenation of (6R,7S)-6-(2-benzyloxy-ethyl)-7-dibenzylamino-2-fluoro-6,7-dihydro-9H-5-oxa-9-aza-benzocyclohepten-8-one in methanol with Pd/C (10%), MS m/e (%): 241.3 (M+H$^+$, 100).

h) N-[(6R,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6R,7S)-7-amino-2-fluoro-6-(2-hydroxy-ethyl)-6,7-dihydro-9H-5-oxa-9-aza-benzocyclohepten-8-one, MS m/e (%): 486.1 (M+H$^+$, 100).

EXAMPLE 81

N-[(6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide

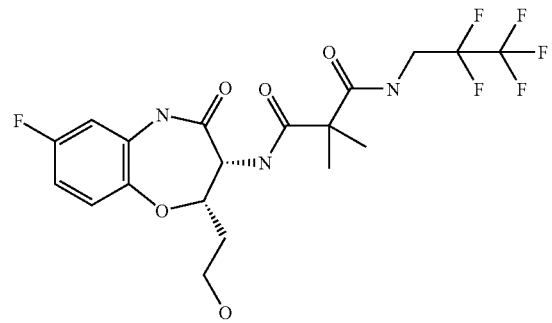

a) (6S,7R)-7-Amino-2-fluoro-6-(2-hydroxy-ethyl)-6,7-dihydro-9H-5-oxa-9-aza-benzocyclohepten-8-one The title compound was prepared in 96% yield by hydrogenation of (6S,7R)-6-(2-benzyloxy-ethyl)-7-dibenzylamino-2-fluoro-6,7-dihydro-9H-5-oxa-9-aza-benzocyclohepten-8-one in methanol with Pd/C (10%), MS m/e (%): 241.3 (M+H$^+$, 100).

b) N-[(6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide The title compound was obtained according to the procedures described for example 2b using 2,2-dimethyl-N-(2,2,3,3,3-pentafluoro-propyl)-malonamic acid and (6S,7R)-7-amino-2-fluoro-6-(2-hydroxy-ethyl)-6,7-dihydro-9H-5-oxa-9-aza-benzocyclohepten-8-one, MS m/e (%): 486.4 (M+H$^+$, 100).

EXAMPLE 82a

N-[(6S,7R)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity A

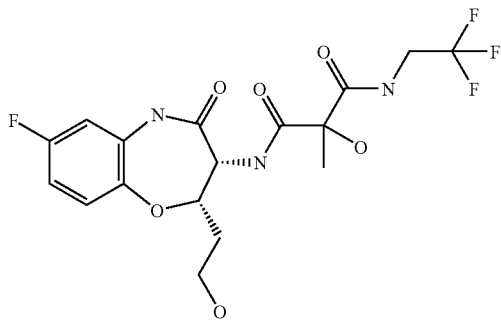

AND EXAMPLE 82b

N-[(6S,7R)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity B N-[(6S,7R)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamid, entitiy A, was obtained according to the procedures described for example 2b using (S or R)-2-hydroxy-2-methyl-N-(2,2,2-trifluoro-ethyl)-malonamic acid, entity B (example 72), and (6S,7R)-7-amino-2-fluoro-6-methyl-9-(2,2,2-trifluoro-ethyl)-6,7-dihydro-9H-5-oxa-9-aza-benzocyclohepten-8-one, MS m/e (%): 438.3 (M+H$^+$, 100).

N-[(6S,7R)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamid, entitiy B, was obtained according to the procedures described for example 2b using (S or R)-2-hydroxy-2-methyl-N-(2,2,2-trifluoro-ethyl)-malonamic acid, entity A (example 72), and (6S,7R)-7-amino-2-fluoro-6-methyl-9-(2,2,2-trifluoro-ethyl)-6,7-dihydro-9H-5-oxa-9-aza-benzocyclohepten-8-one, MS m/e (%): 438.4 (M+H$^+$, 100).

EXAMPLE 83a

N-[(6R,7S)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity A

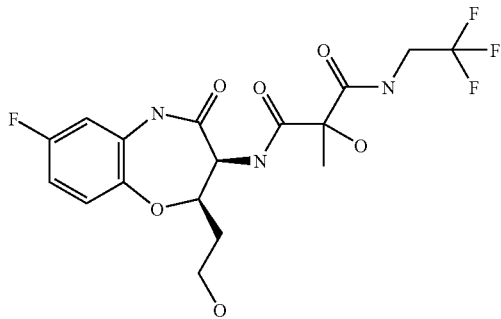

AND EXAMPLE 83b

N-[(6R,7S)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, entity B N-[(6R,7S)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl N'-(2,2,2-trifluoro-ethyl)-malonamid, entitiy A, was obtained according to the procedures described for example 2b using (S or R)-2-hydroxy-2-methyl-N-(2,2,2-trifluoro-ethyl)-malonamic acid, entity B (example 72), and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 438.4 (M+H$^+$, 100).

N-[(6R,7S)-2-Fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamid, entitiy B, was obtained according to the procedures described for example 2b using (S or R)-2-hydroxy-2-methyl-N-(2,2,2-trifluoro-ethyl)-malonamic acid, entity A (example 72), and (6R,7S)-7-amino-2-fluoro-6-methyl-9-(2,2,2-trifluoro-ethyl)-6,7-dihydro-9H-5-oxa-9-aza-benzocyclohepten-8-one, MS m/e (%): 438.3 (M+H$^+$, 100).

EXAMPLE 84a

N-[(6R,7R or 6S,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide, entity A

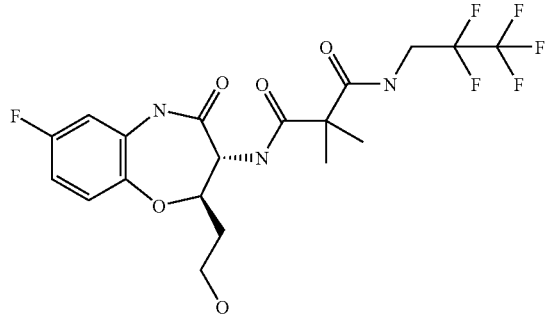

AND EXAMPLE 84b

N-[(6S,7S or 6R,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide, entity B a) racemic (2R,3R and 2S,3S)-5-Benzyloxy-2-dibenzylamino-3-hydroxy-pentanoic acid To 11.0 g (25 mmol) racemic (2R,3R and 2S,3S)-5-benzyloxy-2-dibenzylamino-3-hydroxy-pentanoic acid ethyl ester in 150 ml tetrahydrofurane were added 4.13 g (98 mmol) lithium hydroxide monohydrate dissolved in ~35 ml-water. The mixture was stirred at 60° C. overnight. A 1 M aqueous solution of potassium dihydrogenphosphate was added followed by extraction with ethylacetate. Chromatography on silicagel with heptane/etylacetate 4:1 to 1:1 yielded 6.60 g g (64%) racemic (2R,3R and 2S,3S)-5-benzyloxy-2-dibenzylamino-3-hydroxy-pentanoic acid, MS m/e (%): 420.1 (M+H+, 100).

b) racemic (2R,3R and 2S,3S)-5-Benzyloxy-2-dibenzylamino-3-(4-fluoro-2-nitro-phenoxy)-pentanoic acid 6.00 g (14 mmol) racemic (2R,3R and 2S,3S)-5-Benzyloxy-2-dibenzylamino-3-hydroxy-pentanoic acid in 20 ml dimethylformamide were added at 0° C. to a suspension of 1.37 g (31 mmol) sodium hydride (55%) in 25 ml dimethylformamide. The suspension was stirred for 3 hours and then 5.01 g (31 mmol) 2,5-difluoro-nitrobenzene in 10 ml dimethylformamide were added. After stirring overnight the mixture was poured under ice water and the pH was adjusted to 1. Extraction with ethylacetate and chromatography on silicagel with heptane/ethylacetate (4:1 to 1:1) yielded 6.00 g (75%) racemic (2R,3R and 2S,3S)-5-benzyloxy-2-dibenzylamino-3-(4-fluoro-2-nitro-phenoxy)-pentanoic acid as yellow oil, MS m/e (%): 559.3 (M+H+, 100).

c) racemic (2R,3R and 2S,3S)-3-(2-Amino-4-fluoro-phenoxy)-5-benzyloxy-2-dibenzylamino-pentanoic acid 6.00 g (11 mmol) racemic (2R,3R and 2S,3S)-5-Benzyloxy-2-dibenzylamino-3-(4-fluoro-2-nitro-phenoxy)-pentanoic acid in 100 ml methanol were hydrogenated with 1.5 g Raney-Nickel. Filtration and removal of the solvent by distillation yielded 5.57 g (98%) (2R,3R and 2S,3S)-3-(2-amino-4-fluoro-phenoxy)-5-benzyloxy-2-dibenzylamino-pentanoic acid as foam, MS m/e (%): 529.5 (M+H+, 100).

d) racemic (6R,7R and 6S,7S)-6-(2-Benzyloxy-ethyl)-7-dibenzylamino-2-fluoro-6,7-dihydro-9H-5-oxa-9-aza-benzocyclohepten-8-one The title compound was obtained in similar yield yield according to the procedures described for example 5c using racemic (2R,3R and 2S,3S)-3-(2-amino-4-fluoro-phenoxy)-5-benzyloxy-2-dibenzylamino-pentanoic acid, MS m/e (%): 511.5 (M+H+, 100).

e) (+)-(6R,7R or 6S,7S)-6-(2-Benzyloxy-ethyl)-7-dibenzylamino-2-fluoro-6,7-dihydro-9H-5-oxa-9-aza-benzocyclohepten-8-one and (−)-(6S,7S or 6R,7R)-6-(2-Benzyloxy-ethyl)-7-dibenzylamino-2-fluoro-6,7-dihydro-9H-5-oxa-9-aza-benzocyclohepten-8-one Racemic (6S,7R and 6R,7S)-6-(2-benzyloxy-ethyl)-7-dibenzylamino-2-fluoro-6,7-dihydro-9H-5-oxa-9-aza-benzocyclohepten-8-one was separated by chiral HPLC on Chiralpak AD with isopropanol/heptane 10/90 to yield the title compounds.

f) (6R,7R or 6S,7S)-7-Amino-2-fluoro-6-(2-hydroxy-ethyl)-6,7-dihydro-9H-5-oxa-9-aza-benzocyclohepten-8-one, entity A The title compound was prepared in 96% yield by hydrogenation of (+)-(6R,7R or 6S,7S)-6-(2-benzyloxy-ethyl)-7-dibenzylamino-2-fluoro-6,7-dihydro-9H-5-oxa-9-aza-benzocyclohepten-8-one in methanol with Pd/C (10%), MS m/e (%): 241.3 (M+H+, 100).

g) (6R,7R or 6S,7S)-7-Amino-2-fluoro-6-(2-hydroxy-ethyl)-6,7-dihydro-9H-5-oxa-9-aza-benzocyclohepten-8-one, entity B The title compound was prepared in 96% yield by hydrogenation of (−)-(6R,7R or 6S,7S)-6-(2-benzyloxy-ethyl)-7-dibenzylamino-2-fluoro-6,7-dihydro-9H-5-oxa-9-aza-benzocyclohepten-8-one in methanol with Pd/C (10%), MS m/e (%): 241.3 (M+H+, 100).

h) N-[(6R,7R or 6S,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide, entity A The title compound was obtained according to the procedures described for example 2b using 2,2-dimethyl-N-(2,2,3,3,3-pentafluoro-propyl)-malonamic acid and (6R,7R or 6S,7S)-7-amino-2-fluoro-6-(2-hydroxy-ethyl)-6,7-dihydro-9H-5-oxa-9-aza-benzocyclohepten-8-one, entity A, MS m/e (%): 486.3 (M+H+, 100).

h) N-[(6R,7R or 6S,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide, entity B The title compound was obtained according to the procedures described for example 2b using 2,2-dimethyl-N-(2,2,3,3,3-pentafluoro-propyl)-malonamic acid and (6R,7R or 6S,7S)-7-amino-2-fluoro-6-(2-hydroxy-ethyl)-6,7-dihydro-9H-5-oxa-9-aza-benzocyclohepten-8-one, entity B, MS m/e (%): 486.1 (M+H+, 100).

EXAMPLE 85a

N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, entity A

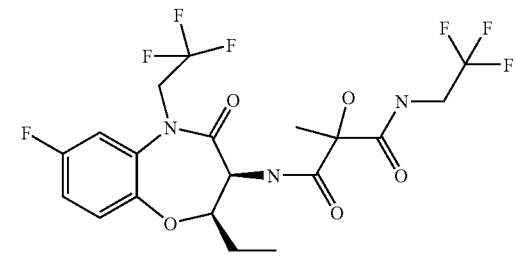

AND EXAMPLE 85b

N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, entity B N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, entity A, was obtained according to the procedures described for example 2b using (S or R)-2- hydroxy-2-methyl-N-(2,2,2-trifluoro-ethyl)-malonamic acid, entity B (example 72), and (6R,7S)-7-amino-6-ethyl-2-fluoro-9-(2,2,2-trifluoro-ethyl)-6,7-dihydro-9H-5-oxa-9-aza-benzocyclohepten-8-one, MS m/e (%): 504.0 (M+H⁺, 100). N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, entitiy B, was obtained according to the procedures described for example 2b using (S or R)-2-hydroxy-2-methyl-N-(2,2,2-trifluoro-ethyl)-malonamic acid, entity A (example 72), and (6R,7S)-7-amino-6-ethyl-2-fluoro-9-(2,2,2-trifluoro-ethyl)-6,7-dihydro-9H-5-oxa-9-aza-benzocyclohepten-8-one, MS m/e (%): 504.0 (M+H⁺, 100).

The invention claimed is:
1. A compound of formula I

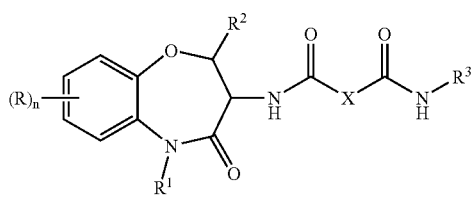

wherein
R is halogen, lower alkyl, lower alkyl substituted by halogen;
R¹ is hydrogen, lower alkyl, lower alkyl substituted by halogen or hydroxy, lower alkenyl, —(CH₂)ₙ-cycloalkyl, —(CH₂)ₙ—COR', benzyl optionally substituted by halogen, or —(CH₂)ₙ-morpholinyl;
R' is lower alkoxy, hydroxy, or amino;
R² is hydrogen, lower alkyl, di-lower alkyl, lower alkyl substituted by halogen or hydroxy, benzyl, or cycloalkyl;
R³ is lower alkyl, lower alkyl substituted by halogen, benzyl optionally substituted by two halogen atoms, —(CH₂)ₙ-cycloalkyl, or —(CH₂)ₙ-pyridinyl;
X is —CR⁴R⁴'— or —CR⁴R⁴'—O—;
R⁴ and R⁴' are each independently hydrogen, halogen, lower alkyl, lower alkoxy, hydroxy, or —CH₂-2-[1,3] dioxalan-; and
n is 0, 1, or 2;
or a pharmaceutically suitable acid addition salt thereof.
2. A compound of claim 1, wherein X is —CH₂—, —CHCH₃—, —CH(CH₂CH₃)—, —C(CH₃)₂—, —C(CH₃)(OH)—, —C(CH₃)₂—O—, —CH(OCH₃)— or —C(F)(CH₂CH₂CH₃)—.
3. A compound of claim 2, wherein X is —CH₂—.
4. A compound of claim 2, wherein X is —CHCH₃— or —CH(CH₂CH₃)—.
5. A compound of claim 4, wherein R³ is lower alkyl substituted by halogen.
6. A compound of claim 5, selected from the group consisting of
2-methyl-N-((S)-9-methyl-8-oxo-6,7,8,9-tetrahydro-5-oxa-9-aza-benzocyclohepten-7-yl)-N'-(2,2,3,3,3-pentafluoro-propyl)-malonamide,
2-methyl-N-((S)-9-methyl-8-oxo-4-trifluoromethyl-6,7,8,9-tetrahydro-5-oxa-9-aza-benzocyclohepten-7-yl)-N'-(2,2,3,3,3-pentafluoro-propyl)-malonamide-epimer 1,
2-methyl-N-((6R,7S)-6-methyl-8-oxo-6,7,8,9-tetrahydro-5-oxa-9-aza-benzocyclohepten-7-yl)-N'-(2,2,3,3,3-pentafluoro-propyl)-malonamide,
N-((6R,7S)-1-fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide,
N-((6R,7S)-2-fluoro-6-methyl-8-oxo-6,7,8,9-tetrahydro-5-oxa-9-aza-benzocyclohepten-7-yl)-2-methyl-N'-(2,2,3,3,3-pentafluoro-propyl)-malonamide,
N-((6R,7S)-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide,
N-((6R,7S)-6,9-dimethyl-8-oxo-6,7,8,9-tetrahydro-5-oxa-9-aza-benzocyclohepten-7-yl)-2-ethyl-N'-(2,2,3,3,3-pentafluoro-propyl)-malonamide,
N-[(6R,7S)-9-(4-chloro-benzyl)-6-methyl-8-oxo-6,7,8,9-tetrahydro-5-oxa-9-aza-benzocyclohepten-7-yl]-2-methyl-N'-(2,2,3,3,3-pentafluoro-propyl)-malonamide,
N-((6R,7S)-1-fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide and
N-((6R,7S)-2-fluoro-6,9-dimethyl-8-oxo-6,7,8,9-tetrahydro-5-oxa-9-aza-benzocyclohepten-7-yl)-2-methyl-N'-(2,2,3,3,3-pentafluoro-propyl)-malonamide.
7. A compound of claim 4, wherein R³ is benzyl substituted by two halogen atoms.
8. A compound of claim 7, which compound is N-(3,5-difluoro-benzyl)-2-methyl-N'-((6R,7S)-6-methyl-8-oxo-6,7,8,9-tetrahydro-5-oxa-9-aza-benzocyclohepten-7-yl)-malonamide.
9. A compound of claim 1, wherein X is —C(CH₃)₂.
10. A compound of claim 9, wherein R³ is lower alkyl substituted by halogen.
11. A compound of claim 10, selected from the group consisting of
N-((6R,7S)-1-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide,
N-[(6R,7S)-9-(4-chloro-benzyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide,
N-((6R,7S)-1-fluoro-6,9-dimethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide,
N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2,2-dimethyl-N'-(2,2,3,3,3-pentafluoro-propyl)-malonamide,
N-((6R,7S)-9-cyclopropylmethyl-2-fluoro-6-methyl-8-oxo-6,7,8,9-tetrahydro-5-oxa-9-aza-benzocyclohepten-7-yl)-2,2-dimethyl-N-(2,2,3,3,3-pentafluoro-propyl)-malonamide,
N-((6R,7S)-9-allyl-2-fluoro-6-methyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, and
N-[(6R,7S)-2-fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide.
12. A compound of claim 10, selected from the group consisting of
{(6R,7S)-2-fluoro-6-methyl-7-[2-methyl-2-(2,2,3,3,3-pentafluoro-propylcarbamoyl)-propionylamino]-8-oxo-7,8-dihydro-6H-5-oxa-9-aza-benzocyclohepten-9-yl}-acetic acid methyl ester, N-((6R,7S)-6-benzyl-2-fluoro-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-((6R,7S)-6-cyclopropyl-2-fluoro-8-oxo-6,7,8,9-tetrahydro-5-oxa-9-aza-benzocyclohepten-7-yl)-2,2-dimethyl-N-(2,2,3,3,3-pentafluoro-propyl)-malonamide, N-((6R,7S)-6-ethyl-8-oxo-6,7,8,9-tetrahydro-5-oxa-9-aza-benzocyclohepten-7-yl)-2,2-dimethyl-N'-(2,2,3,3,3-pentafluoro-propyl)-malonamide, N-[(6R,7S)-6-ethyl-2-fluoro-8-oxo-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide and N-[(6R,7S)-2-fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide.

13. A compound of claim 1, wherein X is —C(lower alkyl)(hydroxy).

14. A compound of claim 13, wherein R³ is lower alkyl substituted by halogen.

15. A compound of claim 14, selected from the group consisting of

N-((6R,7S)-6-cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide, N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-(R or S)-hydroxy-2-methyl-N-(2,2,3,3,3-pentafluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,3,3,3-pentafluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(3,3,3-trifluoro-propyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-2-fluoro-6-methyl-8-oxo-9-(2,2,2-trifluoro-ethyl)-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide, (S or R)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide, and (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide.

16. A compound of claim 14, selected from the group consisting of (R or S)-2-ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl) -6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl) -6,7,8,9-tetrahydro-5-oxa-9-aza-benzocyclohepten-7-yl]-2-hydroxy-N-(2,2,3,3,3-pentafluoro-propyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, N-[(6R,7S)-2-fluoro-6-(2-hydroxy-ethyl)-8-oxo-6,7,8,9-tetrahydro-5-oxa-9-aza-benzocyclohepten-7-yl]-2-(R or S)-hydroxy-2-methyl-N'-(2,2,2-trifluoro-ethyl)-malonamide, N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-(R or S)-2-hydroxy-2-methyl-N'-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide, (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide, and (R or S)-2-ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide.

17. A compound of claim 2, wherein X is —C(CH₃)₂—O—.

18. A compound of claim 2, wherein X is —C(F)(CH₂CH₂CH₃)—.

19. A compound of claim 18, wherein R³ is benzyl substituted by two halogen atoms.

20. A compound of claim 19, selected from the group consisting of

N-(3,5-difluoro-benzyl)-2-fluoro-N'-((6R,7S)-6-methyl-8-oxo-6,7,8,9-tetrahydro-5-oxa-9-aza-benzocyclohepten-7-yl)-2-propyl-malonamide and N-(3,5-difluoro-benzyl)-N'-((6R,7S)-6,9-dimethyl-8-oxo-6,7,8,9-tetrahydro-5-oxa-9-aza-benzocyclohepten-7-yl)-2-fluoro-2-propyl-malonamide.

21. A pharmaceutical composition comprising a therapeutically effective amount of a compound of formula I

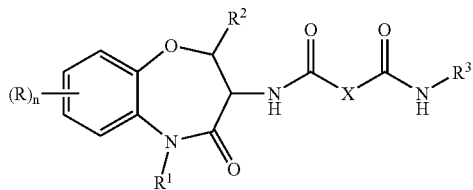

wherein
R is halogen, lower alkyl, lower alkyl substituted by halogen;
$R^1$ is hydrogen, lower alkyl, lower alkyl substituted by halogen or hydroxy, lower alkenyl, —$(CH_2)_n$-cycloalkyl, —$(CH_2)_n$—COR', benzyl optionally substituted by halogen, or —$(CH_2)_n$-morpholinyl;
R' is lower alkoxy, hydroxy, or amino;
$R^2$ is hydrogen, lower alkyl, di-lower alkyl, lower alkyl substituted by halogen or hydroxy, benzyl, or cycloalkyl;
$R^3$ is lower alkyl, lower alkyl substituted by halogen, benzyl optionally substituted by two halogen atoms, —$(CH_2)$-cycloalkyl, or —$(CH_2)_n$-pyridinyl;
X is —$CR^4R^{4'}$— or —$CR^4R^{4'}$—O—;
$R^4$ and $R^{4'}$ are each independently hydrogen, halogen, lower alkyl, lower alkoxy, hydroxy, or —$CH_2$-2-[1,3] dioxalan-; and
n is 0, 1, or 2;
or a pharmaceutically suitable acid addition salt thereof and a pharmaceutically acceptable carrier.

* * * * *